United States Patent
Thess et al.

(10) Patent No.: US 9,890,391 B2
(45) Date of Patent: Feb. 13, 2018

(54) RNA VECTOR WITH AN OPEN READING FRAME, AN ALBUMIN 3'-UTR, AND A HISTONE STEM LOOP

(71) Applicant: CureVac GmbH, Tubingen (DE)

(72) Inventors: Andreas Thess, Kusterdingen (DE); Karl-Josef Kallen, Tubingen (DE)

(73) Assignee: CureVac AG, Tübingen (DE)

( * ) Notice: Subject to any disclaimer, the term of this patent is extended or adjusted under 35 U.S.C. 154(b) by 0 days.

(21) Appl. No.: 14/388,220

(22) PCT Filed: Mar. 27, 2013

(86) PCT No.: PCT/EP2013/000936
§ 371 (c)(1),
(2) Date: Sep. 25, 2014

(87) PCT Pub. No.: WO2013/143698
PCT Pub. Date: Oct. 3, 2013

(65) Prior Publication Data
US 2015/0184195 A1  Jul. 2, 2015

(30) Foreign Application Priority Data

Mar. 27, 2012  (WO) .................. PCT/EP2012/001337
Jun. 8, 2012  (WO) .................. PCT/EP2012/002446

(51) Int. Cl.
| | | |
|---|---|---|
| *C12N 15/00* | (2006.01) | |
| *C12N 15/85* | (2006.01) | |
| *C12N 15/67* | (2006.01) | |
| *C12N 15/88* | (2006.01) | |
| *A61K 48/00* | (2006.01) | |

(52) U.S. Cl.
CPC ............. *C12N 15/85* (2013.01); *C12N 15/67* (2013.01); *C12N 15/88* (2013.01); *A61K 48/00* (2013.01); *C12N 2830/50* (2013.01)

(58) Field of Classification Search
USPC ...................................................... 435/320.1
See application file for complete search history.

(56) References Cited

U.S. PATENT DOCUMENTS

| | | | | |
|---|---|---|---|---|
| 4,624,926 A | * | 11/1986 | Inouye .................... | C07K 14/62 435/252.33 |
| 5,591,601 A | * | 1/1997 | Wagner .................. | C07K 14/61 435/320.1 |
| 5,874,260 A | * | 2/1999 | Cleuziat ............... | C12Q 1/6853 435/91.2 |
| 5,908,779 A | * | 6/1999 | Carmichael .......... | C12N 15/113 435/320.1 |
| 6,346,381 B1 | * | 2/2002 | Cohen .................... | C07K 14/47 435/6.14 |
| 6,355,415 B1 | * | 3/2002 | Wagner ................. | C12Q 1/6897 435/6.1 |
| 6,399,373 B1 | * | 6/2002 | Bougueleret ........ | C12N 9/6491 435/219 |
| 6,476,208 B1 | * | 11/2002 | Cohen .................... | C07K 14/47 435/320.1 |
| 6,555,316 B1 | * | 4/2003 | Cohen .................... | C07K 14/47 435/6.12 |
| 6,787,647 B1 | * | 9/2004 | Milne-Edwards ..... | C07K 14/47 435/252.3 |
| 6,969,763 B1 | * | 11/2005 | Ecker .................... | C07H 21/04 536/24.3 |
| 8,217,016 B2 | | 7/2012 | Hoerr et al. | |
| 8,383,340 B2 | | 2/2013 | Ketterer et al. | |
| 8,703,906 B2 | | 4/2014 | Baumhof et al. | |
| 8,968,746 B2 | | 3/2015 | Baumhof et al. | |
| 9,155,788 B2 | | 10/2015 | Hoerr et al. | |
| 2003/0143740 A1 | | 7/2003 | Wooddell et al. | |
| 2005/0032730 A1 | | 2/2005 | Von Der Mülbe et al. | |
| 2005/0250723 A1 | | 11/2005 | Hoerr et al. | |
| 2006/0188490 A1 | | 8/2006 | Hoerr et al. | |
| 2008/0025944 A1 | | 1/2008 | Hoerr et al. | |
| 2008/0267873 A1 | | 10/2008 | Hoerr et al. | |
| 2009/0324584 A1 | | 12/2009 | Hoerr et al. | |
| 2010/0120152 A1 | * | 5/2010 | Wooddell ............. | C07K 14/765 435/455 |

(Continued)

FOREIGN PATENT DOCUMENTS

| | | |
|---|---|---|
| WO | WO 1999/013090 | 3/1999 |
| WO | WO 2002/098443 | 12/2002 |

(Continued)

OTHER PUBLICATIONS

Wooddell (J. Gene Med., May 2008, vol. 10, No. 5, p. 551-563).*
Williams (NA Res., 1995, vol. 23, No. 4, p. 654-662).*
Emory (A 5'-terminal stem-loop structure can stabilize mRNA in *Escherichia coli*. Genes Dev 1992, 6: 135-148).*
Database EMBL Accession No. AA189340, Marra et al., "mt79h01.r1 Soares mouse lymph node NbMLN Mus musculus cDNA clone Image: 636145 5' similar to gb:A06977 serum albumin precursor (human); mRNA sequence," 1997.
Database EMBL Accession No. DR772399, Magness et al., "Illumigen_MCQ_54257 Katze_MNLV Macaca nemestrina cDNA clone IBIUW:37544 5' similar to Bases 5 to 513 highly similar to human ALB (Hs. 418167), mRNA sequence," 2005.

(Continued)

*Primary Examiner* — Michael Wilson
(74) *Attorney, Agent, or Firm* — Parker Highlander PLLC

(57) ABSTRACT

The invention relates to an artificial nucleic acid molecule comprising at least one open reading frame and at least one 3'UTR element comprising a nucleic acid sequence which is derived from the 3'UTR of an albumin gene or from a variant of the 3'UTR of an albumin gene. The invention further relates to the use of such an artificial nucleic acid molecule in gene therapy and/or genetic vaccination. Furthermore, the invention relates to the use of a 3'UTR element comprising a nucleic acid sequence which is derived from the 3'UTR of an albumin gene or from a variant of the 3'UTR of an albumin gene for the stabilization and/or prolongation of protein expression from a nucleic acid sequence comprising such 3'UTR element.

16 Claims, 23 Drawing Sheets

(56) References Cited

U.S. PATENT DOCUMENTS

| | | |
|---|---|---|
| 2010/0189729 A1 | 7/2010 | Hoerr et al. |
| 2010/0203076 A1 | 8/2010 | Fotin-Mleczek et al. |
| 2010/0239608 A1 | 9/2010 | Von Der Mülbe et al. |
| 2010/0291156 A1 | 11/2010 | Barner et al. |
| 2010/0303851 A1 | 12/2010 | Hoerr et al. |
| 2010/0305196 A1 | 12/2010 | Probst et al. |
| 2011/0053829 A1 | 3/2011 | Baumhof et al. |
| 2011/0077287 A1 | 3/2011 | Von Der Mülbe et al. |
| 2011/0250225 A1 | 10/2011 | Fotin-Mleczek et al. |
| 2011/0269950 A1 | 11/2011 | Von Der Mülbe et al. |
| 2011/0311472 A1 | 12/2011 | Hoerr et al. |
| 2012/0009221 A1 | 1/2012 | Hoerr et al. |
| 2012/0021043 A1 | 1/2012 | Kramps et al. |
| 2012/0213818 A1 | 8/2012 | Hoerr et al. |
| 2012/0258046 A1 | 10/2012 | Mutzke |
| 2013/0121988 A1 | 5/2013 | Hoerr et al. |
| 2013/0129754 A1 | 5/2013 | Thess et al. |
| 2013/0195867 A1 | 8/2013 | Hoerr et al. |
| 2013/0202645 A1 | 8/2013 | Barner et al. |
| 2013/0251742 A1 | 9/2013 | Probst et al. |
| 2013/0259879 A1 | 10/2013 | Baumhof et al. |
| 2013/0273001 A1 | 10/2013 | Hoerr et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2014/0037660 A1 | 2/2014 | Fotin-Mleczek et al. |
| 2014/0294877 A1 | 10/2014 | Baumhof et al. |
| 2015/0050302 A1 | 2/2015 | Thess |
| 2015/0057340 A1 | 2/2015 | Thess et al. |
| 2015/0093413 A1 | 4/2015 | Thess |
| 2015/0104476 A1 | 4/2015 | Von Der Mülbe et al. |
| 2015/0118183 A1 | 4/2015 | Baumhof |
| 2015/0118264 A1 | 4/2015 | Baumhof et al. |
| 2015/0141498 A1 | 5/2015 | Mutzke |
| 2015/0165006 A1 | 6/2015 | Thess et al. |
| 2015/0184195 A1 | 7/2015 | Thess et al. |
| 2015/0218554 A1 | 8/2015 | Thess |
| 2015/0258214 A1 | 9/2015 | Baumhof et al. |
| 2015/0306249 A1 | 10/2015 | Baumhof et al. |

FOREIGN PATENT DOCUMENTS

| | | |
|---|---|---|
| WO | WO 2010/038145 | 4/2010 |
| WO | WO 2012/019630 | 2/2012 |
| WO | WO 2012/019780 | 2/2012 |
| WO | WO 2012/170531 | 12/2012 |

OTHER PUBLICATIONS

Magness et al., "Analysis of the Macaca mulatta transcriptome and the sequence divergence between Macaca and human," *Genome Biology*, 6(7):R60, 2005.

Partridge et al., "Competition between the signal sequence and a 3'UTR localization signal during redirection of beta-globin mRNA to the endoplasmic reticulum: implications for biotechnology," *Cytotechnology*, 30(1-3):37-47, 1999.

PCT International Search Report and Written Opinion issued in International Application No. PCT/EP2013/000936, dated Jul. 18, 2013.

Peng et al., "The poly(A)-limiting element enhances mRNA accumulation by increasing the efficiency of pre-mRNA 3' processing," *RNA*, 11(6):958-965, 2005.

Takahashi et al., "Dicer and positive charge of proteins decrease the stability of RNA containing the AU-rich element of GM-CSF," *Biochemical and Biophysical Research Communications*, 340(3):807-814, 2006.

Wooddell et al., "Sustained liver-specific transgene expression from the albumin promoter in mice following hydrodynamic plasmid DNA delivery," *The Journal of Gene Medicine*, 10(5):551-563, 2008.

\* cited by examiner

PpLuc(GC) – A64 lacking a 3'-UTR

5'-GGGAGAAAGCTTGAGGA*TGGAGGACGCCAAGAACATCAAGAAGGGCCCGGCGCCCTTCTA*
*CCCGCTGGAGGACGGGACCGCCGGCGAGCAGCTCCACAAGGCCATGAAGCGGTACGCCCT*
*GGTGCCGGGCACGATCGCCTTCACCGACGCCCACATCGAGGTCGACATCACCTACGCGGA*
*GTACTTCGAGATGAGCGTGCGCCTGGCCGAGGCCATGAAGCGGTACGGCCTGAACACCAA*
*CCACCGGATCGTGGTGTGCTCGGAGAACAGCCTGCAGTTCTTCATGCCGGTGCTGGGCGC*
*CCTCTTCATCGGCGTGGCCGTCGCCCCGGCGAACGACATCTACAACGAGCGGGAGCTGCT*
*GAACAGCATGGGGATCAGCCAGCCGACCGTGGTGTTCGTGAGCAAGAAGGGCCTGCAGAA*
*GATCCTGAACGTGCAGAAGAAGCTGCCCATCATCCAGAAGATCATCATCATGGACAGCAA*
*GACCGACTACCAGGGCTTCCAGTCGATGTACACGTTCGTGACCAGCCACCTCCCGCCGGG*
*CTTCAACGAGTACGACTTCGTCCCGGAGAGCTTCGACCGGGACAAGACCATCGCCCTGAT*
*CATGAACAGCAGCGGCAGCACCGGCCTGCCGAAGGGGGTGGCCCTGCCGCACCGGACCGC*
*CTGCGTGCGCTTCTCGCACGCCCGGGACCCCATCTTCGGCAACCAGATCATCCCGGACAC*
*CGCCATCCTGAGCGTGGTGCCGTTCCACCACGGCTTCGGCATGTTCACGACCCTGGGCTA*
*CCTCATCTGCGGCTTCCGGGTGGTCCTGATGTACCGGTTCGAGGAGGAGCTGTTCCTGCG*
*GAGCCTGCAGGACTACAAGATCCAGAGCGCGCTGCTCGTGCCGACCCTGTTCAGCTTCTT*
*CGCCAAGAGCACCCTGATCGACAAGTACGACCTGTCGAACCTGCACGAGATCGCCAGCGG*
*GGGCGCCCCGCTGAGCAAGGAGGTGGGCGAGGCCGTGGCCAAGCGGTTCCACCTCCCGGG*
*CATCCGCCAGGGCTACGGCCTGACCGAGACCACGAGCGCGATCCTGATCACCCCCGAGGG*
*GGACGACAAGCCGGGCGCCGTGGGCAAGGTGGTCCCGTTCTTCGAGGCCAAGGTGGTGGA*
*CCTGGACACCGGCAAGACCCTGGGCGTGAACCAGCGGGGCGAGCTGTGCGTGCGGGGGCC*
*GATGATCATGAGCGGCTACGTGAACAACCCGGAGGCCACCAACGCCCTCATCGACAAGGA*
*CGGCTGGCTGCACAGCGGCGACATCGCCTACTGGGACGAGGACGAGCACTTCTTCATCGT*
*CGACCGGCTGAAGTCGCTGATCAAGTACAAGGGCTACCAGGTGGCGCCGGCCGAGCTGGA*
*GAGCATCCTGCTCCAGCACCCCAACATCTTCGACGCCGGCGTGGCCGGGCTGCCGGACGA*
*CGACGCCGGCGAGCTGCCGGCCGCGGTGGTGGTGCTGGAGCACGGCAAGACCATGACGGA*
*GAAGGAGATCGTCGACTACGTGGCCAGCCAGGTGACCACCGCCAAGAAGCTGCGGGGCGG*
*CGTGGTGTTCGTGGACGAGGTCCCGAAGGGCCTGACCGGGAAGCTCGACGCCCGGAAGAT*
*CCGCGAGATCCTGATCAAGGCCAAGAAGGGCGGCAAGATCGCCGTGTAAGACTAGTAGAT*
*CTAAAAAAAAAAAAAAAAAAAAAAAAAAAAAAAAAAAAAAAAAAAAAAAAAAAAAAAAAA*
*AAAAAA*-3'

Fig. 4

PpLuc(GC) – albumin – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCGTTCTTCGAGGCCAAGGTGGTGGA
CCTGGACACCGGCAAGACCCTGGGCGTGAACCAGCGGGGCGAGCTGTGCGTGCGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTG<u>CAT
CACATTTAAAAGCATCTCAGCCTACCATGAGAATAAGAGAAAGAAAATGAAGATCAAAAG
CTTATTCATCTGTTTTTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
TCTAGATCTAAAAAAAAAAAAAAAAAAAAAAAAAAAAAAAAAAAAAAAAAAAAAAAAAAA
AAAAAAAAAAAA</u>-3'

Fig. 5

PpLuc(GC) – albumin2 – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTG<u>CAT
CACATTTAAAAGCATCTCAGCCTACCATGAGAATAAGAGAAAGAAAATGAAGATCAAAAG
CTTATTCGTCTGTTTTTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
TCTA</u>GATCTAAAAAAAAAAAAAAAAAAAAAAAAAAAAAAAAAAAAAAAAAAAAAAAAAAA
AAAAAAAAAAAA-3'

Fig. 6

PpLuc(GC) – albumin3 – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTGCAT
CACATTTAAAAGCATCTCAGCCTACCATGAGAATAAGAGAAAGAAAATGAAGATCAAAAG
CTTATTCATCAGTTTTTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
TCTAGATCTAAAAAAAAAAAAAAAAAAAAAAAAAAAAAAAAAAAAAAAAAAAAAAAAAAA
AAAAAAAAAAAA-3'

Fig. 7

PpLuc(GC) – albumin4 – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTGCAT
CACATTTAAAAGCATCTCAGCCTACCATGAGAATAAGAGAAAGAAAATGAAGATCAAAAG
CTTATTCATCTCTTTTTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
TCTAGATCTAAAAAAAAAAAAAAAAAAAAAAAAAAAAAAAAAAAAAAAAAAAAAAAAAAA
AAAAAAAAAAAAA-3'

Fig. 8

PpLuc(GC) – albumin5 – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTGCAT
CACATTTAAAAGCATCTCAGCCTACCATGAGAATAAGAGAAAGAAAATGAAGATCAAAAG
CTTATTCATCTGTTGGTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
TCTAGATCTAAAAAAAAAAAAAAAAAAAAAAAAAAAAAAAAAAAAAAAAAAAAAAAAAAA
AAAAAAAAAAAAA-3'

Fig. 9

PpLuc(GC) – albumin6 – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTGCAT
CACATTTAAAAGCATCTCAGCCTACCATGAGAATAAGAGAAAGAAAATGAAGATCAATAG
CTTATTCATCTGTTTTTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
CCTAGATCTAAAAAAAAAAAAAAAAAAAAAAAAAAAAAAAAAAAAAAAAAAAAAAAAAAA
AAAAAAAAAAAA-3'

Fig. 10

PpLuc(GC) – albumin7 – A64

5'-GGGAGAAAGCTTGAGGA*TGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGCCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAG*ACTAGTGCAT
CACATTTAAAAGCATCTCAGCCTACCATGAGAATAAGAGAAAGAAAATGAAGATCAATAG
CTTATTCATCTCTTTTTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
CCTAGATCTAAAAAAAAAAAAAAAAAAAAAAAAAAAAAAAAAAAAAAAAAAAAAAAAAAA
AAAAAAAAAAAA-3'

Fig. 11

PpLuc(GC) – ag – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTTATA
AGACTGACTAGCCCGATGGGCCTCCCAACGGGCCCTCCTCCCCTCCTTGCACCGAGATTA
ATAGATCTAAAAAAAAAAAAAAAAAAAAAAAAAAAAAAAAAAAAAAAAAAAAAAAAAAAA
AAAAAAAAAAAA-3'

Fig. 12

PpLuc(GC) – gusb – A64

5'-GGGAGAAAGCTTGAGGA*TGGAGGACGCCAAGAACATCAAGAAGGGCCCGGCGCCCTTCTA*
*CCCGCTGGAGGACGGGACCGCCGGCGAGCAGCTCCACAAGGCCATGAAGCGGTACGCCCT*
*GGTGCCGGGCACGATCGCCTTCACCGACGCCCACATCGAGGTCGACATCACCTACGCGGA*
*GTACTTCGAGATGAGCGTGCGCCTGGCCGAGGCCATGAAGCGGTACGGCCTGAACACCAA*
*CCACCGGATCGTGGTGTGCTCGGAGAACAGCCTGCAGTTCTTCATGCCGGTGCTGGGCGC*
*CCTCTTCATCGGCGTGGCCGTCGCCCCGGCAACGACATCTACAACGAGCGGGAGCTGCT*
*GAACAGCATGGGGATCAGCCAGCCGACCGTGGTGTTCGTGAGCAAGAAGGGCCTGCAGAA*
*GATCCTGAACGTGCAGAAGAAGCTGCCCATCATCCAGAAGATCATCATCATGGACAGCAA*
*GACCGACTACCAGGGCTTCCAGTCGATGTACACGTTCGTGACCAGCCACCTCCCGCCGGG*
*CTTCAACGAGTACGACTTCGTCCCGGAGAGCTTCGACCGGGACAAGACCATCGCCCTGAT*
*CATGAACAGCAGCGGCAGCACCGGCCTGCCGAAGGGGGTGGCCCTGCCGCACCGGACCGC*
*CTGCGTGCGCTTCTCGCACGCCCGGGACCCCATCTTCGGCAACCAGATCATCCCGGACAC*
*CGCCATCCTGAGCGTGGTGCCGTTCCACCACGGCTTCGGCATGTTCACGACCCTGGGCTA*
*CCTCATCTGCGGCTTCCGGGTGGTCCTGATGTACCGGTTCGAGGAGGAGCTGTTCCTGCG*
*GAGCCTGCAGGACTACAAGATCCAGAGCGCGCTGCTCGTGCCGACCCTGTTCAGCTTCTT*
*CGCCAAGAGCACCCTGATCGACAAGTACGACCTGTCGAACCTGCACGAGATCGCCAGCGG*
*GGGCGCCCCGCTGAGCAAGGAGGTGGGCGAGGCCGTGGCCAAGCGGTTCCACCTCCCGGG*
*CATCCGCCAGGGCTACGGCCTGACCGAGACCACGAGCGCGATCCTGATCACCCCCGAGGG*
*GGACGACAAGCCGGGCGCCGTGGGCAAGGTGGTCCCGTTCTTCGAGGCCAAGGTGGTGGA*
*CCTGGACACCGGCAAGACCCTGGGCGTGAACCAGCGGGGCGAGCTGTGCGTGCGGGGGCC*
*GATGATCATGAGCGGCTACGTGAACAACCCGGAGGCCACCAACGCCCTCATCGACAAGGA*
*CGGCTGGCTGCACAGCGGCGACATCGCCTACTGGGACGAGGACGAGCACTTCTTCATCGT*
*CGACCGGCTGAAGTCGCTGATCAAGTACAAGGGCTACCAGGTGGCGCCGGCCGAGCTGGA*
*GAGCATCCTGCTCCAGCACCCCAACATCTTCGACGCCGGCGTGGCCGGGCTGCCGGACGA*
*CGACGCCGGCGAGCTGCCGGCCGCGGTGGTGGTGCTGGAGCACGGCAAGACCATGACGGA*
*GAAGGAGATCGTCGACTACGTGGCCAGCCAGGTGACCACCGCCAAGAAGCTGCGGGGCGG*
*CGTGGTGTTCGTGGACGAGGTCCCGAAGGGCCTGACCGGGAAGCTCGACGCCCGGAAGAT*
*CCGCGAGATCCTGATCAAGGCCAAGAAGGGCGGCAAGATCGCCGTGTAAGACTAGT*GCAA
GACTGATACCACCTGCGTGTCCCTTCCTCCCCGAGTCAGGGCGACTTCCACAGCAGCAGA
ACAAGTGCCTCCTGGACTGTTCACGGCAGACCAGAACGTTTCTGGCCTGGGTTTTGTGGT
CATCTATTCTAGCAGGGAACACTAAAGGTGGAAATAAAAGATTTTCTATTATGGAAATAA
AGAGTTGGCATGAAAGTGGCTACTGAGATCTAAAAAAAAAAAAAAAAAAAAAAAAAAAAA
AAAAAAAAAAAAAAAAAAAAAAAAAAAAAAAAA-3'

Fig. 13

PpLuc(GC) – atp5o – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTAAGT
<u>GTTGGTTTTCTGCCATCAGTGAAAATTCTTAAACTTGGAGCAACAATAAAAAGCTTCCAG</u>
<u>AACAGATCAGATCTAAAAAAAAAAAAAAAAAAAAAAAAAAAAAAAAAAAAAAAAAAAAAA</u>
<u>AAAAAAAAAAAAAAAAA</u>-3'

Fig. 14

PpLuc(GC) – ndufa1 – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTGGAA
GCATTTTCCTGATTGATGAAAAAAATAACTCAGTTATGGCCATCTACCCCTGCTAGAAGG
TTACAGTGTATTATGTAGCATGCAATGTGTTATGTAGTGCTTAATAAAAATAAAATGAAA
AAAATGCAGATCTAAAAAAAAAAAAAAAAAAAAAAAAAAAAAAAAAAAAAAAAAAAAAAA
AAAAAAAAAAAAAAAA-3'

Fig. 15

PpLuc(GC) – atp5I – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTAGAC
CAATCTTTAACATCTGATTATATTTGATTTATTATTTGAGTGTTGTTGGACCATGTGTGA
TCAGACTGCTATCTGAATAAAATAAGATTTGTCAAAACTCAGTGTTTTCTCCATCAGACA
CTCCATGAAAGGTCACAATTTCTCTTGATATTAAGCTGGGTTGTCTTTAAACAACCCTAA
ATACACGTCTGTTTAGCCCGCAATTGGAAAGGATATATGTGGCAATATTAACCTGGTACA
TGAATATATGGGGATAACATTTTAATTTGAAGGTTTGGAATATATATATTTAAGCTTTAT
TTCCAGAACAGTGAGGGTTAGGTCTTGGGAAAACTATAACTTGCCAAAGTAGAAGAAATA
GTAGTACCATATGCCAAAGTGATAGAGATGAATCATGTCAGTAGTTAGAATAACATTTCA
ACTGTTTTCTTTGCTAAAATCACAGAAAGACCCTATTGACAACATCTATGTCTGTAAAAA
TGTTAGAGTACTTGTCATCTTGAATATAGCCTCCCAAGAGAGAACAGGGTGGTATTCTA
AGTATGTTTCTTTGTAACATCTTTAGCAGTAGGACAGAGCCATACATGTGAAATCTGATT
TTTATGTGTGTTATTCGTTTGTCTGGTTTTACTACCTTTGCAAAAACAAAATACCCCAAA
GATATTTAAACAAGGTTATAATTTAGCATCTTCCCTGGATCTAAATAGTATATTATATCC
TGAAATAAATGAAATGATTGCTATAGATCTAAAAAAAAAAAAAAAAAAAAAAAAAAAAAA
AAAAAAAAAAAAAAAAAAAAAAAAAAAAAA-3'

Fig. 16

PpLuc(GC) – albumin8 – A64

5'-GGGAGAAAGCTTGAGGA*TGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGT*AAAC
ATCACAATTAAGAACATCTCAGCCTACCATGAGAACAAGAGAAATAAAATGAAGATCAAA
AGCTTATTCATCTGTTTTTCTTTTTCATTGGTATAAAGCCAACACCCTGTCTAAAAAACT
ATAAATTTCTTTAATCATTTTGCCTCTTTTCTCTGTGCTTCAATTAATAAAAAATGGAAA
GAATCTAGATCTAAAAAAAAAAAAAAAAAAAAAAAAAAAAAAAAAAAAAAAAAAAAAAAA
AAAAAAAAAAAAAAAA-3'

Fig. 22

PpLuc(GC) – albumin9 – A64

5'-GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTACAC
ATCACAACCACAACCTTCTCAGGCTACCCTGAGAAAAAAGACATGAAGACTCAGGACTC
ATCTTTTCTGTTGGTGTAAAATCAACACCCTAAGGAACACAAATTTCTTTAAACATTTGA
CTTCTTGTCTCTGTGCTGCAATTAATAAAAAATGGAAAGAATCTACAGATCTAAAAAAAA
AAAAAAAAAAAAAAAAAAAAAAAAAAAAAAAAAAAAAAAAAAAAAAAAAAAAAAAA-3'

Fig. 23

RNA VECTOR WITH AN OPEN READING FRAME, AN ALBUMIN 3'-UTR, AND A HISTONE STEM LOOP

This application is a national phase application under 35 U.S.C. §371 of International Application No. PCT/EP2013/000936, filed Mar. 27, 2013, which claims priority to International Application No. PCT/EP2012/001337, filed Mar. 27, 2012, and International Application No. PCT/EP2012/002446, filed Jun. 8, 2012. The entire text of each of the above referenced disclosures is specifically incorporated herein by reference.

The invention relates to artificial nucleic acid molecules comprising an open reading frame, a 3'-UTR element and optionally a poly(A) sequence and/or a polyadenylation-signal. The invention relates further to a vector comprising a 3'-UTR element, to a pharmaceutical composition comprising an artificial nucleic acid molecule and to a kit comprising an artificial nucleic acid molecule, a vector and/or a pharmaceutical composition comprising an artificial nucleic acid molecule, preferably for use in the field of gene therapy and/or genetic vaccination.

Gene therapy and genetic vaccination belong to the most promising and quickly developing methods of modern medicine. They may provide highly specific and individual options for therapy of a large variety of diseases. Particularly, inherited genetic diseases but also autoimmune diseases, cancerous or tumour-related diseases as well as inflammatory diseases may be the subject of such treatment approaches. Also, it is envisaged to prevent (early) onset of such diseases by these approaches.

The main conceptual rational behind gene therapy is appropriate modulation of impaired gene expression associated with pathological conditions of specific diseases. Pathologically altered gene expression may result in lack or overproduction of essential gene products, for example, signalling factors such as hormones, housekeeping factors, metabolic enzymes, structural proteins or the like. Altered gene expression may not only be due to misregulation of transcription and/or translation, but also due to mutations within the ORF coding for a particular protein. Pathological mutations may be caused by e.g. chromosomal aberration, or by more specific mutations, such as point or frame-shift-mutations, all of them resulting in limited functionality and, potentially, total loss of function of the gene product.

However, misregulation of transcription or translation may also occur, if mutations affect genes encoding proteins which are involved in the transcriptional or translational machinery of the cell. Such mutations may lead to pathological up- or down-regulation of genes which are—as such—functional. Genes encoding gene products which exert such regulating functions, may be, e.g., transcription factors, signal receptors, messenger proteins or the like. However, loss of function of such genes encoding regulatory proteins may, under certain circumstances, be reversed by artificial introduction of other factors acting further downstream of the impaired gene product. Such gene defects may also be compensated by gene therapy via substitution of the affected gene itself.

Genetic vaccination allows to evoke a desired immune response to selected antigens, such as characteristic components of bacterial surfaces, viral particles, tumour antigens or the like. Generally, vaccination is one of the pivotal achievements of modern medicine. However, effective vaccines are currently available only for a smaller number of diseases. Accordingly, infections that are not preventable by vaccination still affect millions of people every year.

Commonly, vaccines may be subdivided into "first", "second" and "third" generation vaccines. "First generation" vaccines are, typically, whole-organism vaccines. They are based on either live and attenuated or killed pathogens, e.g. viruses, bacteria or the like. The major drawback of live and attenuated vaccines is the risk for a reversion to lifethreatening variants. Thus, although attenuated, such pathogens may still intrinsically bear unpredictable risks. Killed pathogens may not be as effective as desired for generating a specific immune response. In order to minimize these risks, "second generation" vaccines were developed. These are, typically, subunit vaccines, consisting of defined antigens or recombinant protein components which are derived from pathogens.

Genetic vaccines, i.e. vaccines for genetic vaccination, are usually understood as "third generation" vaccines. They are typically composed of genetically engineered nucleic acid molecules which allow expression of peptide or protein (antigen) fragments characteristic for a pathogen or a tumor antigen in vivo. Genetic vaccines are expressed upon administration to a patient an uptake by competent cells. Expression of the administered nucleic acids results in production of the encoded proteins. In the event these proteins are recognized as foreign by the patient's immune system, an immune response is triggered.

As can be seen from the above, both methods, gene therapy and genetic vaccination, are essentially based on the administration of nucleic acid molecules to a patient and subsequent transcription and/or translation of the encoded genetic information. Alternatively, genetic vaccination or gene therapy may also comprise methods which include isolation of specific body cells from a patient to be treated, subsequent in vitro transfection of such cells, and re-administration of the treated cells to the patient.

DNA as well as RNA may be used as nucleic acid molecules for administration in the context of gene therapy or genetic vaccination. DNA is known to be relatively stable and easy to handle. However, the use of DNA bears the risk of undesired insertion of the administered DNA-fragments into the patient's genome potentially resulting in loss of function of the impaired genes. As a further risk, the undesired generation of anti-DNA antibodies has emerged. Another drawback is the limited expression level of the encoded peptide or protein that is achievable upon DNA administration and its transcription/translation. Among other reasons, the expression level of the administered DNA will be dependent on the presence of specific transcription factors which regulate DNA transcription. In the absence of such factors, DNA transcription will not yield satisfying amounts of RNA. As a result, the level of translated peptide or protein obtained is limited.

By using RNA instead of DNA for gene therapy or genetic vaccination, the risk of undesired genomic integration and generation of anti-DNA antibodies is minimized or avoided. However, RNA is considered to be a rather unstable molecular species which may readily be degraded by ubiquitous RNAses.

In vivo, RNA-degradation contributes to the regulation of the RNA half-life time. That effect was considered and proven to fine tune the regulation of eukaryotic gene expression (Friedel et al, Conserved principles of mammalian transcriptional regulation revealed by RNA half-life, Nucleic Acid Research, 2009, 1-12). Accordingly, each naturally occurring mRNA has its individual half-life depending on the gene from which the mRNA is derived. It contributes to the regulation of the expression level of this gene. Unstable RNAs are important to realize transient gene expression at distinct points in time. However, long-lived RNAs may be associated with accumulation of distinct proteins or continuous expression of genes. In vivo, the half life of mRNAs may also be dependent on environmental factors, such as hormonal treatment, as has been shown, e.g., for insulin-like growth factor I, actin, and albumin mRNA (Johnson et al., Newly synthesized RNA: Simultaneous measurement in intact cells of transcription rates and RNA stability of insulin-like growth factor I, actin, and albumin in growth hormone-stimulated hepatocytes, Proc. Natl. Acad. Sci., Vol. 88, pp. 5287-5291, 1991).

For gene therapy and genetic vaccination, usually stable RNA is desired. This is, on the one hand, due to the fact that the product encoded by the RNA-sequence shall accumulate in vivo. On the other hand, the RNA has to maintain its structural and functional integrity when prepared for a suitable dosage form, in the course of its storage, and when administered. Thus, considerable attention was dedicated to provide stable RNA molecules for gene therapy or genetic vaccination in order to prevent them from being subject to early degradation or decay.

It has been reported that the G/C-content of nucleic acid molecules may influence their stability. Thus, nucleic acids comprising an increased amount of guanine (G) and/or cytosine (C) residues may be functionally more stable than nucleic acids containing a large amount of adenine (A) and thymine (T) or uracil (U) nucleotides. In this context, WO02/098443 provides a pharmaceutical composition containing an mRNA that is stabilised by sequence modifications in the translated region. Such a sequence modification takes advantage of the degeneracy of the genetic code. Accordingly, codons which contain a less favourable combination of nucleotides (less favourable in terms of RNA stability) may be substituted by alternative codons without altering the encoded amino acid sequence. This method of RNA stabilization is limited by the provisions of the specific nucleotide sequence of each single RNA molecule which is not allowed to leave the space of the desired amino acid sequence. Also, that approach is restricted to coding regions of the RNA.

As an alternative option for mRNA stabilisation, it has been found that naturally occurring eukaryotic mRNA molecules contain characteristic stabilising elements. For example, they may comprise so-called untranslated regions (UTR) at their 5'-end (5'-UTR) and/or at their 3'-end (3'-UTR) as well as other structural features, such as a 5'-cap structure or a 3'-poly(A) tail. Both, 5'-UTR and 3'-UTR are typically transcribed from the genomic DNA and are, thus, an element of the premature mRNA. Characteristic structural features of mature mRNA, such as the 5'-cap and the 3'-poly(A) tail (also called poly(A) tail or poly(A) sequence) are usually added to the transcribed (premature) mRNA during mRNA processing.

A 3'-poly(A) tail is typically a monotonous sequence stretch of adenine nucleotides added to the 3'-end of the transcribed mRNA. It may comprise up to about 400 adenine nucleotides. It was found that the length of such a 3'-poly(A) tail is a potentially critical element for the stability of the individual mRNA.

Also, it was shown that the 3'UTR of α-globin mRNA may be an important factor for the well-known stability of α-globin mRNA (Rodgers et al., Regulated α-globin mRNA decay is a cytoplasmic event proceeding through 3'-to-5' exosome-dependent decapping, RNA, 8, pp. 1526-1537, 2002). The 3'UTR of α-globin mRNA is obviously involved in the formation of a specific ribonucleoprotein-complex, the α-complex, whose presence correlates with mRNA stability in vitro (Wang et al., An mRNA stability complex functions with poly(A)-binding protein to stabilize mRNA in vitro, Molecular and Cellular biology, Vol 19, No. 7, July 1999, p. 4552-4560).

Irrespective of factors influencing mRNA stability, effective translation of the administered nucleic acid molecules by the target cells or tissue is crucial for any approach using nucleic acid molecules for gene therapy or genetic vaccination. Along with the regulation of stability, also translation of the majority of mRNAs is regulated by structural features like UTRs, 5'-cap and 3'-poly(A) tail. In this context, it has been reported that the length of the poly(A) tail may play an important role for translational efficiency as well. Stabilizing 3'-elements, however, may also have an attenuating effect on translation.

It is the object of the invention to provide nucleic acid molecules which may be suitable for application in gene therapy and/or genetic vaccination. Particularly, it is the object of the invention to provide an mRNA species which is stabilized against preterm degradation or decay without exhibiting significant functional loss in translational efficiency. Another object of the present invention is to provide nucleic acid molecules coding for such a superior mRNA species which may be amenable for use in gene therapy and/or genetic vaccination. It is a further object of the present invention to provide a pharmaceutical composition for use in gene therapy and/or genetic vaccination. In summary, it is the object of the present invention to provide improved nucleic acid species which overcome the above discussed disadvantages of the prior art by a cost-effective and straight-forward approach.

The object underlying the present invention is solved by the claimed subject matter.

For the sake of clarity and readability the following definitions are provided. Any technical feature mentioned for these definitions may be read on each and every embodiment of the invention. Additional definitions and explanations may be specifically provided in the context of these embodiments.

Adaptive immune response: The adaptive immune response is typically understood to be an antigen-specific response of the immune system. Antigen specificity allows for the generation of responses that are tailored to specific pathogens or pathogen-infected cells. The ability to mount these tailored responses is usually maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. The three cell types that may serve as antigen-presenting cells are dendritic cells, macrophages, and B cells. Each of these cells has a distinct function in eliciting immune responses. Dendritic cells may take up antigens by phagocytosis and macropinocytosis and may become stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. MHC-molecules are, typically, responsible for presentation of an antigen to T-cells. Therein, presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind the antigen directly, but instead recognize short peptide fragments e.g. of pathogen-derived protein antigens, e.g. so-called epitopes, which are bound to MHC molecules on the surfaces of other cells.

Adaptive immune system: The adaptive immune system is essentially dedicated to eliminate or prevent pathogenic growth. It typically regulates the adaptive immune response by providing the vertebrate immune system with the ability to recognize and remember specific pathogens (to generate immunity), and to mount stronger attacks each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of such a cell will then inherit genes encoding the same receptor specificity, including the Memory B cells and Memory T cells that are the keys to long-lived specific immunity.

Adjuvant/adjuvant component: An adjuvant or an adjuvant component in the broadest sense is typically a pharmacological and/or immunological agent that may modify, e.g. enhance, the effect of other agents, such as a drug or vaccine. It is to be interpreted in a broad sense and refers to a broad spectrum of substances. Typically, these substances are able to increase the immunogenicity of antigens. For example, adjuvants may be recognized by the innate immune systems and, e.g., may elicit an innate immune response. "Adjuvants" typically do not elicit an adaptive immune response. Insofar, "adjuvants" do not qualify as antigens. Their mode of action is distinct from the effects triggered by antigens resulting in an adaptive immune response.

Antigen: In the context of the present invention "antigen" refers typically to a substance which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

Artificial nucleic acid molecule: An artificial nucleic acid molecule may typically be understood to be a nucleic acid molecule, e.g. a DNA or an RNA, that does not occur naturally. In other words, an artificial nucleic acid molecule may be understood as a non-natural nucleic acid molecule. Such nucleic acid molecule may be non-natural due to its individual sequence (which does not occur naturally) and/or due other modifications, e.g. structural modifications of nucleotides which do not occur naturally. An artificial nucleic acid molecule may be a DNA molecule, an RNA molecule or a hybrid-molecule comprising DNA and RNA portions. Typically, artificial nucleic acid molecules may be designed and/or generated by genetic engineering methods to correspond to a desired artificial sequence of nucleotides (heterologous sequence). In this context an artificial sequence is usually a sequence that may not occur naturally, i.e. it differs from the wild type sequence by at least one nucleotide. The term "wild type" may be understood as a sequence occurring in nature. Further, the term "artificial nucleic acid molecule" is not restricted to mean "one single molecule" but is, typically, understood to comprise an ensemble of identical molecules. Accordingly, it may relate to a plurality of identical molecules contained in an aliquot.

Bicistronic RNA, multicistronic RNA: A bicistronic or multicistronic RNA is typically an RNA, preferably an mRNA, that typically may have two (bicistronic) or more (multicistronic) open reading frames (ORF). An open reading frame in this context is a sequence of codons that is translatable into a peptide or protein.

Carrier/polymeric carrier: A carrier in the context of the invention may typically be a compound that facilitates transport and/or complexation of another compound (cargo). A polymeric carrier is typically a carrier that is formed of a polymer. A carrier may be associated to its cargo by covalent or non-covalent interaction. A carrier may transport nucleic acids, e.g. RNA or DNA, to the target cells. The carrier may—for some embodiments—be a cationic component.

Cationic component: The term "cationic component" typically refers to a charged molecule, which is positively charged (cation) at a pH value typically from 1 to 9, preferably at a pH value of or below 9 (e.g. from 5 to 9), of or below 8 (e.g. from 5 to 8), of or below 7 (e.g. from 5 to 7), most preferably at a physiological pH, e.g. from 7.3 to 7.4. Accordingly, a cationic component may be any positively charged compound or polymer, preferably a cationic peptide or protein which is positively charged under physiological conditions, particularly under physiological conditions in vivo. A "cationic peptide or protein" may contain at least one positively charged amino acid, or more than one positively charged amino acid, e.g. selected from Arg, His, Lys or Orn. Accordingly, "polycationic" components are also within the scope exhibiting more than one positive charge under the conditions given.

5'-cap: A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. Further examples of 5' cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety.

Cellular immunity/cellular immune response: Cellular immunity relates typically to the activation of macrophages, natural killer cells (NK), antigen-specific cytotoxic T-lymphocytes, and the release of various cytokines in response to an antigen. In more general terms, cellular immunity is not based on antibodies, but on the activation of cells of the immune system. Typically, a cellular immune response may be characterized e.g. by activating antigen-specific cytotoxic T-lymphocytes that are able to induce apoptosis in cells, e.g. specific immune cells like dendritic cells or other cells, displaying epitopes of foreign antigens on their surface. Such cells may be virus-infected or infected with intracellular bacteria, or cancer cells displaying tumor antigens. Further characteristics may be activation of macrophages and natural killer cells, enabling them to destroy pathogens and stimulation of cells to secrete a variety of cytokines that influence the function of other cells involved in adaptive immune responses and innate immune responses.

DNA: DNA is the usual abbreviation for deoxy-ribo-nucleic-acid. It is a nucleic acid molecule, i.e. a polymer consisting of nucleotides. These nucleotides are usually deoxyadenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerise by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single stranded or double stranded. In the double stranded form, the nucleotides of the first strand typically hybridize with the nucleotides of the second strand, e.g. by A/T-base-pairing and G/C-base-pairing.

Epitope: (also called "antigen determinant") can be distinguished in T cell epitopes and B cell epitopes. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Fragment of a sequence: A fragment of a sequence may typically be a shorter portion of a full-length sequence of e.g. a nucleic acid molecule or an amino acid sequence. Accordingly, a fragment, typically, consists of a sequence that is identical to the corresponding stretch within the full-length sequence. A preferred fragment of a sequence in the context of the present invention, consists of a continuous stretch of entities, such as nucleotides or amino acids corresponding to a continuous stretch of entities in the molecule the fragment is derived from, which represents at least 20%, preferably at least 30%, more preferably at least 40%, more preferably at least 50%, even more preferably at least 60%, even more preferably at least 70%, and most preferably at least 80% of the total (i.e. full-length) molecule from which the fragment is derived.

G/C modified: A G/C-modified nucleic acid may typically be a nucleic acid, preferably an artificial nucleic acid molecule as defined herein, based on a modified wild-type sequence comprising a preferably increased number of guanosine and/or cytosine nucleotides as compared to the wild-type sequence. Such an increased number may be generated by substitution of codons containing adenosine or thymidine nucleotides by codons containing guanosine or cytosine nucleotides. If the enriched G/C content occurs in a coding region of DNA or RNA, it makes use of the degeneracy of the genetic code. Accordingly, the codon substitutions preferably do not alter the encoded amino acid residues, but exclusively increase the G/C content of the nucleic acid molecule.

Gene therapy: Gene therapy may typically be understood to mean a treatment of a patient's body or isolated elements of a patient's body, for example isolated tissues/cells, by nucleic acids encoding a peptide or protein. It typically may comprise at least one of the steps of a) administration of a nucleic acid, preferably an artificial nucleic acid molecule as defined herein, directly to the patient—by whatever administration route—or in vitro to isolated cells/tissues of the patient, which results in transfection of the patient's cells either in vivo/ex vivo or in vitro; b) transcription and/or translation of the introduced nucleic acid molecule; and optionally c) re-administration of isolated, transfected cells to the patient, if the nucleic acid has not been administered directly to the patient.

Genetic vaccination: Genetic vaccination may typically be understood to be vaccination by administration of a nucleic acid molecule encoding an antigen or an immunogen or fragments thereof. The nucleic acid molecule may be administered to a subject's body or to isolated cells of a subject. Upon transfection of certain cells of the body or upon transfection of the isolated cells, the antigen or immunogen may be expressed by those cells and subsequently presented to the immune system, eliciting an adaptive, i.e. antigen-specific immune response. Accordingly, genetic vaccination typically comprises at least one of the steps of a) administration of a nucleic acid, preferably an artificial nucleic acid molecule as defined herein, to a subject, preferably a patient, or to isolated cells of a subject, preferably a patient, which usually results in transfection of the subject's cells either in vivo or in vitro; b) transcription and/or translation of the introduced nucleic acid molecule; and optionally c) re-administration of isolated, transfected cells to the subject, preferably the patient, if the nucleic acid has not been administered directly to the patient.

Heterologous sequence: Two sequences are typically understood to be 'heterologous' if they are not derivable from the same gene. I.e., although heterologous sequences may be derivable from the same organism, they naturally (in nature) do not occur in the same nucleic acid molecule, such as in the same mRNA.

Humoral immunity/humoral immune response: Humoral immunity refers typically to antibody production and optionally to accessory processes accompanying antibody production. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Immunogen: In the context of the present invention an immunogen may be typically understood to be a compound that is able to stimulate an immune response. Preferably, an immunogen is a peptide, polypeptide, or protein. In a particularly preferred embodiment, an immunogen in the sense of the present invention is the product of translation of a provided nucleic acid molecule, preferably an artificial nucleic acid molecule as defined herein. Typically, an immunogen elicits at least an adaptive immune response.

Immunostimulatory composition: In the context of the invention, an immunostimulatory composition may be typically understood to be a composition containing at least one component which is able to induce an immune response or from which a component which is able to induce an immune response is derivable. Such immune response may be preferably an innate immune response or a combination of an adaptive and an innate immune response. Preferably, an immunostimulatory composition in the context of the invention contains at least one artificial nucleic acid molecule, more preferably an RNA, for example an mRNA molecule. The immunostimulatory component, such as the mRNA may be complexed with a suitable carrier. Thus, the immunostimulatory composition may comprise an mRNA/carrier-complex. Furthermore, the immunostimulatory composition may comprise an adjuvant and/or a suitable vehicle for the immunostimulatory component, such as the mRNA.

Immune response: An immune response may typically be a specific reaction of the adaptive immune system to a particular antigen (so called specific or adaptive immune response) or an unspecific reaction of the innate immune system (so called unspecific or innate immune response), or a combination thereof.

Immune system: The immune system may protect organisms from infection. If a pathogen succeeds in passing a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts typically contains so called humoral and cellular components.

Immunostimulatory RNA: An immunostimulatory RNA (isRNA) in the context of the invention may typically be an RNA that is able to induce an innate immune response. It usually does not have an open reading frame and thus does not provide a peptide-antigen or immunogen but elicits an immune response e.g. by binding to a specific kind of Toll-like-receptor (TLR) or other suitable receptors. However, of course also mRNAs having an open reading frame and coding for a peptide/protein may induce an innate immune response and, thus, may be immunostimulatory RNAs.

Innate immune system: The innate immune system, also known as non-specific (or unspecific) immune system, typically comprises the cells and mechanisms that defend the host from infection by other organisms in a non-specific manner. This means that the cells of the innate system may recognize and respond to pathogens in a generic way, but unlike the adaptive immune system, it does not confer long-lasting or protective immunity to the host. The innate immune system may be, e.g., activated by ligands of Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. The pharmaceutical composition according to the present invention may comprise one or more such substances. Typically, a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system; and/or acting as a physical and chemical barrier to infectious agents.

Cloning site: A cloning site is typically understood to be a segment of a nucleic acid molecule, which is suitable for insertion of a nucleic acid sequence, e.g., a nucleic acid sequence comprising an open reading frame. Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes which cleave the DNA at these sites. A cloning site which comprises more than one restriction site may also be termed a multiple cloning site (MCS) or a polylinker.

Nucleic acid molecule: A nucleic acid molecule is a molecule comprising, preferably consisting of nucleic acid components. The term nucleic acid molecule preferably refers to DNA or RNA molecules. It is preferably used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Open reading frame: An open reading frame (ORF) in the context of the invention may typically be a sequence of several nucleotide triplets which may be translated into a peptide or protein. An open reading frame preferably contains a start codon, i.e. a combination of three subsequent nucleotides coding usually for the amino acid methionine (ATG), at its 5'-end and a subsequent region which usually exhibits a length which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g. ATG) and which preferably terminates with a stop codon (e.g., TAA, TGA, or TAG). The open reading frame may be isolated or it may be incorporated in a longer nucleic acid sequence, for example in a vector or an mRNA. An open reading frame may also be termed "protein coding region".

Peptide: A peptide or polypeptide is typically a polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units.

Pharmaceutically effective amount: A pharmaceutically effective amount in the context of the invention is typically understood to be an amount that is sufficient to induce a pharmaceutical effect, such as an immune response, altering a pathological level of an expressed peptide or protein, or substituting a lacking gene product, e.g., in case of a pathological situation.

Protein A protein typically comprises one or more peptides or polypeptides. A protein is typically folded into 3-dimensional form, which may be required for to protein to exert its biological function.

Poly(A) sequence: A poly(A) sequence, also called poly (A) tail or 3'-poly(A) tail, is typically understood to be a sequence of adenine nucleotides, e.g., of up to about 400 adenine nucleotides, e.g. from about 20 to about 400, preferably from about 50 to about 400, more preferably from about 50 to about 300, even more preferably from about 50 to about 250, most preferably from about 60 to about 250 adenine nucleotides. A poly(A) sequence is typically-located at the 3' end of an mRNA. In the context of the present invention, a poly(A) sequence may be located within an mRNA or any other nucleic acid molecule, such as, e.g., in a vector, for example, in a vector serving as template for the generation of an RNA, preferably an mRNA, e.g., by transcription of the vector.

Polyadenylation: Polyadenylation is typically understood to be the addition of a poly(A) sequence to a nucleic acid molecule, such as an RNA molecule, e.g. to a premature mRNA. Polyadenylation may be induced by a so called polyadenylation signal. This signal is preferably located within a stretch of nucleotides at the 3'-end of a nucleic acid molecule, such as an RNA molecule, to be polyadenylated. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called premature-mRNA). Typically, RNA maturation (from pre-mRNA to mature mRNA) comprises the step of polyadenylation.

Restriction site: A restriction site, also termed restriction enzyme recognition site, is a nucleotide sequence recognized by a restriction enzyme. A restriction site is typically a short, preferably palindromic nucleotide sequence, e.g. a sequence comprising 4 to 8 nucleotides. A restriction site is preferably specifically recognized by a restriction enzyme.

The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence.

RNA, mRNA: RNA is the usual abbreviation for ribonucleic-acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino-acid sequence of a particular peptide or protein. Typically, a mature mRNA comprises a 5'-cap, a 5'UTR, an open reading frame, a 3'UTR and a poly(A) sequence. Aside from messenger RNA, several non-coding types of RNA exist which may be involved in regulation of transcription and/or translation.

Sequence of a nucleic acid molecule: The sequence of a nucleic acid molecule is typically understood to be the particular and individual order, i.e. the succession of its nucleotides. The sequence of a protein or peptide is typically understood to be the order, i.e. the succession of its amino acids.

Sequence identity: Two or more sequences are identical if they exhibit the same length and order of nucleotides or amino acids. The percentage of identity typically describes the extent to which two sequences are identical, i.e. it typically describes the percentage of nucleotides that correspond in their sequence position with identical nucleotides of a reference-sequence. For determination of the degree of identity, the sequences to be compared are considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides of a sequence which have the same position in two or more sequences having the same length. Gaps are usually regarded as non-identical positions, irrespective of their actual position in an alignment.

Stabilized nucleic acid molecule: A stabilized nucleic acid molecule is a nucleic acid molecule, preferably a DNA or RNA molecule that is modified such, that it is more stable to disintegration or degradation, e.g., by environmental factors or enzymatic digest, such as by an exo- or endonuclease degradation, than the nucleic acid molecule without the modification. Preferably, a stabilized nucleic acid molecule in the context of the present invention is stabilized in a cell, such as a prokaryotic or eukaryotic cell, preferably in a mammalian cell, such as a human cell. The stabilization effect may also be exerted outside of cells, e.g. in a buffer solution etc., for example, in a manufacturing process for a pharmaceutical composition comprising the stabilized nucleic acid molecule.

Transfection: The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Vaccine: A vaccine is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response.

Vector: The term "vector" refers to a nucleic acid molecule, preferably to an artificial nucleic acid molecule. A vector in the context of the present invention is suitable for incorporating or harboring a desired nucleic acid sequence, such as a nucleic acid sequence comprising an open reading frame. Such vectors may be storage vectors, expression vectors, cloning vectors, transfer vectors etc. A storage vector is a vector which allows the convenient storage of a nucleic acid molecule, for example, of an mRNA molecule. Thus, the vector may comprise a sequence corresponding, e.g., to a desired mRNA sequence or a part thereof, such as a. sequence corresponding to the open reading frame and the 3'UTR of an mRNA. An expression vector may be used for production of expression products such as RNA, e.g. mRNA, or peptides, polypeptides or proteins. For example, an expression vector may comprise sequences needed for transcription of a sequence stretch of the vector, such as a promoter sequence, e.g. an RNA promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. Preferably, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Vehicle: A vehicle is typically understood to be a material that is suitable for storing, transporting, and/or administering a compound, such as a pharmaceutically active compound. For example, it may be a physiologically acceptable liquid which is suitable for storing, transporting, and/or administering a pharmaceutically active compound.

3'-untranslated region (3'UTR): A 3'UTR is typically the part of an mRNA which is located between the protein coding region (open reading frame (ORF) or coding sequence (CDS)) and the poly(A) sequence of the mRNA. A 3'UTR of the mRNA is not translated into an amino acid sequence. The 3'UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5' capping, splicing the pre-mature mRNA to excize optional introns and modifications of the 3'-end, such as polyadenylation of the 3'-end of the pre-mature mRNA and optional endo-/or exonuclease cleavages etc. In the context of the present invention, a 3'UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'UTR sequence may be an RNA sequence, such as in the mRNA sequence used for defining the 3'UTR sequence, or a DNA sequence which corresponds to such RNA sequence. In the context of the present invention, the term "a 3'UTR of a gene", such as "a 3'UTR of an albumin gene", is the sequence which corresponds to the 3'UTR of the mature mRNA derived from this gene, i.e. the mRNA obtained by transcription of the gene and maturation of the pre-mature mRNA. The term "3'UTR of a gene" encompasses the DNA sequence and the RNA sequence of the 3'UTR.

In a first aspect, the present invention relates to an artificial nucleic acid molecule comprising
  a. at least one open reading frame (ORF); and
  b. at least one 3'-untranslated region element (3'UTR element) comprising or consisting of a nucleic acid sequence which is derived from the 3'UTR of an albumin gene or from a variant of the 3'UTR of an albumin gene.

The term "3'UTR element" refers to a nucleic acid sequence which comprises or consists of a nucleic acid sequence that is derived from a 3'UTR or from a variant of a 3'UTR. A '3'-UTR element' preferably refers to a nucleic acid sequence which represents a 3'UTR of an artificial nucleic acid sequence, such as an artificial mRNA, or which codes for a 3'UTR of an artificial nucleic acid molecule. Accordingly, in the sense of the present invention, preferably, a 3'UTR element may be the 3'UTR of an mRNA, preferably of an artificial mRNA, or it may be the transcription template for a 3'UTR of an mRNA. Thus, a 3'UTR element preferably is a nucleic acid sequence which corresponds to the 3'UTR of an mRNA, preferably to the 3'UTR of an artificial mRNA, such as an mRNA obtained by transcription of a genetically engineered vector construct. Preferably, a 3'UTR element in the sense of the present invention functions as a 3'UTR or codes for a nucleotide sequence that fulfils the function of a 3'UTR.

Preferably, the at least one open reading frame and the at least one 3'UTR element are heterologous. The term "heterologous" in this context means that the open reading frame and the 3'UTR element are not occurring naturally (in nature) in this combination. Preferably, the 3'UTR element is derived from a different gene than the open reading frame. For example, the ORF may be derived from a different gene than the 3'UTR element, e.g. encoding a different protein or the same protein but of a different species etc. Preferably, the open reading frame does not code for human albumin, preferably the open reading frame does not code for albumin. It is preferred that the open reading frame does not code for a reporter protein, e.g., selected from the group consisting of globin proteins (particularly beta-globin), luciferase protein, GFP proteins or variants thereof, for example, variants exhibiting at least 70% sequence identity to a globin protein, a luciferase protein, or a GFP protein. Particularly, it is preferred, in a specific embodiment, that the open reading frame does not code for beta-globin, or, more specifically, for rabbit beta-globin, or variants thereof, in particular in case the 3'UTR element is derived from the rat albumin 3'UTR or variants thereof. Furthermore, in a specific embodiment, the artificial nucleic acid molecule of the invention does not code for a signal sequence (and therefore does not contain a segment coding for such a signal sequence), which is synonymously also designated a localization signal or targeting signal, Such a signal sequence is typically provided at the 5' terminus of the encoded amino acid sequence. Particularly, the artificial nucleic acid of the invention does not code for a protein which (artificially or naturally) contains a "signal amino acid sequence", in particular not a signal sequence directing the encoded protein to polysomes bound to the membrane of the endoplasmic reticulum and/or translocating the protein of interest encoded by the inventive nucleic acid across the membrane of the endoplasmic reticulum. In particular, the encoded protein of the inventive nucleic acid molecule does not contain an albumin signal sequence, more specifically not the rat albumin signal sequence. Typically, the protein encoded by the inventive artificial nucleic acid molecule does also not contain a milk protein or growth hormone signal sequence, in particular if the coding region codes for globin, more specifically for beta-globin, even more specifically for rabbit beta-globin. In another embodiment, the artificial nucleic acid sequence of the invention does not contain a globin 5'-UTR sequence, in particular not a 5'-UTR sequence from beta-globin or, more particularly, not a rabbit globin 5'-UTR sequence, in particular if the coding region codes for a globin sequence, more specifically for beta-globin or variants thereof. If the artificial nucleic acid molecule contains a 5'-UTR sequence, that 5'-UTR sequence may be selected such that it is not the 5'-UTR-sequence from an albumin gene, in particular not from the rat albumin gene. In case the artificial nucleic acid molecule of the invention contains more than one 3'-UTR, the other 3'-UTR(s) is/are preferably not selected from the group consisting of a globin 3'-UTR and a c-myc 3'-UTR. In another embodiment, the 3'UTR of the inventive nucleic acid molecule does not correspond to the rat albumin 3'-UTR, in particular if the coding region codes for a globin, more specifically a beta-globin.

Furthermore, it is particularly preferred that the open reading frame does not code for human factor IX or variants thereof, for example, variants exhibiting at least 70% sequence identity to human factor IX. The nucleic acid molecule does not contain an albumin promoter, in particular an albumin promoter with a point mutation, more specifically with a G52A point mutation, in particular if the coding region of the inventive nucleic acid molecule codes for human factor IX or variants thereof as described above.

In another embodiment, the artificial nucleic acid molecule of the invention does not correspond to a transposon element, e.g. a transposon plasmid, or does not contain a transposon (in particular not a Tn5 transposon or does not contain TN5 mosaic elements), in particular if the coding region codes for a resistance gene, in particular a neomycin resistance gene. The nucleic acid molecule of the invention cannot functionally interact with a transposase, in particular not with a Tn5 transposase, under such circumstances. Functionally speaking, the inventive nucleic acid molecule shall typically not form a complex between the nucleic acid (as the inventive artificial nucleic acid does not contain a transposon) and a transposase specific for whatever transposon. The coding region (ORF) of the nucleic acid molecule of the invention does not code for an siRNA, in particular if the nucleic acid molecule of the invention functionally interacts with a transposase.

In this context it is particularly preferred in a specific embodiment that the open reading frame does not contain an intron, particularly in case the open reading frame codes for human factor IX or variants thereof.

Furthermore, it is preferred in this context that in a specific embodiment the open reading frame does not code for human factor IX or variants thereof, in particular in case the 3'UTR element is derived from the human albumin 3'UTR or variants thereof.

The inventive artificial nucleic acid molecule is—as a specific embodiment of the invention—not an expression cassette. Accordingly, the inventive nucleic acid molecule does e.g. not contain a 3' promoter or a promoter 3' end. In terms of that embodiment, the inventive nucleic acid molecule is also not a "secretion cassette", as it does not contain a signal sequence and, preferably, does not contain 3' promoter. In particular, the inventive nucleic acid molecule is composed of one single nucleic acid molecule comprising the ORF and the 3'UTR region and optionally a 5' UTR region. Accordingly, the inventive nucleic acid molecule does not correspond to a secretion cassette which is composed of more than one separate genetic elements, in particular does not correspond to a first genetic element representing the region upstream of the coding region (ORF) and a separate second genetic element representing the region downstream of the ORF, which are provided independently, e.g. as parts of a kit.

Preferably, the at least one 3'UTR element is functionally linked to the ORF. This means preferably that the 3'UTR element is associated with the ORF such that it may exert a function, such as a stabilizing function on the expression of the ORF or a stabilizing function on the artificial nucleic acid molecule. Preferably, the ORF and the 3'UTR element are associated in 5'→3' direction. Thus, preferably, the artificial nucleic acid molecule comprises the structure 5'-ORF-(optional) linker-3'UTR element-3', wherein the linker may be present or absent. For example, the linker may be one or more nucleotides, such as a stretch of 1-50 or 1-20 nucleotides, e.g., comprising or consisting of one or more restriction enzyme recognition sites (restriction sites).

Preferably, the at least one 3'UTR element comprises or consists of a nucleic acid sequence which is derived from the 3'UTR of a vertebrate albumin gene or from a variant thereof, preferably from the 3'UTR of a mammalian albumin gene such as e.g. the 3'UTR of the mouse albumin gene, the albumin gene of Olive baboon or the human albumin gene or from a variant thereof. More preferably the at least one 3'UTR element comprises or consists of a nucleic acid sequence derived from the 3'UTR of a primate albumin gene, particularly of a human albumin gene or of an albumin gene of Olive baboon or from a variant thereof, even more preferably from the 3'UTR of the human albumin gene according to GenBank Accession number NM_000477.5 or from a variant thereof. In a preferred embodiment, the 3'UTR element is not derived from the 3'UTR of a *Xenopus* albumin gene. Preferably, the 3'UTR element does not comprise a poly(A) limiting element B (PLEB) of a 3'UTR from a *Xenopus* albumin gene. Preferably, the 3'UTR element does not consist of a PLEB of a 3'UTR from a *Xenopus* albumin gene.

The term "a nucleic acid sequence which is derived from the 3'UTR of an [ . . . ] albumin gene" preferably refers to a nucleic acid sequence which is based on the 3'UTR sequence of an albumin gene or on a fragment or part thereof. This term includes sequences corresponding to the entire 3'UTR sequence, i.e. the full length 3'UTR sequence of an albumin gene, and sequences corresponding to a fragment of the 3'UTR sequence of an albumin gene. Preferably, a fragment of a 3'UTR of an albumin gene consists of a continuous stretch of nucleotides corresponding to a continuous stretch of nucleotides in the full-length 3'UTR of an albumin gene, which represents at least 20%, preferably at least 30%, more preferably at least 40%, more preferably at least 50%, even more preferably at least 60%, even more preferably at least 70%, even more preferably at least 80%, and most preferably at least 90% of the full-length 3'UTR of an albumin gene. Such a fragment, in the sense of the present invention, is preferably a functional fragment as described herein. The term "3'UTR of an albumin gene" preferably refers to the 3'UTR of a naturally occurring albumin gene.

The terms "variant of the 3'UTR of an albumin gene" and "variant thereof" in the context of a 3'UTR of an albumin gene refers to a variant of the 3'UTR of a naturally occurring albumin gene, preferably to a variant of the 3'UTR of a vertebrate albumin gene, more preferably to a variant of the 3'UTR of a mammalian albumin gene such as the 3'UTR of a mouse albumin gene, even more preferably to a variant of the 3'UTR of a primate albumin gene, particular a human albumin gene or an albumin gene of Olive baboon as described above. Such variant may be a modified 3'UTR of an albumin gene. For example, a variant 3'UTR may exhibit one or more nucleotide deletions, insertions, additions and/or substitutions compared to the naturally occurring 3'UTR from which the variant is derived. Preferably, a variant of a 3'UTR of an albumin gene is at least 40%, preferably at least 50%, more preferably at least 60%, more preferably at least 70%, even more preferably at least 80%, even more preferably at least 90%, most preferably at least 95% identical to the naturally occurring 3'UTR the variant is derived from. Preferably, the variant is a functional variant as described herein.

The term "a nucleic acid sequence which is derived from a variant of the 3'UTR of an albumin gene" preferably refers to a nucleic acid sequence which is based on a variant of the 3'UTR sequence of an albumin gene or on a fragment or part thereof as described above. This term includes sequences corresponding to the entire sequence of the variant of the 3'UTR of an albumin gene, i.e. the full length variant 3'UTR sequence of an albumin gene, and sequences corresponding to a fragment of the variant 3'UTR sequence of an albumin gene. Preferably, a fragment of a variant of the 3'UTR of an albumin gene consists of a continuous stretch of nucleotides corresponding to a continuous stretch of nucleotides in the full-length variant of the 3'UTR of an albumin gene, which represents at least 20%, preferably at least 30%, more preferably at least 40%, more preferably at least 50%, even more preferably at least 60%, even more preferably at least 70%, even more preferably at least 80%, and most preferably at least 90% of the full-length variant of the 3'UTR of an albumin gene. Such a fragment of a variant, in the sense of the present invention, is preferably a functional fragment of a variant as described herein.

The terms "functional variant", "functional fragment", and "functional fragment of a variant" (also termed "functional variant fragment") in the context of the present invention, mean that the fragment of the 3'UTR, the variant of the 3'UTR, or the fragment of a variant of the 3'UTR of an albumin gene fulfils at least one, preferably more than one function of the naturally occurring 3'UTR of an albumin gene of which the variant, the fragment, or the fragment of a variant is derived. Such function may be, for example, stabilizing mRNA and/or stabilizing and/or prolonging protein production from an mRNA and/or increasing protein expression or total protein production from an mRNA, preferably in a mammalian cell, such as in a human cell. It is particularly preferred that the variant, the fragment, and the variant fragment in the context of the present invention fulfil the function of stabilizing an mRNA, preferably in a mammalian cell, such as a human cell, compared to an mRNA comprising a reference 3'UTR or lacking a 3'UTR, and/or the function of stabilizing and/or prolonging protein production from an mRNA, preferably in a mammalian cell, such as in a human cell, compared to an mRNA comprising a reference 3'UTR or lacking a 3'UTR, and/or the function of increasing protein production from an mRNA, preferably in a mammalian cell, such as in a human cell, compared to an mRNA comprising a reference 3'UTR or lacking a 3'UTR. A reference 3'UTR may be, for example, a 3'UTR naturally occurring in combination with the ORF. Furthermore, a functional variant, a functional fragment, or a functional variant fragment of a 3'UTR of an albumin gene preferably does not have a substantially diminishing effect on the efficiency of translation of the mRNA which comprises such variant, fragment, or variant fragment of a 3'UTR compared to the wild type 3'UTR from which the variant, the fragment, or the variant fragment is derived. A particularly preferred function of a "functional fragment", a "functional variant" or a "functional fragment of a variant" of the 3'UTR of an albumin gene in the context of the present invention is the stabilization and/or prolongation of protein production by expression of an mRNA carrying the functional fragment, functional variant or functional fragment of a variant as described above.

Preferably, the efficiency of the one or more functions exerted by the functional variant, the functional fragment, or the functional variant fragment, such as mRNA and/or protein production stabilizing efficiency and/or the protein production increasing efficiency, is at least 40%, more preferably at least 50%, more preferably at least 60%, even more preferably at least 70%, even more preferably at least 80%, most preferably at least 90% of the mRNA and/or protein production stabilizing efficiency and/or the protein production increasing efficiency exhibited by the naturally occurring 3'UTR of an albumin gene from which the variant, the fragment or the variant fragment is derived.

In the context of the present invention, a fragment of the 3'UTR of an albumin gene or of a variant of the 3'UTR of an albumin gene preferably exhibits a length of at least about 50 nucleotides, preferably of at least about 75 nucleotides, more preferably of at least about 100 nucleotides, even more preferably of at least about 125 nucleotides, most preferably of at least about 150 nucleotides. Preferably, such fragment of the 3'UTR of an albumin gene or of a variant of the 3'UTR of an albumin gene is a functional fragment as described above.

Preferably, the at least one 3'UTR element of the artificial nucleic acid molecule according to the present invention comprises or consists of a "functional fragment", a "functional variant" or a "functional fragment of a variant" of the 3'UTR of an albumin gene.

Preferably, the at least one 3'UTR element of the artificial nucleic acid molecule according to the present invention increases the stability of the artificial nucleic acid molecule, e.g. increases the stability of an mRNA according to the present invention, compared to a respective mRNA (reference mRNA) lacking a 3'UTR or comprising a reference 3'UTR, such as a 3'UTR naturally occurring in combination with the ORF. Preferably, the at least one 3'UTR element of the artificial nucleic acid molecule according to the present invention increases the stability of protein production from the artificial nucleic acid molecule according to the present invention, e.g. from an mRNA according to the present invention, compared to a respective mRNA lacking a 3'UTR or comprising a reference 3'UTR, such as a 3'UTR naturally occurring in combination with the ORF. Preferably, the at least one 3'UTR element of the artificial nucleic acid molecule according to the present invention prolongs protein production from the artificial nucleic acid molecule according to the present invention, e.g. from an mRNA according to the present invention, compared to a respective mRNA lacking a 3'UTR or comprising a reference 3'UTR, such as a 3'UTR naturally occurring in combination with the ORF. Preferably, the at least one 3'UTR element of the artificial nucleic acid molecule according to the present invention increases the protein expression and/or total protein production from the artificial nucleic acid molecule according to the present invention, e.g. from an mRNA according to the present invention, compared to a respective mRNA lacking a 3'UTR or comprising a reference 3'UTR, such as a 3'UTR naturally occurring in combination with the ORF. Preferably, the at least one 3'UTR element of the artificial nucleic acid molecule according to the present invention does not negatively influence translational efficiency of an mRNA compared to the translational efficiency of a respective mRNA lacking a 3'UTR or comprising a reference 3'UTR, such as a 3'UTR naturally occurring in combination with the ORF. The term "respective mRNA" in this context means that—apart from the different 3'UTRs—the reference mRNA is comparable, preferably identical, to the mRNA comprising the inventive 3'UTR element.

The term "stabilizing and/or prolonging protein production" from an artificial nucleic acid molecule such as an artificial mRNA preferably means that the protein production from the artificial nucleic acid molecule such as the artificial mRNA is stabilized and/or prolonged compared to the protein production from a reference nucleic acid molecule such as a reference mRNA, e.g. comprising a reference 3'UTR or lacking a 3'UTR, preferably in a mammalian expression system, such as in HeLa or HDF cells. Thus, protein produced from the artificial nucleic acid molecule such as the artificial mRNA is observable for a longer period of time than what may be seen for a protein produced from a reference nucleic acid molecule. In other words, the amount of protein produced from the artificial nucleic acid molecule such as the artificial mRNA measured over time undercuts a threshold value at a later time point than the amount of protein produced from a reference nucleic acid molecule such as a reference mRNA measured over time. Such a threshold value may be, for example, the amount of protein measured in the initial phase of expression, such as 1, 2, 3, 4, 5, or 6 hours post initiation of expression, such as post transfection of the nucleic acid molecule (FIG. 17).

For example, the protein production from the artificial nucleic acid molecule such as the artificial mRNA—in an amount which is at least the amount observed in the initial phase of expression, such as 1, 2, 3, 4, 5, or 6 hours post initiation of expression, such as post transfection of the nucleic acid molecule—is prolonged by at least about 5 hours, preferably by at least about 10 hours, more preferably by at least about 24 hours compared to the protein production from a reference nucleic acid molecule, such as a reference mRNA, in a mammalian expression system, such as in mammalian cells, e.g. in HeLa or HDF cells. Thus, the artificial nucleic acid molecule according to the present invention preferably allows for prolonged protein production in an amount which is at least the amount observed in the initial phase of expression, such as 1, 2, 3, 4, 5, or 6 hours post initiation of expression, such as post transfection, by at least about 5 hours, preferably by at least about 10 hours, more preferably by at least about 24 hours compared to a reference nucleic acid molecule lacking a 3'UTR or comprising a reference 3'UTR.

In preferred embodiments, the protein production from the artificial nucleic acid molecule according to the present invention is prolonged at least 1.5 fold, preferably at least 2 fold, more preferably at least 2.5 fold compared to the protein production from a reference nucleic acid molecule lacking a 3'UTR or comprising a reference 3'UTR.

This effect of prolonging protein production may be determined by (i) measuring protein amounts, e.g. obtained by expression of an ORF encoding a reporter protein such as luciferase, preferably in a mammalian expression system such as in HeLa or HDF cells, over time, (ii) determining the time point at which the protein amount undercuts the amount of protein observed, e.g., at 1, 2, 3, 4, 5, or 6 hours post initiation of expression, e.g. 1, 2, 3, 4, 5, or 6 hours post transfection of the artificial nucleic acid molecule, and (iii) comparing the time point at which the protein amount undercuts the protein amount observed at 1, 2, 3, 4, 5, or 6 hours post initiation of expression to said time point determined for a nucleic acid molecule lacking a 3'UTR or comprising a reference 3'UTR (FIG. 17).

Preferably, this stabilizing and/or prolonging effect on protein production is achieved, while the total amount of protein produced from the artificial nucleic acid molecule according to the present invention, e.g. within a time span of 48 or 72 hours, is at least the amount of protein produced from a reference nucleic acid molecule lacking a 3'UTR or comprising a reference 3'UTR, such as a 3'UTR naturally occurring with the ORF of the artificial nucleic acid molecule. Thus, the present invention provides an artificial nucleic acid molecule which allows for prolonged and/or stabilized protein production in a mammalian expression system, such as in mammalian cells, e.g. in HeLa or HDF cells, as specified above, wherein the total amount of protein produced from said artificial nucleic acid molecule, e.g. within a time span of 48 or 72 hours, is at least the total amount of protein produced, e.g. within said time span, from a reference nucleic acid molecule lacking a 3'UTR or comprising a reference 3'UTR, such as a 3'UTR naturally occurring with the ORF of the artificial nucleic acid molecule.

Thus, "stabilized protein expression" preferably means that there is more uniform protein production from the artificial nucleic acid molecule according to the present invention over a predetermined period of time, such as over 24 hours, more preferably over 48 hours, even more preferably over 72 hours, when compared to a reference nucleic acid molecule, for example, an mRNA comprising a reference 3'UTR or lacking a 3'UTR. Accordingly, the level of protein production, e.g. in a mammalian system, from the artificial nucleic acid molecule comprising a 3'UTR element according to the present invention, e.g. from an mRNA according to the present invention, preferably does not drop to the extent observed for a reference nucleic acid molecule, such as a reference mRNA as described above. For example, the amount of a protein (encoded by the ORF) observed 6 hours after initiation of expression, e.g. 6 hours post transfection of the artificial nucleic acid molecule according to the present invention into a cell, such as a mammalian cell, may be comparable to the amount of protein observed 48 hours after initiation of expression, e.g. 48 hours post transfection. Thus, the ratio of the amount of protein encoded by the ORF, such as of a reporter protein, e.g., luciferase, observed at 48 hours post initiation of expression, e.g. 48 hours post transfection, to the amount of protein observed 6 hours after initiation of expression, e.g. 6 hours post transfection, is preferably at least about 0.4, more preferably at least about 0.5, more preferably at least about 0.6, even more preferably at least about 0.7. Preferably, the ratio is between about 0.4 and about 4, preferably between about 0.65 and about 3, more preferably between about 0.7 and 2 for a nucleic acid molecule according to the present invention. For a respective reference nucleic acid molecule, e.g. an mRNA comprising a reference 3'UTR or lacking a 3'UTR, said ratio may be, e.g. between about 0.05 and about 0.3.

Thus, the present invention provides an artificial nucleic acid molecule comprising an ORF and a 3'UTR element as described above, wherein the ratio of the (reporter) protein amount, e.g. the amount of luciferase, observed 48 hours after initiation of expression to the (reporter) protein amount observed 6 hours after initiation of expression, preferably in a mammalian expression system, such as in mammalian cells, e.g. in HeLa cells, is preferably above about 0.4, more preferably above about 0.5, more preferably above about 0.6, even more preferably above about 0.7, e.g. between about 0.4 and about 4, preferably between about 0.65 and about 3, more preferably between about 0.7 and 2, wherein preferably the total amount of protein produced from said artificial nucleic acid molecule, e.g. within a time span of 48 hours, is at least the total amount of protein produced, e.g. within said time span, from a reference nucleic acid molecule lacking a 3'UTR or comprising a reference 3'UTR, such as a 3'UTR naturally occurring with the ORF of the artificial nucleic acid molecule. In a preferred embodiment, the present invention provides an artificial nucleic acid molecule comprising an ORF and a 3'UTR element as described above, wherein the ratio of the (reporter) protein amount, e.g. the amount of luciferase, observed 72 hours after initiation of expression to the (reporter) protein amount observed 6 hours after initiation of expression, preferably in a mammalian expression system, such as in mammalian cells, e.g. in HeLa cells, is preferably above about 0.4, more preferably above about 0.5, more preferably above about 0.6, even more preferably above about 0.7, e.g. between about 0.4 and 1.5, preferably between about 0.65 and about 1.15, more preferably between about 0.7 and 1.0, wherein preferably the total amount of protein produced from said artificial nucleic acid molecule, e.g. within a time span of 72 hours, is at least the total amount of protein produced, e.g. within said time span, from a reference nucleic acid molecule lacking a 3'UTR or comprising a reference 3'UTR, such as a 3'UTR naturally occurring with the ORF of the artificial nucleic acid molecule.

"Increased protein expression" in the context of the present invention preferably means an increased protein expression at one time point after initiation of expression compared to a reference molecule. Thus, the protein level observed at a certain time point after initiation of expression, e.g. after transfection, of the artificial nucleic acid molecule according to the present invention, e.g. after transfection of an mRNA according to the present invention, for example, 48 or 72 hours post transfection, is preferably higher than the protein level observed at the same time point after initiation of expression, e.g. after transfection, of a reference nucleic acid molecule, such as a reference mRNA comprising a reference 3'UTR or lacking a 3'UTR.

"Increased total protein production" from an artificial nucleic acid molecule refers to an increased protein production over the time span, in which protein is produced from an artificial nucleic acid molecule, preferably in a mammalian expression system, such as in mammalian cells, e.g. in HeLa or HDF cells. Thus, "total protein production" preferably refers to the area under the curve (AUC) representing protein production over time.

Said increase in stability of the artificial nucleic acid molecule, said increase in stability of protein production, said prolongation of protein production and/or said increase in protein expression and/or total protein production is preferably determined by comparison with a respective reference nucleic acid molecule lacking a 3'UTR, e.g. an mRNA lacking a 3'UTR, or a reference nucleic acid molecule comprising a reference 3'UTR, such as a 3'UTR naturally occurring with the ORF as describe above.

The mRNA and/or protein production stabilizing effect and efficiency and/or the protein production increasing effect and efficiency of the variants, fragments and/or variant fragments of the 3'UTR of an albumin gene as well as the mRNA and/or protein production stabilizing effect and efficiency and/or the protein production increasing effect and efficiency of the at least one 3'UTR element of the artificial nucleic acid molecule according to the present invention may be determined by any method suitable for this purpose known to skilled person. For example, artificial mRNA molecules may be generated comprising a coding sequence for a reporter protein, such as luciferase, and no 3'UTR, a 3'UTR derived from a naturally occurring albumin gene, a 3'UTR derived from a reference gene (i.e., a reference 3'UTR, such as a 3'UTR naturally occurring with the ORF), as 3'UTR a variant of a 3'UTR of an albumin gene, as 3'UTR a fragment of a naturally occurring albumin gene, or as 3'UTR a fragment of a variant of a 3'UTR of an albumin gene. Such mRNAs may be generated, for example, by in vitro transcription of respective vectors such as plasmid vectors, e.g. comprising a T7 promoter and a sequence encoding the respective mRNA sequences. The generated mRNA molecules may be transfected into cells by any transfection method suitable for transfecting mRNA, for example they may be electroporated into mammalian cells, such as HELA cells, and samples may be analyzed certain time points after transfection, for example, 6 hours, 24 hours, 48 hours, and 72 hours post transfection. Said samples may be analyzed for mRNA quantities and/or protein quantities by methods well known to the skilled person. For example, the quantities of reporter mRNA present in the cells at the sample time points may be determined by quantitative PCR methods. The quantities of reporter protein encoded by the respective mRNAs may be determined, e.g., by ELISA assays or reporter assays such as luciferase assays depending on the reporter protein used. The effect of stabilizing protein expression and/or prolonging protein expression may be, for example, analyzed by determining the ratio of the protein level observed 48 hours post transfection and the protein level observed 6 hours post transfection. The closer said value is to 1, the more stable the protein expression is within this time period. Such measurements may of course also be performed at 72 or more hours and the ratio of the protein level observed 72 hours post transfection and the protein level observed 6 hours post transfection may be determined to determine stability of protein expression.

Preferably, the at least one 3'UTR element of the artificial nucleic acid molecule according to the present invention comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of a 3'UTR of an albumin gene, such as to the nucleic acid sequence according to SEQ ID No. 1, SEQ ID No. 2, SEQ ID No. 32, SEQ ID No. 33, SEQ ID No. 34 or SEQ ID No. 35 as shown below, wherein the variants of the sequences (e.g. at least 40% identical) are preferably functional variants as described above:

```
                                                           (SEQ ID No. 1)
CATCACATTT AAAAGCATCT CAGCCTACCA TGAGAATAAG AGAAAGAAAA TGAAGATCAA

AAGCTTATTC ATCTGTTTTT CTTTTTCGTT GGTGTAAAGC CAACACCCTG TCTAAAAAAC

ATAAATTTCT TTAATCATTT TGCCTCTTTT CTCTGTGCTT CAATTAATAA AAATGGAAA

GAATCT (SEQ ID No. 2)
CAUCACAUUU AAAAGCAUCU CAGCCUACCA UGAGAAUAAG AGAAAGAAAA UGAAGAUCAA

AAGCUUAUUC AUCUGUUUUU CUUUUUCGUU GGUGUAAAGC CAACACCCUG UCUAAAAAAC

AUAAAUUUCU UUAAUCAUUU UGCCUCUUUU CUCUGUGCUU CAAUUAAUAA AAAUGGAAA

GAAUCU.

(SEQ ID No. 32)
AAACATCACA ATTAAGAACA TCTCAGCCTA CCATGAGAAC AAGAGAAATA AAATGAAGAT

CAAAAGCTTA TTCATCTGTT TTTCTTTTTC ATTGGTATAA AGCCAACACC CTGTCTAAAA

AACTATAAAT TTCTTTAATC ATTTTGCCTC TTTTCTCTGT GCTTCAATTA ATAAAAAATG

GAAAGAATCT AGATCTAAAA AAAAAAAAAA AAAAAAAAAA AAAAAAAAAA AAAAAAAAAA

AAAA (SEQ ID No. 33)
AAACAUCACA AUUAAGAACA UCUCAGCCUA CCAUGAGAAC AAGAGAAAUA AAAUGAAGAU

CAAAAGCUUA UUCAUCUGUU UUUCUUUUUC AUUGGUAUAA AGCCAACACC CUGUCUAAAA

AACUAUAAAU UUCUUUAAUC AUUUUGCCUC UUUUCUCUGU GCUUCAAUUA AUAAAAAAUG

GAAAGAAUCU AGAUCUAAAA AAAAAAAAAA AAAAAAAAAA AAAAAAAAAA AAAAAAAAAA

AAAA (SEQ ID No. 34)
ACACATCACA ACCACAACCT TCTCAGGCTA CCCTGAGAAA AAAAGACATG AAGACTCAGG

ACTCATCTTT TCTGTTGGTG TAAAATCAAC ACCCTAAGGA ACACAAATTT CTTTAAACAT

TTGACTTCTT GTCTCTGTGC TGCAATTAAT AAAAAATGGA AGAATCTAC AGATCTAAAA

AAAA (SEQ ID No. 35)
ACACAUCACA ACCACAACCU UCUCAGGCUA CCCUGAGAAA AAAAGACAUG AAGACUCAGG

ACUCAUCUUU UCUGUUGGUG UAAAAUCAAC ACCCUAAGGA ACACAAAUUU CUUUAAACAU

UUGACUUCUU GUCUCUGUGC UGCAAUUAAU AAAAAAUGGA AGAAUCUAC AGAUCUAAAA

AAAA
```

The at least one 3'UTR element of the artificial nucleic acid molecule according to the present invention may also comprise or consist of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of the 3'UTR of an albumin gene, such as to the nucleic acid sequence according to SEQ ID No. 1, SEQ ID No. 2, SEQ ID No. 32, SEQ ID No. 33, SEQ ID No. 34 or SEQ ID No. 35, wherein the fragment is preferably a functional fragment or a functional variant fragment as described above. Such fragment preferably exhibits a length of at least about 50 nucleotides, preferably of at least about 75 nucleotides, more preferably of at least about 100 nucleotides, even more preferably of at least about 125 nucleotides, most preferably of at least about 150 nucleotides.

For example, such fragment may exhibit a nucleic acid sequence according to SEQ ID Nos. 18-30, such as

```
                                                       (SEQ ID No. 18)
AAAAGCATCT CAGCCTACCA TGAGAATAAG AGAAAGAAAA TGAAGATCAA AAGCTTATTC

ATCTGTTTTT CTTTTTCGTT GGTGTAAAGC CAACACCCTG TCTAAAAAAC ATAAATTTCT

TTAATCATTT TGCCTCTTTT CTCTGTGCTT CAATT (SEQ ID No. 19)
CATCACATTT AAAAGCATCT CAGCCTACCA TGAGAATAAG AGAAAGAAAA TGAAGATCAA

AAGCTTATTC ATCTGTTTTT CTTTTTCGTT GGTGTAAAGC CAACACCCTG (SEQ ID No. 20)
AAAAGCATCT CAGCCTACCA TGAGAATAAG AGAAAGAAAA TGAAGATCAA AAGCTTATTC

ATCTGTTTTT CTTTTTCGTT GGTGTAAAGC CAACACCCTG TCTAAAAAAC (SEQ ID No. 21)
CAGCCTACCA TGAGAATAAG AGAAAGAAAA TGAAGATCAA AAGCTTATTC ATCTGTTTTT

CTTTTTCGTT GGTGTAAAGC CAACACCCTG TCTAAAAAAC ATAAATTTCT (SEQ ID No. 22)
TGAGAATAAG AGAAAGAAAA TGAAGATCAA AAGCTTATTC ATCTGTTTTT CTTTTTCGTT

GGTGTAAAGC CAACACCCTG TCTAAAAAAC ATAAATTTCT TTAATCATTT (SEQ ID No. 23)
AGAAAGAAAA TGAAGATCAA AAGCTTATTC ATCTGTTTTT CTTTTTCGTT GGTGTAAAGC

CAACACCCTG TCTAAAAAAC ATAAATTTCT TTAATCATTT TGCCTCTTTT (SEQ ID No. 24)
TGAAGATCAA AAGCTTATTC ATCTGTTTTT CTTTTTCGTT GGTGTAAAGC CAACACCCTG

TCTAAAAAAC ATAAATTTCT TTAATCATTT TGCCTCTTTT CTCTGTGCTT (SEQ ID No. 25)
AAGCTTATTC ATCTGTTTTT CTTTTTCGTT GGTGTAAAGC CAACACCCTG TCTAAAAAAC

ATAAATTTCT TTAATCATTT TGCCTCTTTT CTCTGTGCTT CAATTAATAA (SEQ ID No. 26)
ATCTGTTTTT CTTTTTCGTT GGTGTAAAGC CAACACCCTG TCTAAAAAAC ATAAATTTCT

TTAATCATTT TGCCTCTTTT CTCTGTGCTT CAATTAATAA AAAATGGAAA (SEQ ID No. 27)
CAGCCTACCA TGAGAATAAG AGAAAGAAAA TGAAGATCAA AAGCTTATTC ATCTGTTTTT

CTTTTTCGTT GGTGTAAAGC CAACACCCTG TCTAAAAAAC ATAAATTTCT TTAATCATTT

TGCCTCTTTT CTCTGTGCTT CAATTAATAA A (SEQ ID No. 28)
TGAAGATCAA AAGCTTATTC ATCTGTTTTT CTTTTTCGTT GGTGTAAAGC CAACACCCTG

TCTAAAAAAC ATAAATTTCT TTAATCATTT TGCCTCTTTT CTCTGTGCTT CAATTAATAA

A (SEQ ID No. 29)
CTTTTTCGTT GGTGTAAAGC CAACACCCTG TCTAAAAAAC ATAAATTTCT TTAATCATTT

TGCCTCTTTT CTCTGTGCTT CAATTAATAA A (SEQ ID No. 30)
AAGCTTATTC ATCTGTTTTT CTTTTTCGTT GGTGTAAAGC CAACACCCTG TCTAAAAAAC
``` or the corresponding RNA sequence, or a nucleic acid sequence which is at least 40%, preferably at least about 50%, preferably at least about 60%, preferably at least about 70%, more preferably at least about 80%, more preferably at least about 90%, even more preferably at least about 95%, even more preferably at least about 99% identical to said nucleic acid sequences or the corresponding RNA sequence. Thus, the at least one 3'UTR element of the artificial nucleic acid molecule according to the present invention may comprise of consist of a nucleic acid fragment as described above. Obviously, the thymidine nucleotides comprised in the fragments according to SEQ ID No. 18-30 can be replaced by uridine nucleotides.

Preferably, said variants, fragments or variant fragments are functional variants, functional fragments, or functional variant fragments as described above, exhibiting at least one function of the nucleic acid sequence according to SEQ ID No. 1,SEQ ID No. 2, SEQ ID No. 32, SEQ ID No. 33, SEQ ID No. 34 or SEQ ID No. 35, such as stabilization of the artificial nucleic acid molecule according to the invention, stabilizing and/or prolonging protein expression from the artificial nucleic acid molecule according to the invention, and/or increasing protein production, preferably with an efficiency of at least 40%, more preferably of at least 50%, more preferably of at least 60%, even more preferably of at least 70%, even more preferably of at least 80%, most preferably of at least 90% of the stabilizing efficiency and/or protein production increasing efficiency exhibited by the nucleic acid sequence according to SEQ ID No. 1,SEQ ID NO. 2, SEQ ID No. 32, SEQ ID No. 33, SEQ ID No. 34 or SEQ ID No. 35.

Preferably, the at least one 3'UTR element of the artificial nucleic acid molecule according to the present invention exhibits a length of at least about 50 nucleotides, preferably of at least about 75 nucleotides, more preferably of at least about 100 nucleotides, even more preferably of at least about 125 nucleotides, most preferably of at least about 150 nucleotides. For example, the 3'UTR element may exhibit a length of about 50 to about 300 nucleotides, preferably of about 100 to about 250 nucleotides, more preferably of about 150 to about 200 nucleotides.

Furthermore, the artificial nucleic acid molecule according to the present invention may comprise more than one 3'UTR elements as described above. For example, the artificial nucleic acid molecule according to the present invention may comprise one, two, three, four or more 3'UTR elements, wherein the individual 3'UTR elements may be the same or they may be different. For example, the artificial nucleic acid molecule according to the present invention may comprise two essentially identical 3'UTR elements as described above, e.g. two 3'UTR elements comprising or consisting of a nucleic acid sequence which is derived from the 3'UTR of an albumin gene or from a variant of the 3'UTR of an albumin gene, such as a nucleic acid sequence according to SEQ ID No. 1,2, 32, 33, 34 or 35 functional variants thereof, functional fragments thereof, or functional variant fragments thereof as described above.

Surprisingly, the inventors found that an artificial nucleic acid molecule comprising a 3'UTR as described above may represent or may provide an mRNA molecule which allows for prolonged and/or stabilized protein production. Thus, a 3'UTR as described herein may improve stability of protein expression from an mRNA molecule and/or improve translational efficiency.

The artificial nucleic acid molecule according to the present invention may be RNA, such as mRNA, DNA, such as a DNA vector, or may be a modified RNA or DNA molecule. It may be provided as a double-stranded molecule having a sense strand and an anti-sense strand, for example, as a DNA molecule having a sense strand and an anti-sense strand.

The artificial nucleic acid according to the present invention may further comprise optionally a 5'UTR and/or a 5'-cap. The optional 5'-cap and/or the 5'UTR are preferably located 5' to the ORF within the artificial nucleic acid molecule according to the present invention.

Preferably, the artificial nucleic acid molecule according to the present invention further comprises a poly(A) sequence and/or a polyadenylation signal. Preferably, the optional poly(A) sequence is located 3' to the at least one 3'UTR element, preferably is connected to the 3'-end of the 3'UTR element. The connection may be direct or indirect, for example, via a stretch of 2, 4, 6, 8, 10, 20 etc. nucleotides, such as via a linker of 1-50, preferably of 1-20 nucleotides, e.g. comprising or consisting of one or more restriction sites.

In one embodiment, the optional polyadenylation signal is located within the 3'UTR element. Preferably, the polyadenylation signal comprises the consensus sequence NN(U/T)ANA, with N=A or U, preferably AA(U/T)AAA or A(U/T)(U/T)AAA. Such consensus sequence may be recognised by most animal and bacterial cell-systems, for example by the polyadenylation-factors, such as cleavage/polyadenylation specificity factor (CPSF) cooperating with CstF, PAP, PAB2, CFI and/or CFII. Preferably, the polyadenylation signal, preferably the consensus sequence NNUANA, is located less than about 50 nucleotides, more preferably less than about 30 bases, most preferably less than about 25 bases, for example 21 bases, upstream of the 3'-end of the 3'UTR element.

Transcription of an artificial nucleic acid molecule according to the present invention, e.g. of an artificial DNA molecule, comprising a polyadenylation signal within the 3'UTR element will result in a premature-RNA containing the polyadenylation signal in its 3'UTR element. For example, transcription of a DNA molecule comprising a 3'UTR element according to SEQ ID No. 1

```
                                            (SEQ ID No. 1)
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCT
``` will result in an RNA having a 3'UTR element according to the sequence

```
                                            (SEQ ID No. 2)
CAUCACAUUU AAAAGCAUCU CAGCCUACCA UGAGAAUAAG

AGAAAGAAAA UGAAGAUCAA AAGCUUAUUC AUCUGUUUUU

CUUUUUCGUU GGUGUAAAGC CAACACCCUG UCUAAAAAAC

AUAAAUUUCU UUAAUCAUUU UGCCUCUUUU CUCUGUGCUU

CAAUUAAUAA AAAAUGGAAA GAAUCU.
```

Using an appropriate transcription system will then lead to attachment of a poly(A) sequence to the premature-RNA. For example, the inventive artificial nucleic acid molecule may be a DNA molecule comprising a 3'UTR element as described above and a polyadenylation signal, which may result in polyadenylation of an RNA upon transcription of this DNA molecule. Accordingly, a resulting RNA may comprise a combination of the inventive 3'UTR element followed by a poly(A) sequence.

Potential transcription systems are in vitro transcription systems or cellular transcription systems etc. Accordingly, transcription of an artificial nucleic acid molecule according to the invention, e.g. transcription of an artificial nucleic acid molecule comprising an open reading frame, a 3'UTR element and a polyadenylation-signal, may result in an mRNA molecule comprising an open reading frame, a 3'UTR element and a poly(A) sequence.

Accordingly, the invention also provides an artificial nucleic acid molecule which is an mRNA molecule comprising an open reading frame, a 3'UTR element as described above and a poly(A) sequence.

In one embodiment, the invention provides an artificial nucleic acid molecule which is an artificial DNA molecule comprising an open reading frame and a sequence according to SEQ ID No. 1 or a sequence having an identity of at least about 40% or more to SEQ ID No. 1 or a fragment thereof as described above. Furthermore, the invention provides an artificial nucleic acid molecule which is an artificial RNA molecule comprising an open reading frame and a sequence according to SEQ ID NO. 2 or a sequence having an identity of at least about 40% or more to SEQ ID No. 2 or a fragment thereof as described above.

In one further embodiment, the invention provides an artificial nucleic acid molecule which is an artificial DNA molecule comprising an open reading frame and a sequence according to SEQ ID No. 32 or a sequence having an identity of at least about 40% or more to SEQ ID No. 32 or a fragment thereof as described above. Furthermore, the invention provides an artificial nucleic acid molecule which is an artificial RNA molecule comprising an open reading frame and a sequence according to SEQ ID NO. 33 or a sequence having an identity of at least about 40% or more to SEQ ID No. 33 or a fragment thereof as described above.

Furthermore, the invention provides an artificial nucleic acid molecule which is an artificial DNA molecule comprising an open reading frame and a sequence according to SEQ ID No. 34 or a sequence having an identity of at least about 40% or more to SEQ ID No. 34 or a fragment thereof as described above. Furthermore, the invention provides an artificial nucleic acid molecule which is an artificial RNA molecule comprising an open reading frame and a sequence according to SEQ ID NO. 35 or a sequence having an identity of at least about 40% or more to SEQ ID No. 35 or a fragment thereof as described above.

Accordingly, the invention provides an artificial nucleic acid molecule which may be a template for an RNA molecule, preferably for an mRNA molecule, which is stabilised and optimized with respect to translation efficiency. In other words, the artificial nucleic acid molecule may be a DNA or RNA which may be used for production of an mRNA. The obtainable mRNA, may, in turn, be translated for production of a desired peptide or protein encoded by the open reading frame. If the artificial nucleic acid molecule is a DNA, it may, for example, be used as a double-stranded storage form for continued and repetitive in vitro or in vivo production of mRNA.

In one embodiment, the artificial nucleic acid molecule according to the present invention further comprises a poly(A) sequence. The length of the poly(A) sequence may vary. For example, the poly(A) sequence may have a length of about 20 adenine nucleotides up to about 300 adenine nucleotides, preferably of about 40 to about 200 adenine nucleotides, more preferably from about 50 to about 100 adenine nucleotides, such as about 60, 70, 80, 90 or 100 adenine nucleotides.

For example, the artificial nucleic acid molecule according to the present invention may comprise a nucleic acid sequence corresponding to the DNA-sequences

```
                                          (SEQ ID No. 3)
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCTAGAT CTAAAAAAAA

AAAAAAAAAA AAAAAAAAAA AAAAAAAAAA AAAAAAAAAA

AAAAAAAAAA AAAAAA, (SEQ ID No. 36)
AAACATCACA ATTAAGAACA TCTCAGCCTA CCATGAGAAC

AAGAGAAATA AAATGAAGAT CAAAAGCTTA TTCATCTGTT

TTTCTTTTTC ATTGGTATAA AGCCAACACC CTGTCTAAAA

AACTATAAAT TTCTTTAATC ATTTTGCCTC TTTTCTCTGT

GCTTCAATTA ATAAAAAATG GAAAGAATCT AGATCTAAAA

AAAAAAAAAA AAAAAAAAAA AAAAAAAAAA AAAAAAAAAA

AAAAAAAAAA AAAAAAAAAA
or
                                         (SEQ ID No. 38)
ACACATCACA ACCACAACCT TCTCAGGCTA CCCTGAGAAA

AAAAGACATG AAGACTCAGG ACTCATCTTT TCTGTTGGTG

TAAAATCAAC ACCCTAAGGA ACACAAATTT CTTTAAACAT

TTGACTTCTT GTCTCTGTGC TGCAATTAAT AAAAAATGGA

AAGAATCTAC AGATCTAAAA AAAAAAAAAA AAAAAAAAA

AAAAAAAAAA AAAAAAAAAA AAAAAAAAAA AAAAAAAAAA
```

Transcription of such sequences may result in artificial nucleic acid molecules comprising the sequences

```
                                          (SEQ ID No. 4)
CAUCACAUUU AAAAGCAUCU CAGCCUACCA UGAGAAUAAG

AGAAAGAAAA UGAAGAUCAA AAGCUUAUUC AUCUGUUUUU

CUUUUUCGUU GGUGUAAAGC CAACACCCUG UCUAAAAAAC

AUAAAUUUCU UUAAUCAUUU UGCCUCUUUU CUCUGUGCUU

CAAUUAAUAA AAAAUGGAAA GAAUCUAGAU CUAAAAAAAA

AAAAAAAAAA AAAAAAAAAA AAAAAAAAAA AAAAAAAAAA

AAAAAAAAAA AAAAAA, (SEQ ID No. 37)
AAACAUCACA AUUAAGAACA UCUCAGCCUA CCAUGAGAAC

AAGAGAAAUA AAAUGAAGAU CAAAAGCUUA UUCAUCUGUU

UUUCUUUUUC AUUGGUAUAA AGCCAACACC CUGUCUAAAA
```

-continued

```
AACUAUAAAU UUCUUUAAUC ATTTTGCCTC TTTTCTCTGT

GCTTCAATTA ATAAAAAATG GAAAGAATCT AGATCTAAAA

AAAAAAAAAA AAAAAAAAAA AAAAAAAAAA AAAAAAAAAA

AAAAAAAAAA AAAAAAAAA
or
                                       (SEQ ID No. 39)
ACACAUCACA ACCACAACCU UCUCAGGCUA CCCUGAGAAA

AAAAGACAUG AAGACUCAGG ACUCAUCUUU UCUGUUGGUG

UAAAAUCAAC ACCCUAAGGA ACACAAAUUU CUUUAAACAU

UUGACUUCUU GUCUCUGUGC UGCAAUUAAU AAAAAAUGGA

AAGAAUCUAC AGAUCUAAAA AAAAAAAAAA AAAAAAAAAA

AAAAAAAAAA AAAAAAAAAA AAAAAAAAAA AAAAAAAAAA
```

Such artificial RNA-molecules, i.e. artificial nucleic acid molecules comprising a sequence according to SEQ ID No. 4, 37 or 39 may also be obtainable in vitro by common methods of chemical-synthesis without being necessarily transcribed from a DNA-progenitor.

In a particularly preferred embodiment, the artificial nucleic acid molecule according to the present invention is an RNA molecule, preferably an mRNA molecule comprising in 5'-to-3'-direction an open reading frame, a 3'UTR element as described above and a poly(A) sequence.

In a preferred embodiment, the open reading frame does not code for albumin, particularly not for human albumin, mouse albumin or albumin from Olive baboon, provided that the 3'UTR element is identical to the 3'UTR of human albumin, mouse albumin or albumin from Olive baboon, respectively. In some further embodiments, it may be preferred if the open reading frame does not code for human albumin according to GenBank Accession number NM_000477.5 provided that the 3'UTR element is identical to the 3'UTR of human albumin. In some further embodiments, it may be preferred if the open reading frame does not code for albumin or variants thereof that the 3'UTR element is a sequence which is identical to SEQ ID No. 1, SEQ ID No. 2, SEQ ID No. 32, SEQ ID No. 33, SEQ ID No. 34 or SEQ ID No. 35. Furthermore, in some embodiments it is preferred that the open reading frame does not code for human factor IX or a reporter protein, e.g., selected from the group consisting of globin proteins, (particularly beta-globin), luciferase proteins, GFP proteins or variants thereof, for example, variants exhibiting at least 70% sequence identity to a globin protein, a luciferase protein, or a GFP protein. Additionally, in specific embodiments it is preferred that the open reading frame does not contain an intron, particularly in case the open reading frame codes for human factor IX.

In one embodiment, the invention provides an artificial DNA molecule comprising an open reading frame, preferably an open reading frame which encodes a peptide or protein other than albumin; a 3'UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to SEQ ID No. 1, 32 or 34; and a polyadenylation signal and/or a poly(A) sequence. Furthermore, the invention provides an artificial DNA molecule comprising an open reading frame, preferably an open reading frame which encodes any peptide or protein other than albumin; a 3'UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to SEQ ID No. 3, 36 or 38.

Furthermore, the invention provides an artificial RNA molecule, preferably an artificial mRNA molecule or an artificial viral RNA molecule, comprising an open reading frame, preferably an open reading frame which encodes a peptide or protein other than albumin; a 3'UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to SEQ ID No. 2, 33 or 35; and a polyadenylation signal and/or a poly(A) sequence. Furthermore, the invention provides an artificial RNA molecule, preferably an artificial mRNA molecule or an artificial viral RNA molecule, comprising an open reading frame, preferably an open reading frame which encodes a peptide or protein other than albumin; a 3'UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to SEQ ID No. 4, 37 or 39.

The invention provides an artificial nucleic acid molecule, preferably an artificial mRNA, which may be characterized by enhanced stability and prolonged expression of the encoded peptide or protein. Without being bound by any theory, enhanced stability of protein expression and thus prolonged protein expression may result from reduction in degradation of the artificial nucleic acid molecule, such as an artificial mRNA molecule according to the present invention. Accordingly, the inventive 3'UTR element may prevent the artificial nucleic acid from degradation and decay.

In some embodiments, it is preferred that the 3'UTR element does not consist of a histone stem-loop, preferably does not comprise a histone stem-loop. In one embodiment, the artificial nucleic acid molecule according to the present invention does not comprise a histone stem-loop. However, in some embodiments, the artificial nucleic acid molecule may comprise a histone stem-loop in addition to the nucleic acid sequence derived from the 3'UTR of an albumin gene. Such artificial nucleic acid molecule according to the present invention, for example, may comprise in 5'-to-3'-direction an ORF, an inventive 3'UTR element, preferably comprising a polyadenylation signal, an optional histone stem-loop and an optional poly(A) sequence. It may also comprise in 5'-to-3'-direction an ORF, an inventive 3'UTR element, e.g. comprising a polyadenylation-signal, a poly(A) sequence and an optional histone stem-loop.

In the context of the present invention, such a histone stem-loop is typically derived from a histone gene and comprises an intramolecular base pairing of two neighbored entirely or partially reverse complementary sequences, thereby forming a stem-loop. A stem-loop can occur in single-stranded DNA or, more commonly, in RNA. The structure is also known as a hairpin or hairpin loop and usually consists of a stem and a (terminal) loop within a consecutive sequence, wherein the stem is formed by two neighbored entirely or partially reverse complementary sequences separated by a short sequence as sort of spacer, which builds the loop of the stem-loop structure. The two neighbored entirely or partially reverse complementary sequences may be defined as e.g. stem-loop elements stem1 and stem2.

The stem loop is formed when these two neighbored entirely or partially reverse complementary sequences, e.g. stem-loop elements stem1 and stem2, form base-pairs with each other, leading to a double stranded nucleic acid sequence comprising an unpaired loop at its terminal ending formed by the short sequence located between stem-loop elements stem1 and stem2 on the consecutive sequence. The unpaired loop thereby typically represents a region of the nucleic acid which is not capable of base pairing with either of these stem-loop elements. The resulting lollipop-shaped structure is a key building block of many RNA secondary structures. The formation of a stem-loop structure is thus dependent on the stability of the resulting stem and loop regions, wherein the first prerequisite is typically the presence of a sequence that can fold back on itself to form a paired double strand. The stability of paired stem-loop elements is determined by the length, the number of mismatches or bulges it contains (a small number of mismatches is typically tolerable, especially in a long double strand), and the base composition of the paired region. In the context of the present invention, optimal loop length is 3-10 bases, more preferably 3 to 8, 3 to 7, 3 to 6 or even more preferably 4 to 5 bases, and most preferably 4 bases.

An example for a histone stem-loop sequence is the sequence according to SEQ ID NO: 31 (CAAAGGCTCTTTTCAGAGCCACCA) or the corresponding RNA sequence.

Thus, in some embodiments, the artificial nucleic acid molecule according to the present invention comprises (a.) at least one open reading frame; (b.) at least one 3'UTR element as described herein, and (d.) at least one histone-stem loop which may, for example, comprise or consist of a sequence having a sequence identity of at least about 75%, preferably of at least about 80%, preferably at least about 85%, more preferably at least about 90%, even more preferably at least about 95% to the sequence according to SEQ ID NO. 31 or the corresponding RNA sequence, wherein preferably positions 6, 13 and 20 of the sequence having a sequence identity of at least about 75%, preferably of at least about 80%, preferably at least about 85%, more preferably at least about 90%, even more preferably at least about 95% to the sequence according to SEQ ID NO. 31 or the corresponding RNA sequence are conserved, i.e. are identical to the nucleotides at positions 6, 13 and 20 of SEQ ID NO. 31.

In some embodiments, the artificial nucleic acid molecule comprises further elements such as a 5'-cap, a poly(C) sequence and/or an IRES-motif. A 5'-cap may be added post-transcriptionally to the 5' end of an RNA. Furthermore, the inventive artificial nucleic acid molecule, particularly if the nucleic acid is in the form of an mRNA or codes for an mRNA, may be modified by a sequence of at least 10 cytidines, preferably at least 20 cytidines, more preferably at least 30 cytidines (so-called "poly(C) sequence"). Particularly, the inventive nucleic acid molecule may contain, especially if the nucleic acid is in the form of an (m)RNA or codes for an mRNA, a poly(C) sequence of typically about 10 to 200 cytidine nucleotides, preferably about 10 to 100 cytidine nucleotides, more preferably about 10 to 70 cytidine nucleotides or even more preferably about 20 to 50 or even 20 to 30 cytidine nucleotides. Thus, preferably the artificial nucleic acid molecule according to the present invention comprises, preferably in 5'-to-3' direction, an ORF, at least one 3'UTR element as described above, a poly(A) sequence or a polyadenylation signal, and a poly(C) sequence.

An internal ribosome entry side (IRES) sequence or IRES-motif may separate several open reading frames, for example if the artificial nucleic acid molecule encodes for two or more peptides or proteins. An IRES-sequence may be particularly helpful if the mRNA is a bi- or multicistronic RNA.

Furthermore, the artificial nucleic acid molecule may comprise additional 5'-elements, preferably a 5'UTR, a promoter, or a 5'-UTR and a promoter containing-sequence. The promoter may drive and or regulate transcription of the artificial nucleic acid molecule according to the present invention, for example of an artificial DNA-molecule according to the present invention. Furthermore, the 5'UTR may interact with the inventive 3'UTR element and thus may support the stabilising effect of the inventive 3'UTR element. Such elements may further support stability and translational efficiency. Accordingly, in some embodiments, the invention provides artificial nucleic acid molecules, preferably mRNA-molecules, comprising in 5'-to-3'-direction at least one of the following structures 5'-cap-5'UTR-ORF-3'UTR element-histone stem-loop-poly(A) sequence 5'-cap-5'UTR-ORF-3'UTR element-poly(A) sequence-histone stem-loop 5'-cap-5'UTR-ORF-IRES-ORF-3'-UTR element-histone stem-loop-poly(A) sequence 5'-cap-5'UTR-ORF-IRES-ORF-3'-UTR element-histone stem-loop-poly(A) sequence-poly(C) sequence 5'-cap-5'UTR-ORF-IRES-ORF-3'UTR element-poly(A) sequence-histone stem-loop 5'-cap-5'UTR-ORF-IRES-ORF-3'UTR element-poly(A) sequence-poly(C) sequence-histone stem-loop 5'-cap-5'UTR-ORF-3'UTR element-poly(A) sequence-poly(C) sequence 5'-cap-5'UTR-ORF-3'UTR element-poly(A) sequence-poly(C) sequence-histone stem loop Preferably, the artificial nucleic acid molecule according to the present invention, preferably the open reading frame, is at least partially G/C modified. Thus, the inventive artificial nucleic acid molecule may be thermodynamically stabilized by modifying the G (guanosine)/C (cytidine) content of the molecule. The G/C content of the open reading frame of an artificial nucleic acid molecule according to the present invention may be increased compared to the G/C content of the open reading frame of a corresponding wild type sequence, preferably by using the degeneration of the genetic code. Thus, the encoded amino acid sequence of the nucleic acid molecule is preferably not modified by the G/C modification compared to the coded amino acid sequence of the particular wild type sequence. The codons of a coding sequence or a whole nucleic acid molecule, e.g. an mRNA, may therefore be varied compared to the wild type coding sequence, such that they include an increased amount of G/C nucleotides while the translated amino acid sequence is maintained. In respect to the fact that several codons code for one and the same amino acid (so-called degeneration of the genetic code), the most favourable codons for the stability can be determined (so-called alternative codon usage).

Depending on the amino acid to be encoded by the coding region of the inventive nucleic acid molecule as defined herein, there are various possibilities for modification of the nucleic acid sequence, e.g. the open reading frame, compared to its wild type coding region. In the case of amino acids which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U/T is present.

In contrast, codons which contain A and/or U/T nucleotides may be modified by substitution of other codons which code for the same amino acids but contain no A and/or U/T. For example the codons for Pro can be modified from CC(U/T) or CCA to CCC or CCG;
the codons for Arg can be modified from CG(U/T) or CGA or AGA or AGG to CGC or CGG;
the codons for Ala can be modified from GC(U/T) or GCA to GCC or GCG;
the codons for Gly can be modified from GG(U/T) or GGA to GGC or GGG.

In other cases, although A or (U/T) nucleotides cannot be eliminated from the codons, it is however possible to decrease the A and (U/T) content by using codons which contain a lower content of A and/or (U/T) nucleotides. Examples of these are:
The codons for Phe can be modified from (U/T)(U/T)(U/T) to (U/T) (U/T)C; the codons for Leu can be modified from (U/T) (U/T)A, (U/T) (U/T)G, C(U/T) (U/T) or C(U/T)A to C(U/T)C or C(U/T)G;
the codons for Ser can be modified from (U/T)C(U/T) or (U/T)CA or AG(U/T) to (U/T)CC, (U/T)CG or AGC;
the codon for Tyr can be modified from (U/T)A(U/T) to (U/T)AC;
the codon for Cys can be modified from (U/T)G(U/T) to (U/T)GC;
the codon for His can be modified from CA(U/T) to CAC;
the codon for Gin can be modified from CAA to CAG;
the codons for Ile can be modified from A(U/T)(U/T) or A(U/T)A to A(U/T)C;
the codons for Thr can be modified from AC(U/T) or ACA to ACC or ACG;
the codon for Asn can be modified from AA(U/T) to AAC;
the codon for Lys can be modified from AAA to AAG;
the codons for Val can be modified from G(U/T)(U/T) or G(U/T)A to G(U/T)C or G(U/T)G;
the codon for Asp can be modified from GA(U/T) to GAC;
the codon for Glu can be modified from GAA to GAG;
the stop codon (U/T)AA can be modified to (U/T)AG or (U/T)GA.

In the case of the codons for Met (A(U/T)G) and Trp ((U/T)GG), on the other hand, there is no possibility of sequence modification without altering the encoded amino acid sequence.

The substitutions listed above can be used either individually or in all possible combinations to increase the G/C content of the open reading frame of the inventive nucleic acid sequence as defined herein, compared to its particular wild type open reading frame (i.e. the original sequence). Thus, for example, all codons for Thr occurring in the wild type sequence can be modified to ACC (or ACG).

Preferably, the G/C content of the open reading frame of the inventive artificial nucleic acid molecule as defined herein is increased by at least 7%, more preferably by at least 15%, particularly preferably by at least 20%, compared to the G/C content of the wild type coding region without altering the encoded amino acid sequence, i.e. using the degeneracy of the genetic code. According to a specific embodiment at least 5%, 10%, 20%, 30%, 40%, 50%, 60%, more preferably at least 70%, even more preferably at least 80% and most preferably at least 90%, 95% or even 100% of the substitutable codons in the open reading frame of the inventive artificial nucleic acid molecule or a fragment, variant or derivative thereof are substituted, thereby increasing the G/C content of said open reading frame.

In this context, it is particularly preferable to increase the G/C content of the open reading frame of the inventive nucleic acid sequence as defined herein, to the maximum (i.e. 100% of the substitutable codons), compared to the wild type open reading frame, without altering the encoded amino acid sequence.

Furthermore, the open reading frame is preferably at least partially codon-optimized. Codon-optimization is based on the finding that the translation efficiency may be determined by a different frequency in the occurrence of transfer RNAs (tRNAs) in cells. Thus, if so-called "rare codons" are present in the coding region of the inventive artificial nucleic acid molecule as defined herein, to an increased extent, the translation of the corresponding modified nucleic acid sequence is less efficient than in the case where codons coding for relatively "frequent" tRNAs are present.

Thus, the open reading frame of the inventive nucleic acid sequence is preferably modified compared to the corresponding wild type coding region such that at least one codon of the wild type sequence which codes for a tRNA which is relatively rare in the cell is exchanged for a codon which codes for a tRNA which is comparably frequent in the cell and carries the same amino acid as the relatively rare tRNA. By this modification, the open reading frame of the inventive artificial nucleic acid molecule as defined herein, is modified such that codons for which frequently occurring tRNAs are available may replace codons which correspond to rare tRNAs. In other words, according to the invention, by such a modification all codons of the wild type open reading frame which code for a rare tRNA may be exchanged for a codon which codes for a tRNA which is more frequent in the cell and which carries the same amino acid as the rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. Accordingly, preferably, the open reading frame is codon-optimized, preferably with respect to the system in which the nucleic acid molecule according to the present invention is to be expressed, preferably with respect to the system in which the nucleic acid molecule according to the present invention is to be translated. Preferably, the codon usage of the open reading frame is codon-optimized according to mammalian codon usage, more preferably according to human codon usage. Preferably, the open reading frame is codon-optimized and G/C-content modified.

For further improving degradation resistance, e.g. resistance to in vivo degradation by an exo- or endonuclease, and/or for further improving stability of protein expression from the artificial nucleic acid molecule according to the present invention, the artificial nucleic acid molecule may further comprise modifications, such as backbone modifications, sugar modifications and/or base modifications, e.g., lipid-modifications or the like. Preferably, the transcription and/or the translation of the artificial nucleic acid molecule according to the present invention is not significantly impaired by said modifications.

Nucleotide analogues/modifications that may be used in the context of the present invention may be selected, for example, from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'- triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-tri phosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-tri phosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

Further, lipid-modified artificial nucleic acid molecules may typically comprise at least one linker which is covalently linked with the artificial nucleic acid molecule, and at least one lipid which is covalently linked with this linker. Alternatively, a lipid-modified artificial nucleic acid molecule may comprise at least one artificial nucleic acid molecule as defined herein and at least one, preferably bifunctional lipid which is covalently linked, preferably without a linker, with that artificial nucleic acid molecule. According to a third alternative, a lipid-modified artificial nucleic acid molecule may comprise an artificial nucleic acid molecule as defined herein, at least one linker which is covalently linked with that artificial nucleic acid molecule, at least one lipid which is covalently linked with this linker, and additionally at least one, preferably bifunctional lipid which is covalently linked, preferably without a linker, with the artificial nucleic acid molecule.

In a further aspect, the present invention provides a vector comprising
a. an open reading frame (ORF) and/or a cloning site, e.g. for insertion of an open reading frame or a sequence comprising an open reading frame; and
b. at least one 3'-untranslated region element (3'UTR element) comprising a nucleic acid sequence which is derived from the 3'UTR of an albumin gene or from a variant of the 3'UTR of an albumin gene.

The at least one 3'UTR element and the ORF are as described above for the artificial nucleic acid molecule according to the present invention. The cloning site may be any sequence that is suitable for introducing an open reading frame or a sequence comprising an open reading frame, such as one or more restriction sites. Thus, the vector comprising a cloning site is preferably suitable for inserting an open reading frame into the vector, preferably for inserting an open reading frame 5' to the 3'UTR element. Preferably the cloning site or the ORF is located 5' to the 3'UTR element, preferably in close proximity to the 5'-end of the 3'UTR element. For example, the cloning site or the ORF may be directly connected to the 5'-end of the 3'UTR element or they may be connected via a stretch of nucleotides, such as by a stretch of 2, 4, 6, 8, 10, 20 etc. nucleotides as described above for the artificial nucleic acid molecule according to the present invention.

Preferably, the vector according to the present invention is suitable for producing the artificial nucleic acid molecule according to the present invention, preferably for producing an artificial mRNA according to the present invention, for example, by optionally inserting an open reading frame or a sequence comprising an open reading frame into the vector and transcribing the vector. Thus, preferably, the vector comprises elements needed for transcription, such as a promoter, e.g. an RNA polymerase promoter. Preferably, the vector is suitable for transcription using eukaryotic, prokaryotic, viral or phage transcription systems, such as eukaryotic cells, prokaryotic cells, or eukaryotic, prokaryotic, viral or phage in vitro transcription systems. Thus, for example, the vector may comprise a promoter sequence, which is recognizes by a polymerase, such as by an RNA polymerase, e.g. by a eukaryotic, prokaryotic, viral, or phage RNA polymerase. In a preferred embodiment, the vector comprises a phage RNA polymerase promoter such as an SP6 or T7, preferably a T7 promoter. Preferably, the vector is suitable for in vitro transcription using a phage based in vitro transcription system, such as a T7 RNA polymerase based in vitro transcription system.

The vector may further comprise a poly(A) sequence and/or a polyadenylation signal as described above for the artificial nucleic acid molecule according to the present invention.

The vector may be an RNA vector or a DNA vector. Preferably, the vector is a DNA vector. The vector may be any vector known to the skilled person, such as a viral vector or a plasmid vector. Preferably, the vector is a plasmid vector, preferably a DNA plasmid vector.

In a preferred embodiment, the vector according to the present invention comprises the artificial nucleic acid molecule according to the present invention.

Preferably, a DNA vector according to the present invention comprises a sequence according to SEQ ID No. 1, SEQ ID No. 3, SEQ ID No. 32, SEQ ID No. 34, SEQ ID No. 36 or SEQ ID No. 38, or a sequence having an identity of at least about 40%, preferably of at least about 50%, preferably of at least about 60%, preferably of at least about 70%, more preferably of at least about 80%, more preferably of at least about 90%, even more preferably of at least about 95%; even more preferably of at least about 99% sequence identity to the nucleic acid sequence according to SEQ ID No. 1, SEQ ID No. 3, SEQ ID No. 32, SEQ ID No. 34, SEQ ID No. 36 or SEQ ID No. 38, or a fragment thereof as described above, preferably a functional fragment thereof.

Preferably, an RNA vector according to the present invention comprises a sequence according to SEQ ID No. 2, SEQ ID No. 4, SEQ ID No. 33, SEQ ID No. 35, SEQ ID No. 37 or SEQ ID No. 39 or a sequence having an identity of at least about 40%, preferably of at least about 50%, preferably of at least about 60%, preferably of at least about 70%, more preferably of at least about 80%, more preferably of at least about 90%, even more preferably of at least about 95%; even more preferably of at least about 99% sequence identity to the nucleic acid sequence according to SEQ ID No. 2, SEQ ID No. 4, SEQ ID No. 33, SEQ ID No. 35, SEQ ID No. 37 or SEQ ID No. 39 or a fragment thereof, preferably a functional fragment thereof.

Preferably, the vector is a circular molecule. Preferably, the vector is a double-stranded molecule, such as a double stranded DNA molecule. Such circular, preferably double stranded DNA molecule may be used conveniently as a storage form for the inventive artificial nucleic acid molecule. Furthermore, it may be used for transfection of cells, for example, cultured cells. Also it may be used for in vitro transcription for obtaining an artificial RNA molecule according to the invention.

Preferably, the vector, preferably the circular vector, is linearizable, for example, by restriction enzyme digestion. In a preferred embodiment, the vector comprises a cleavage site, such as a restriction site, preferably a unique cleavage site, located immediately 3' to the 3'UTR element, or—if present—located 3' to the poly(A) sequence or polyadenylation signal, or—if present—located 3' to the poly(C) sequence, or—if present located 3' to the histone stem-loop. Thus, preferably, the product obtained by linearizing the vector terminates at the 3' end with the 3'-end of the 3'UTR element, or—if present—with the 3'-end of the poly(A) sequence or polyadenylation signal, or—if present—with the 3'-end of the poly(C) sequence. In the embodiment, wherein the vector according to the present invention comprises the artificial nucleic acid molecule according to the present invention, a restriction site, preferably a unique restriction site, is preferably located immediately 3' to the 3'-end of the artificial nucleic acid molecule.

In a further aspect, the present invention relates to a cell comprising the artificial nucleic acid molecule according to the present invention or the vector according to present invention. The cell may be any cell, such as a bacterial cell, insect cell, plant cell, vertebrate cell, e.g. a mammalian cell. Such cell may be, e.g., used for replication of the vector of the present invention, for example, in a bacterial cell. Furthermore, the cell may be used for transcribing the artificial nucleic acid molecule or the vector according to the present invention and/or translating the open reading frame of the artificial nucleic acid molecule or the vector according to the present invention. For example, the cell may be used for recombinant protein production.

The cells according to the present invention are, for example, obtainable by standard nucleic acid transfer methods, such as standard transfection, transduction or transformation methods. For example, the artificial nucleic acid molecule or the vector according to the present invention may be transferred into the cell by electroporation, lipofection, e.g. based on cationic lipids and/or liposomes, calcium phosphate precipitation, nanoparticle based transfection, virus based transfection, or based on cationic polymers, such as DEAE-dextran or polyethylenimine etc.

Preferably, the cell is a mammalian cell, such as a cell of human subject, a domestic animal, a laboratory animal, such as a mouse or rat cell. Preferably the cell is a human cell. The cell may be a cell of an established cell line, such as a CHO, BHK, 293T, COS-7, HELA, HEK, etc. or the cell may be a primary cell, such as a HDF cell etc., preferably a cell isolated from an organism. In a preferred embodiment, the cell is an isolated cell of a mammalian subject, preferably of a human subject. For example, the cell may be an immune cell, such as a dendritic cell, a cancer or tumor cell, or any somatic cell etc., preferably of a mammalian subject, preferably of a human subject.

In a further aspect, the present invention provides a pharmaceutical composition comprising the artificial nucleic acid molecule according to the present invention, the vector according the present invention, or the cell according to the present invention. The pharmaceutical composition according to the invention may be used, e.g., as a vaccine, for example, for genetic vaccination. Thus, the ORF may, e.g., encode an antigen to be administered to a patient for vaccination. Thus, in a preferred embodiment, the pharmaceutical composition according to the present invention is a vaccine. Furthermore, the pharmaceutical composition according to the present invention may be used, e.g., for gene therapy.

Preferably, the pharmaceutical composition further comprises one or more pharmaceutically acceptable excipients, vehicles, fillers and/or diluents. In the context of the present invention, a pharmaceutically acceptable vehicle typically includes a liquid or non-liquid basis for the inventive pharmaceutical composition. In one embodiment, the pharmaceutical composition is provided in liquid form. In this context, preferably, the vehicle is based on water, such as pyrogen-free water, isotonic saline or buffered (aqueous) solutions, e.g phosphate, citrate etc. buffered solutions. The buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of mammalian cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

One or more compatible solid or liquid fillers or diluents or encapsulating compounds suitable for administration to a patient may be used as well for the inventive pharmaceutical composition. The term "compatible" as used herein preferably means that these components of the inventive pharmaceutical composition are capable of being mixed with the inventive nucleic acid, vector or cells as defined herein in such a manner that no interaction occurs which would substantially reduce the pharmaceutical effectiveness of the inventive pharmaceutical composition under typical use conditions.

The pharmaceutical composition according to the present invention may optionally further comprise one or more additional pharmaceutically active components. A pharmaceutically active component in this context is a compound that exhibits a therapeutic effect to heal, ameliorate or prevent a particular indication or disease. Such compounds include, without implying any limitation, peptides or proteins, nucleic acids, (therapeutically active) low molecular weight organic or inorganic compounds (molecular weight less than 5000, preferably less than 1000), sugars, antigens or antibodies, therapeutic agents already known in the prior art, antigenic cells, antigenic cellular fragments, cellular fractions, cell wall components (e.g. polysaccharides), modified, attenuated or de-activated (e.g. chemically or by irradiation) pathogens (virus, bacteria etc.).

Furthermore, the inventive pharmaceutical composition may comprise a carrier for the artificial nucleic acid molecule or the vector. Such a carrier may be suitable for mediating dissolution in physiological acceptable liquids, transport and cellular uptake of the pharmaceutical active artificial nucleic acid molecule or the vector. Accordingly, such a carrier may be a component which may be suitable for depot and delivery of an artificial nucleic acid molecule or vector according to the invention. Such components may be, for example, cationic or polycationic carriers or compounds which may serve as transfection or complexation agent.

Particularly preferred transfection or complexation agents in this context are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Droso-*

*phila antennapedia*), pAntp, plsl, FGF, Lactoferrin, Transportan, Buforin-2, Bac715-24, SynB, SynB(1), pVEC, hCT-derived peptides, SAP, or histones.

Furthermore, such cationic or polycationic compounds or carriers may be cationic or polycationic peptides or proteins, which preferably comprise or are additionally modified to comprise at least one —SH moiety. Preferably, a cationic or polycationic carrier is selected from cationic peptides having the following sum formula (I):

$$\{(Arg)_l;(Lys)_m;(His)_n;(Orn)_o;(Xaa)_x\}; \quad \text{formula (I)}$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred.

Further, the cationic or polycationic peptide or protein, when defined according to formula $\{(Arg)_l; (Lys)_m; (His)_n; (Orn)_o; (Xaa)_x\}$(formula (I)) as shown above and which comprise or are additionally modified to comprise at least one —SH moeity, may be, without being restricted thereto, selected from subformula (Ia):

$$\{(Arg)_l;(Lys)_m;(His)_n;(Orn)_o;(Xaa')_x(Cys)_y\} \quad \text{subformula (Ia)}$$

wherein $(Arg)_l$; $(Lys)_m$; $(His)_n$; $(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. Further, the cationic or polycationic peptide may be selected from subformula (Ib):

$$Cys_1\{(Arg)_l;(Lys)_m;(His)_n;(Orn)_o;(Xaa)_x\}Cys_2 \quad \text{subformula (Ib)}$$

wherein empirical formula $\{(Arg)_l; (Lys)_m; (His)_n; (Orn)_o; (Xaa)_x\}$(formula (III)) is as defined herein and forms a core of an amino acid sequence according to (semiempirical) formula (III) and wherein $Cys_1$ and $Cys_2$ are Cysteines proximal to, or terminal to $(Arg)_l$; $(Lys)_m$; $(His)_n$; $(Orn)_o$; $(Xaa)_x$.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g polyethyleneglycole); etc.

In this context it is particularly preferred that the inventive artificial nucleic acid molecule or the inventive vector is complexed at least partially with a cationic or polycationic compound, preferably cationic proteins or peptides. Partially means that only a part of the inventive artificial nucleic acid molecule or the inventive vector is complexed with a cationic or polycationic compound and that the rest of the inventive artificial nucleic acid molecule or the inventive vector is in uncomplexed form ("free"). Preferably the ratio of complexed nucleic acid to: free nucleic acid is selected from a range. of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed nucleic acid to free nucleic acid is selected from a ratio of about 1:1 (w/w).

The pharmaceutical composition according to the present invention may optionally further comprise one or more adjuvants, for example, adjuvants for stimulating the innate immune system or for enhancing cellular uptake of the artificial nucleic acid molecule or vector. In this context, an adjuvant may be understood as any compound, which is suitable to initiate or increase an immune response of the innate immune system, i.e. a non-specific immune response. In other words, when administered, the inventive pharmaceutical composition preferably elicits an innate immune response due to the adjuvant, optionally contained therein. Preferably, such an adjuvant may be an adjuvant supporting the induction of an innate immune response in a mammal. Such an adjuvant may be, for example, an immunostimulatory nucleic acid, i.e. a nucleic acid that may bind to a Toll-like-receptor or the like, preferably an immunostimulatory RNA.

Such adjuvants, preferably such immunostimulatory nucleic acids, may induce an innate, i.e. unspecific, immune response which may support a specific, i.e. adaptive, immune response to the peptide or protein, i.e. the antigen, encoded by the artificial nucleic acid molecule of the pharmaceutical composition, preferably the vaccine.

The inventive pharmaceutical composition may also additionally comprise any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Further additives which may be included in the inventive pharmaceutical composition are, e.g., emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives etc.

The pharmaceutical composition according to the present invention preferably comprises a "safe and effective amount" of the components of the pharmaceutical composition, particularly of the inventive nucleic acid sequence, the vector and/or the cells as defined herein.

As used herein, a "safe and effective amount" means an amount sufficient to significantly induce a positive modification of a disease or disorder as defined herein. At the same time, however, a "safe and effective amount" preferably avoids serious side-effects and permits a sensible relationship between advantage and risk. The determination of these limits typically lies within the scope of sensible medical judgment.

In a further aspect, the present invention provides the artificial nucleic acid molecule according to the present invention, the vector according to the present invention, the cell according to the present invention, or the pharmaceutical composition according to the present invention for use as a medicament, for example, as vaccine (in genetic vaccination) or in gene therapy.

The artificial nucleic acid molecule according to the present invention, the vector according to the present invention, the cell according to the present invention, or the pharmaceutical composition according to the present invention are particularly suitable for any medical application which makes use of the therapeutic action or effect of peptides, polypeptides or proteins, or where supplementation of a particular peptide or protein is needed. Thus, the present invention provides the artificial nucleic acid molecule according to the present invention, the vector according to the present invention, the cell according to the present invention, or the pharmaceutical composition according to the present invention for use in the treatment or prevention of diseases or disorders amenable to treatment by the therapeutic action or effect of peptides, polypeptides or proteins or amenable to treatment by supplementation of a particular peptide, polypeptide or protein. For example, the artificial nucleic acid molecule according to the present invention, the vector according to the present invention, the cell according to the present invention, or the pharmaceutical composition according to the present invention may be used for the treatment or prevention of genetic diseases, autoimmune diseases, cancerous or tumour-related diseases, infectious diseases, chronic diseases or the like, e.g., by genetic vaccination or gene therapy.

In particular, such therapeutic treatments which benefit from a stable and prolonged presence of therapeutic peptides, polypeptides or proteins in a subject to be treated are especially suitable as medical application in the context of the present invention, since the inventive 3'UTR element provides for a stable and prolonged expression of the ORF of the inventive nucleic acid molecule. Thus, a particularly suitable medical application for the artificial nucleic acid molecule according to the present invention, the vector according to the present invention, the cell according to the present invention, or the pharmaceutical composition according to the present invention is vaccination. Thus, the present invention provides the artificial nucleic acid molecule according to the present invention, the vector according to the present invention, the cell according to the present invention, or the pharmaceutical composition according to the present invention for vaccination of a subject, preferably a mammalian subject, more preferably a human subject. Preferred vaccination treatments are vaccination against infectious diseases, such as bacterial, protozoal or viral infections, and anti-tumour-vaccination. Such vaccination treatments may be prophylactic or therapeutic.

Depending on the disease to be treated or prevented, the ORF may be selected. For example, the open reading frame may code for a protein that has to be supplied to a patient suffering from total lack or at least partial loss of function of a protein, such as a patient suffering from a genetic disease. Additionally the open reading frame may be chosen from an ORF coding for a peptide or protein which beneficially influences a disease or the condition of a subject. Furthermore, the open reading frame may code for a peptide or protein which effects down-regulation of a pathological overproduction of a natural peptide or protein or elimination of cells expressing pathologically a protein or peptide. Such lack, loss of function or overproduction may, e.g., occur in the context of tumour and neoplasia, autoimmune diseases, allergies, infections, chronic diseases or the like. Furthermore, the open reading frame may code for an antigen or immunogen, e.g. for an epitope of a pathogen or for a tumour antigen. Thus, in preferred embodiments, the artificial nucleic acid molecule or the vector according to the present invention comprises an ORF encoding an amino acid sequence comprising or consisting of an antigen or immunogen, e.g. an epitope of a pathogen or a tumour-associated antigen, a 3'UTR element as described above, and optional further components, such as a poly(A) sequence etc.

In the context of medical application, in particular, in the context of vaccination, it is preferred that the artificial nucleic acid molecule according to the present invention is RNA, preferably mRNA, since DNA harbours the risk of eliciting an anti-DNA immune response and tends to insert into genomic DNA. However, in some embodiments, for example, if a viral delivery vehicle, such as an adenoviral delivery vehicle is used for delivery of the artificial nucleic acid molecule or the vector according to the present invention, e.g., in the context of gene therapeutic treatments, it may be desirable that the artificial nucleic acid molecule or the vector is a DNA molecule.

The artificial nucleic acid molecule according to the present invention, the vector according to the present invention, the cell according to the present invention, or the pharmaceutical composition according to the present invention may be administered orally, parenterally, by inhalation spray, topically, rectally, nasally, buccally, vaginally or via an implanted reservoir. The term parenteral as used herein includes subcutaneous, intravenous, intramuscular, intraarticular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the artificial nucleic acid molecule according to the present invention, the vector according to the present invention, the cell according to the present invention, or the pharmaceutical composition according to the present invention is administered parenterally, e.g. by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, sublingual injection or via infusion techniques. Particularly preferred is intradermal and intramuscular injection. Sterile injectable forms of the inventive pharmaceutical composition may be aqueous or oleaginous suspension. These suspensions may be formulated according to techniques known in the art using suitable dispersing or wetting agents and suspending agents.

The artificial nucleic acid molecule according to the present invention, the vector according to the present invention, the cell according to the present invention, or the pharmaceutical composition according to the present invention may also be administered orally in any orally acceptable dosage form including, but not limited to, capsules, tablets, aqueous suspensions or solutions.

The artificial nucleic acid molecule according to the present invention, the vector according to the present invention, the cell according to the present invention, or the pharmaceutical composition according to the present invention may also be administered topically, especially when, the target of treatment includes areas or organs readily accessible by topical application, e.g. including diseases of the skin or of any other accessible epithelial tissue. Suitable topical formulations are readily prepared for each of these areas or organs. For topical applications, the artificial nucleic acid molecule according to the present invention, the vector according to the present invention, the cell according to the present invention, or the pharmaceutical composition according to the present invention may be formulated in a suitable ointment suspended or dissolved in one or more carriers.

In one embodiment, the use as a medicament comprises the step of transfection of mammalian cells, preferably in vitro transfection of mammalian cells, more preferably in vitro transfection of isolated cells of a subject to be treated by the medicament. If the use comprises the in vitro transfection of isolated cells, the use as a medicament may further comprise the (re)administration of the transfected cells to the patient. The use of the inventive artificial nucleic acid molecules or the vector as a medicament may further comprise the step of selection of successfully transfected isolated cells. Thus, it may be beneficial if the vector further comprises a selection marker. Also, the use as a medicament may comprise in vitro transfection of isolated cells and purification of an expression-product, i.e. the encoded peptide or protein from these cells. This purified peptide or protein may subsequently be administered to a subject in need thereof.

The present invention also provides a method for treating or preventing a disease or disorder as described above comprising administering the artificial nucleic acid molecule according to the present invention, the vector according to the present invention, the cell according to the present invention, or the pharmaceutical composition according to the present invention to a subject in need thereof.

Furthermore, the present invention provides a method for treating or preventing a disease or disorder comprising transfection of a cell with an artificial nucleic acid molecule according to the present invention or with the vector according to the present invention. Said transfection may be performed in vitro or in vivo. In a preferred embodiment, transfection of a cell is performed in vitro and the transfected cell is administered to a subject in need thereof, preferably to a human patient. Preferably, the cell which is to be transfected in vitro is an isolated cell of the subject, preferably of the human patient. Thus, the present invention provides a method of treatment comprising the steps of isolating a cell from a subject, preferably from a human patient, transfecting the isolated cell with the artificial nucleic acid according to the present invention or the vector according to the present invention, and administering the transfected cell to the subject, preferably the human patient.

The method of treating or preventing a disorder according to the present invention is preferably a vaccination method and/or a gene therapy method as described above.

As described above, the inventive 3'UTR element is capable of stabilizing an mRNA molecule and/or of stabilizing and/or prolonging the protein production from an mRNA molecule. Thus, in a further aspect, the present invention relates to a method for stabilizing an RNA molecule, preferably an mRNA molecule, comprising the step of associating the RNA molecule, preferably the mRNA molecule, or a vector encoding the RNA molecule, with a 3'UTR element comprising or consisting of a nucleic acid sequence which is derived from the 3'UTR of an albumin gene or from a variant of the 3'UTR of an albumin gene, preferably with the 3'UTR element as described above.

Furthermore, the present invention relates to a method for increasing protein production from an artificial nucleic acid molecule or from a vector, preferably from an mRNA molecule, and/or for stabilizing and/or prolonging protein production from an artificial nucleic acid molecule or from a vector, preferably from an mRNA molecule, the method comprising the step of associating the artificial nucleic acid molecule or the vector, preferably the mRNA molecule, with a 3'UTR element which comprises or consists of a nucleic acid sequence which is derived from the 3'UTR of an albumin gene or from a variant of the 3'UTR of an albumin gene, preferably with the 3'UTR element as described above.

The term "associating the artificial nucleic acid molecule or the vector with a 3'UTR element" in the context of the present invention preferably means functionally associating or functionally combining the artificial nucleic acid molecule or the vector with the 3'UTR element. This means that the artificial nucleic acid molecule or the vector and the 3'UTR element, preferably the 3'UTR element as described above, are associated or coupled such that the function of the 3'UTR element, e.g., the RNA and/or protein production stabilizing function, is exerted. Typically, this means that the 3'UTR element is integrated into the artificial nucleic acid molecule or the vector, preferably the mRNA molecule, 3' to an open reading frame, preferably immediately 3' to an open reading frame, preferably between the open reading frame and a poly(A) sequence or a polyadenylation signal. Preferably, the 3'UTR element is integrated into the artificial nucleic acid molecule or the vector, preferably the mRNA, as 3'UTR, i.e. such that the 3'UTR element is the 3'UTR of the artificial nucleic acid molecule or the vector, preferably the mRNA, i.e., such that it extends from the 3'-side of the open reading frame to the 5'-side of a poly(A) sequence or a polyadenylation signal, optionally connected via short linker, such as a sequence comprising or consisting of one or more restriction sites. Thus, preferably, the term "associating the artificial nucleic acid molecule or the vector with a 3'UTR element" means functionally associating the 3'UTR element with an open reading frame located within the artificial nucleic acid molecule or the vector, preferably within the mRNA molecule. The 3'UTR and the ORF are as described above for the artificial nucleic acid molecule according to the present invention, for example, preferably the ORF and the 3'UTR are heterologous, e.g. derived from different genes, as described above.

In a further aspect, the present invention provides the use of a 3'UTR element, preferably the 3'UTR element as described above, for increasing the stability of an RNA molecule, preferably of an mRNA molecule, wherein the 3'UTR element comprises or consists of a nucleic acid sequence which is derived from the 3'UTR of an albumin gene or from a variant of the 3'UTR of an albumin gene.

Furthermore, the present invention provides the use of a 3'UTR element, preferably the 3'UTR element as described above, for increasing protein production from an artificial nucleic acid molecule or a vector, preferably from an mRNA molecule, and/or for stabilizing and/or prolonging protein production from an artificial nucleic acid molecule or a vector molecule, preferably from an mRNA molecule, wherein the 3'UTR element comprises or consists of a nucleic acid sequence which is derived from the 3'UTR of an albumin gene or from a variant of the 3'UTR of an albumin gene as described above.

The uses according to the present invention preferably comprise associating the artificial nucleic acid molecule, the vector, or the RNA with the 3'UTR element as described above.

The compounds and ingredients of the inventive pharmaceutical composition may also be manufactured and traded separately of each other. Thus, the invention relates further to a kit or kit of parts comprising an artificial nucleic acid molecule according to the invention, an vector according the invention, a cell according to the invention, and/or a pharmaceutical composition according to the invention. Preferably, such kit or kits of parts may, additionally, comprise instructions for use, cells for transfection, an adjuvant, a means for administration of the pharmaceutical composition, a pharmaceutically acceptable carrier and/or an pharmaceutically acceptable solution for dissolution or dilution of the artificial nucleic acid molecule, the vector, the cells or the pharmaceutical composition.

The following Figures, Sequences and Examples are intended to illustrate the invention further. They are not intended to limit the subject matter of the invention thereto.

FIG. 1 shows the effect of the human α-globin 3'UTR, of the human albumin 3'UTR and of the human β-glucuronidase 3'UTR on luciferase expression from an artificial mRNA. Therein, the mRNA comprising the human albumin 3'UTR is an mRNA according to the present invention. It comprises an open reading frame encoding Luciferase of *Photinus pyralis*, followed in 5'-to-3'-direction by a 3'UTR element according to SEQ ID No. 2 and by a poly(A) sequence having a length of 64 adenines. A markedly extended protein expression from the artificial mRNA containing the human albumin 3'UTR corresponding to SEQ ID No. 2 is observable.

The effect of the human α-globin 3'UTR, of the human albumin 3'-UTR, or of the human β-glucuronidase 3'-UTR on luciferase expression from mRNA was examined, compared to Luciferase expression from mRNA lacking a 3'-UTR. Therefore, different mRNAs were electroporated into HeLa cells. Luciferase levels were measured at 6, 24, and 48 hours after transfection. The luciferase level from mRNA lacking a 3'-UTR drops from 6 hours to 48 hours, 10% of the 6-hours-signal remaining at 48 hours. The α-globin 3'-UTR stabilizes luciferase expression from mRNA moderately. Strikingly however, the inventive human albumin 3'-UTR further markedly extends Luciferase expression from mRNA. In contrast, the 3'-UTR of the stable β-glucuronidase mRNA does not extend Luciferase expression to the extent observed for the albumin 3'-UTR, confirming that the albumin 3'-UTR is particularly efficient at extending protein expression from mRNA. Data are graphed as mean RLU±SD (relative light units±standard deviation) for triplicate transfections. RLU are summarized in Example 5.1.

FIG. 2 shows the effect of the human albumin 3'-UTR on luciferase expression from mRNA, compared to luciferase expression from mRNA containing the human α-globin 3'-UTR or the 3'-UTR each of several different stable mRNAs. Therefore, different mRNAs were electroporated into HeLa cells. Luciferase levels were measured at 6, 24, and 48 hours after transfection. The luciferase level from mRNA lacking a 3'-UTR drops from 6 hours to 48 hours, 14% of the 6-hours-signal remaining at 48 hours. The α-globin 3'-UTR stabilizes luciferase expression from mRNA moderately. Strikingly however, the inventive human albumin 3'-UTR further markedly extends luciferase expression from mRNA. Compared to the albumin 3'-UTR, the 3'-UTRs of several different stable mRNAs do affect luciferase expression from mRNA in a much less favourable manner: The atp5o and atp5l 3'-UTRs stabilize luciferase expression much less than the albumin 3'-UTR. In addition, atp5o and atp5l 3'-UTRs reduce luciferase levels substantially compared to the albumin 3'-UTR. The 3'-UTR of the stable ndufa1 mRNA does stabilize luciferase expression markedly. However, the ndufa1 3'-UTR also reduces luciferase levels substantially. The albumin 3'-UTR is unique at extending protein expression while maintaining total protein expression. Data are graphed as mean RLU±SD (relative light units±standard deviation) for triplicate transfections. RLU are summarized in Example 5.2.

FIG. 3 shows the effect of point mutations to remove either a HindIII and/or an XbaI restriction site and/or a T7 termination signal from the human albumin 3'-UTR on luciferase expression from mRNA containing the human albumin 3'-UTR. Therefore, different mRNAs were electroporated into HeLa cells. Luciferase levels were measured at 6, 24, 48, and 72 hours after transfection. The PpLuc Signal was corrected for transfection efficiency by the signal of cotransfected RrLuc. The α-globin 3'-UTR stabilizes luciferase expression from mRNA only very moderately. In contrast, all variants of the albumin 3'-UTR markedly extend luciferase expression from mRNA. Data are graphed as mean RLU±SD (relative light units±standard deviation) for triplicate transfections. RLU are summarized in Example 5.4.

FIG. 4 shows the mRNA sequence of PpLuc(GC)-A64 lacking a 3'-UTR.

FIG. 5 shows the mRNA sequence of PpLuc(GC)-albumin-A64. The 3'-UTR of human albumin was inserted between ORF and poly(A). The sequence was taken from Dugaiczyk et al. 1982; Proc Natl Acad Sci USA. January; 79(1):71-5.

FIG. 6 shows the mRNA sequence of PpLuc(GC)-albumin2-A64. The 3'-UTR of human albumin, with the T7 termination signal removed by a single point mutation, was inserted between ORF and poly(A).

FIG. 7 shows the mRNA sequence of PpLuc(GC)-albumin3-A64. The 3'-UTR of human albumin, with the T7 termination signal removed by a single point mutation, was inserted between ORF and poly(A).

FIG. 8 shows the mRNA sequence of PpLuc(GC)-albumin4-A64. The 3'-UTR of human albumin, with the T7 termination signal removed by a single point mutation, was inserted between ORF and poly(A).

FIG. 9 shows the mRNA sequence of PpLuc(GC)-albumin5-A64. The 3'-UTR of human albumin, with the T7 termination signal removed by two consecutive point mutations, was inserted between ORF and poly(A).

FIG. 10 shows the mRNA sequence of PpLuc(GC)-albumin6-A64. The 3'-UTR of human albumin, with the HindIII and XbaI restriction sites removed by two single point mutations, was inserted between ORF and poly(A).

FIG. 11 shows the mRNA sequence of PpLuc(GC)-albumin7-A64. The 3'-UTR of human albumin, with the T7 termination signal as well as the HindIII and XbaI restriction sites removed by three single point mutations, was inserted between ORF and poly(A).

FIG. 12 shows the mRNA sequence of PpLuc(GC)-ag-A64. The center, α-complex-binding portion of the 3'-UTR of human α-globin was inserted between ORF and poly(A).

FIG. 13 shows the mRNA sequence of PpLuc(GC)-gusb-A64. The 3'-UTR of human β-glucuronidase was inserted between ORF and poly(A).

FIG. 14 shows the mRNA sequence of PpLuc(GC)-atp5o-A64. The 3'-UTR of human ATP synthase subunit O was inserted between ORF and poly(A).

FIG. 15 shows the mRNA sequence of PpLuc(GC)-ndufa1-A64. The 3'-UTR of human NADH dehydrogenase [ubiquinone]1α subcomplex subunit 1 was inserted between ORF and poly(A).

FIG. 16 shows the mRNA sequence of PpLuc(GC)-atp5l-A64. The 3'-UTR of human ATP synthase subunit g was inserted between ORF and poly(A).

Figure 17:
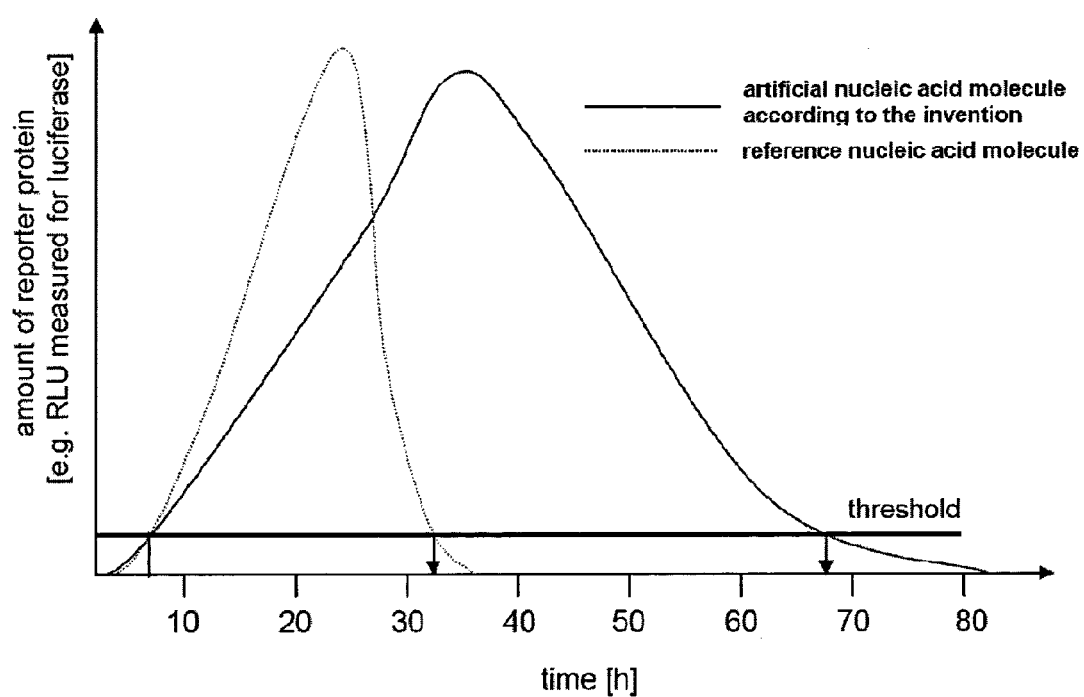

FIG. 17 illustrates exemplarily the protein production stabilizing and/or protein production prolonging effect of the 3'UTR element according to the present invention. The curves represent the amount of protein produced from nucleic acid molecules, e.g. in mammalian cells, measured over time. The continuous line represents protein production from the artificial nucleic acid molecule according to the present invention, e.g. an artificial mRNA, the dashed line represents the protein production from a reference nucleic acid molecule, e.g. lacking a 3'UTR or comprising a reference 3'UTR such as a 3'UTR naturally occurring with the ORF encoding the reporter protein. The continuous horizontal bold line represents a threshold value. This may be, for example, the protein amount measured 1, 2, 3, 4, 5, or 6 hours post initiation of expression, such as post transfection of the nucleic acid molecule. It can be seen that the protein amount produced from a reference nucleic acid molecule undercuts the threshold value at about 32 hours post initiation of expression, such as post transfection, whereas the protein amount produced from the artificial nucleic acid molecule according to the present invention undercuts the threshold value at about 68 hours post initiation of expression, such as post transfection. The total amount of protein produced equals the area under the curve (AUC). Preferably, the total amount of protein produced from the artificial nucleic acid molecule according to the present invention is at least the total amount of protein produced from a reference nucleic acid molecule lacking a 3'UTR.

Figure 18:
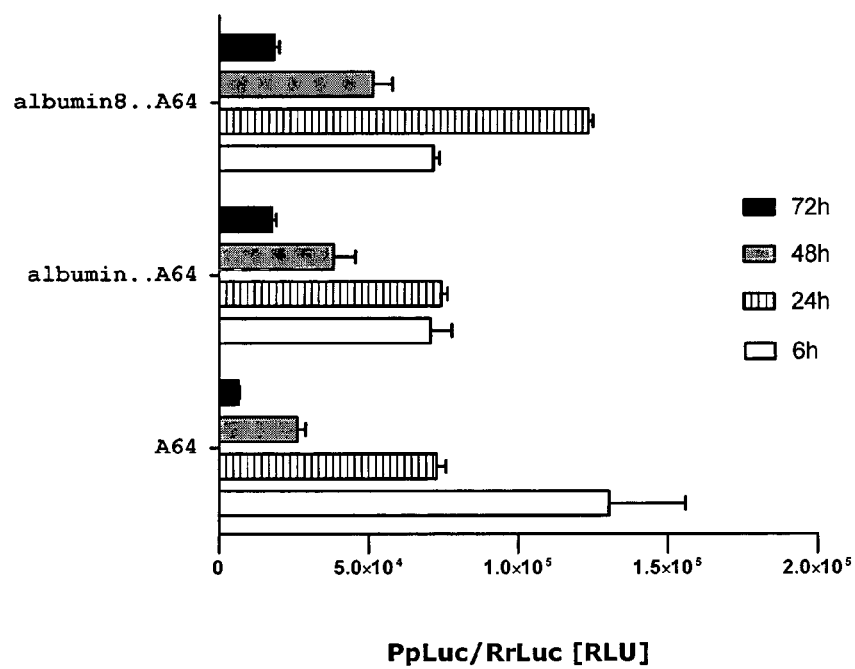

FIG. 18 shows the effect of different albumin 3'-UTRs from primates on luciferase expression from artificial mRNA, compared to luciferase expression from mRNA lacking a 3'-UTR. Therein, the mRNA comprising the human albumin 3'UTR (albumin) and the mRNA comprising the 3'UTR of albumin from Olive baboon (albumin8) are mRNAs according to the present invention. They comprise an open reading frame encoding Luciferase of *Photinus pyralis*, followed in 5'-to-3'-direction by a 3'UTR element according to SEQ ID No. 2 or SEQ ID No. 33 and by a poly(A) sequence having a length of 64 adenines. A markedly extended protein expression from the artificial mRNAs containing the albumin 3'UTRs corresponding to SEQ ID No. 2 or SEQ ID No. 33 is observable.

The effect of the human albumin 3'-UTR and the 3'UTR of albumin from Olive baboon on luciferase expression from mRNA was examined, compared to Luciferase expression from mRNA lacking a 3'-UTR. To examine the luciferase expression, the different mRNAs were electroporated into human dermal fibroblasts (HDF). Luciferase levels were measured at 6, 24, 48, and 72 hours after transfection. The luciferase level from mRNA lacking a 3'-UTR drops from 6 hours to 72 hours, 5% of the 6-hours-signal remaining at 72 hours. Again, the inventive human albumin 3'-UTR markedly extends luciferase expression from mRNA. The albumin 3'-UTR from Olive baboon (albumin8) extends luciferase expression from mRNA to the same extent as the human albumin 3'UTR sequence. Albumin 3'-UTRs from primates are thus particularly suitable for extending protein expression from mRNA. Data are graphed as mean RLU±SD (relative light units±standard deviation) for triplicate transfections. RLU are summarized in Example 5.4, table 7.

Figure 19:
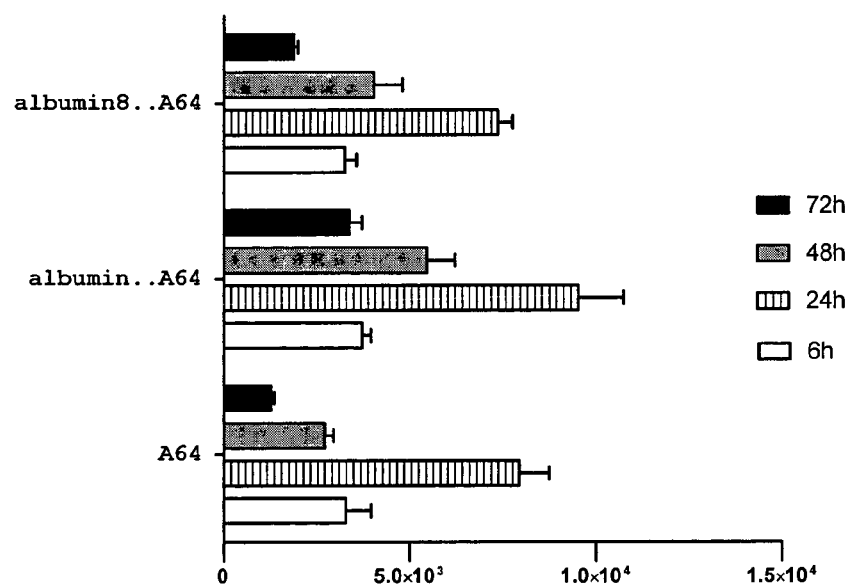

FIG. 19 shows the effect of different albumin 3'-UTRs from primates on luciferase expression from mRNA, compared to luciferase expression from mRNA lacking a 3'-UTR, using a different method of transfection. Therefore, different mRNAs were lipofected into human dermal fibroblasts (HDF). Luciferase levels were measured at 6, 24, 48, and 72 hours after transfection. The luciferase level from mRNA lacking a 3'-UTR drops from 6 hours to 48 hours to 82% of the 6-hours-signal. Again, the human albumin 3'-UTR markedly extends luciferase expression from mRNA, the 48-hours signal being higher than the 6-hours signal. The albumin 3'-UTR from Olive baboon (albumin8) extends luciferase expression from mRNA to a similar extent as the human albumin 3'UTR sequence. Albumin 3'-UTRs from primates are thus particularly suitable for extending protein expression from mRNA. Data are graphed as mean RLU±SD (relative light units±standard deviation) for triplicate transfections. RLU are summarized in Example 5.4, table 9.

Figure 20:
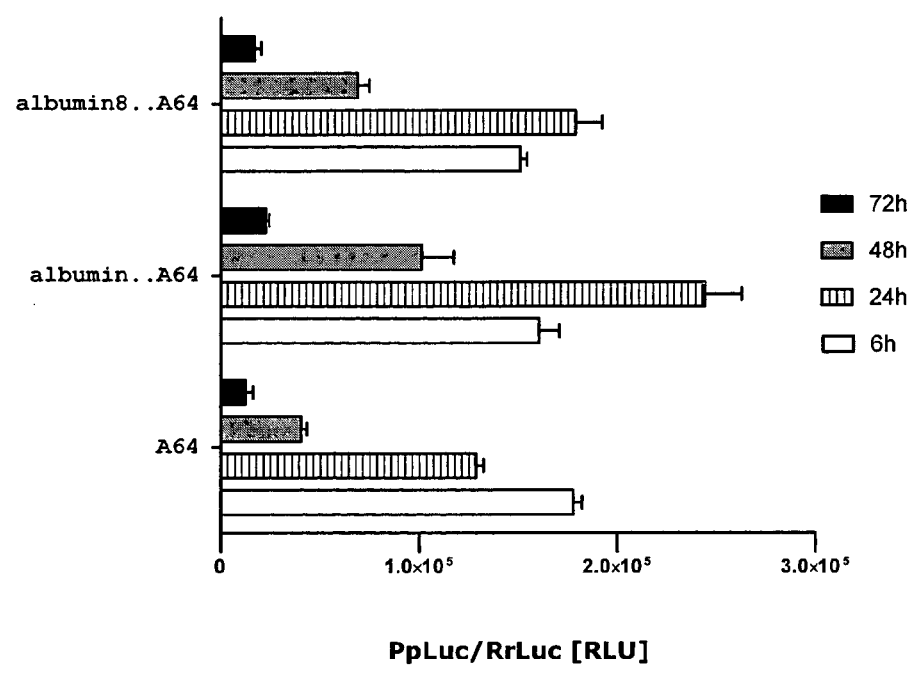

FIG. 20 shows the effect of different albumin 3'-UTRs from primates on luciferase expression from mRNA in mouse cells, compared to luciferase expression from mRNA lacking a 3'-UTR. Therefore, different mRNAs were lipofected into L-929 cells, a murine fibroblast cell line. Luciferase levels were measured at 6, 24, 48, and 72 hours after transfection. The luciferase level from mRNA lacking a 3'-UTR drops from 6 hours to 48 hours, 23% of the 6-hours-signal remaining at 48 hours. Even in the murine cells does the human albumin 3'-UTR markedly extend luciferase expression from mRNA. The albumin 3'-UTR from Olive baboon (albumin8) extends luciferase expression from mRNA similarly. Albumin 3'-UTRs from primates are thus particularly suitable for extending protein expression from mRNA in mammalian cell types. Data are graphed as mean RLU±SD (relative light units±standard deviation) for triplicate transfections. RLU are summarized in Example 5.5, table 11.

Figure 21:
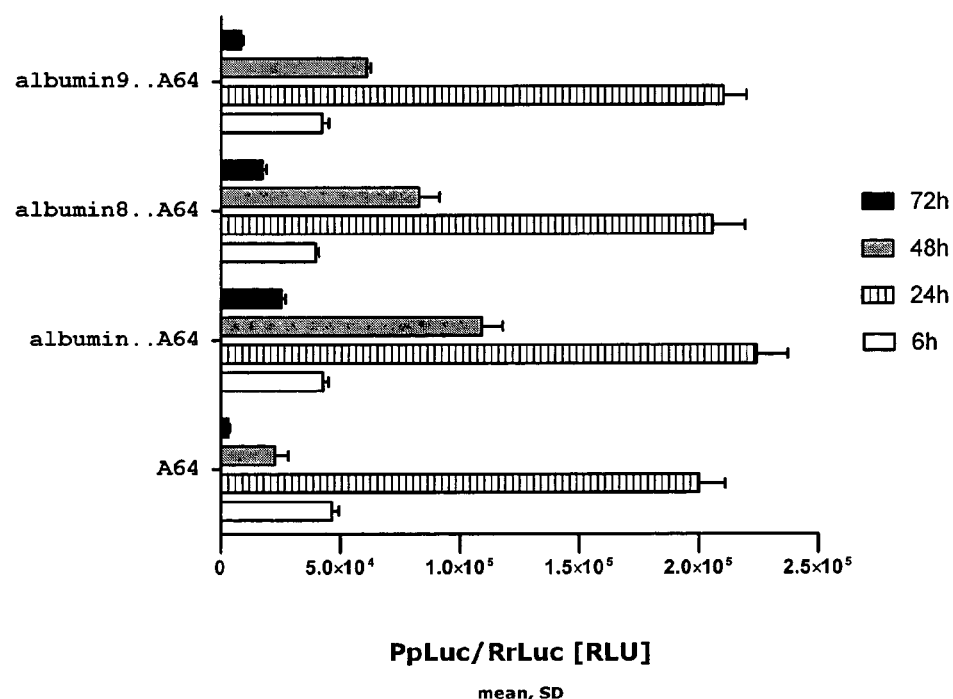

FIG. 21 shows the effect of different albumin 3'-UTRs from mammals on luciferase expression from mRNA, compared to luciferase expression from mRNA lacking a 3'-UTR. Therefore, different mRNAs were lipofected into HeLa cells. Luciferase levels were measured at 6, 24, 48, and 72 hours after transfection. The luciferase level from mRNA lacking a 3'-UTR drops from 6 hours to 48 hours, 49% of the 6-hours-signal remaining at 48 hours. Again, the human albumin 3'-UTR and the albumin 3'-UTR from Olive baboon (albumin8) markedly extend luciferase expression from mRNA, the 48-hours signal being higher than the 6-hours signal. Importantly, also the albumin 3'-UTR from mouse (albumin9) extends luciferase expression from mRNA similarly. Albumin 3'-UTRs from mammals are thus particularly suitable for extending protein expression from mRNA. Data are graphed as mean RLU±SD (relative light units±standard deviation) for triplicate transfections. RLU are summarized in Example 5.6, table 13.

FIG. 22 shows the mRNA sequence of PpLuc(GC)-albumin8-A64. The 3'-UTR of Olive baboon albumin was inserted between ORF and poly(A). The sequence was taken from the NCBI Reference Sequence XM_003898783.1.

FIG. 23 shows the mRNA sequence of PpLuc(GC)-albumin9-A64. The 3'-UTR of mouse albumin was inserted between ORF and poly(A). The sequence was taken from the NCBI Reference Sequence NM_009654.3.

EXAMPLES

1. Preparation of DNA-templates

A vector for in vitro transcription was constructed containing a T7 promoter followed by a GC-enriched sequence coding for *Photinus pyralis* luciferase (PpLuc(GC)) and an A64 poly(A) sequence. The poly(A) sequence was immediately followed by a restriction site used for linearization of the vector before in vitro transcription in order to obtain mRNA ending in an A64 poly(A) sequence. mRNA obtained from this vector accordingly by in vitro transcription is designated as "PpLuc(GC)-A64".

This vector was modified to include untranslated sequences 3' of the open reading frame (3'-UTR). Vectors comprising the following mRNA encoding sequences have been generated (FIGS. 4 to 16 and FIGS. 22 and 23):
SEQ ID NO. 5 (FIG. 4): PpLuc(GC)-A64
SEQ ID NO. 6 (FIG. 5): PpLuc(GC)-albumin-A64
SEQ ID NO. 7 (FIG. 6): PpLuc(GC)-albumin2-A64
SEQ ID NO. 8 (FIG. 7): PpLuc(GC)-albumin3-A64
SEQ ID NO. 9 (FIG. 8): PpLuc(GC)-albumin4-A64
SEQ ID NO. 10 (FIG. 9): PpLuc(GC)-albumin5-A64
SEQ ID NO. 11 (FIG. 10): PpLuc(GC)-albumin6-A64
SEQ ID NO. 12 (FIG. 11): PpLuc(GC)-albumin7-A64
SEQ ID NO. 13 (FIG. 12): PpLuc(GC)-ag-A64
SEQ ID NO. 14 (FIG. 13): PpLuc(GC)-gusb-A64
SEQ ID NO. 15 (FIG. 14): PpLuc(GC)-atp5o-A64
SEQ ID NO. 16 (FIG. 15): PpLuc(GC)-ndufa1-A64
SEQ ID NO. 17 (FIG. 16): PpLuc(GC)-atp5I-A64
SEQ ID NO. 40 (FIG. 22): PpLuc(GC)-albumin8-A64
SEQ ID NO. 41 (FIG. 23): PpLuc(GC)-albumin9-A64
mRNAs used in the examples have been obtained by in vitro transcription of said vectors.

2. In Vitro Transcription

The DNA-template according to Example 1 was linearized and transcribed in vitro using T7-Polymerase. The DNA-template was then digested by DNase-treatment. mRNA transcripts contained a 5'-CAP structure obtained by adding an excess of N7-Methyl-Guanosine-5'-Triphosphate-5'-Guanosine to the transcription reaction. mRNA thus obtained was purified and resuspended in water.

3. Transfection of Cells 3.1 mRNA electroporation

Cells were trypsinized and washed in opti-MEM. $5 \times 10^4$ or $1 \times 10^5$ cells in 200 µl of opti-MEM each were electroporated with 0.3 or 1 µg of PpLuc-encoding mRNA. As a control, mRNA not coding for PpLuc was electroporated separately. In some experiments, mRNA coding for *Renilla reniformis* luciferase (RrLuc) was electroporated together with PpLuc mRNA to control for transfection efficiency (0.1 µg of RrLuc mRNA). Electroporated cells were seeded in 24-well plates in 1 ml of medium. 6, 24, or 48 hours after transfection (or 72 hours in some experiments), medium was aspirated and cells were lysed in 200 µl of lysis buffer (25 mM Tris, pH 7.5 (HCl), 2 mM EDTA, 10% glycerol, 1% Triton X-100, 2 mM DTT, 1 mM PMSF or alternatively Passive Lysis Buffer, Promega). Lysates were stored at −20° C. until luciferase activity was measured.

3.2 mRNA Lipofection

Cells were seeded in 96 well plates three days before transfection (2500 or 5000 cells per well). Immediately before lipofection, cells were washed in opti-MEM. Cells were lipofected with 25 ng of PpLuc-encoding mRNA per well complexed with Lipofectamine2000. mRNA coding for *Renilla reniformis* luciferase (RrLuc) was cotransfected together with PpLuc mRNA to control for transfection efficiency (2.5 ng of RrLuc mRNA per well). 6, 24, 48, or 72 hours after transfection, medium was aspirated and cells were lysed in 100 µl of lysis buffer (Passive Lysis Buffer, Promega). Lysates were stored at −80° C. until luciferase activity was measured.

4. Luciferase Measurement

Luciferase activity was measured as relative light units (RLU) in a BioTek SynergyHT plate reader. PpLuc activity was measured at 5 seconds measuring time using 50 µl of lysate and 200 µl of luciferin buffer (75 µM luciferin, 25 mM Glycylglycin, pH 7.8 (NaOH), 15 mM MgSO4, 2 mM ATP). RrLuc activity was measured at 5 seconds measuring time using 50 µl of lysate and 200 µl of coelenterazin buffer (40 µM coelenterazin, 2.2 mM EDTA, 220 mM $KH_2PO4$/$K_2HPO4$ pH 5.0, 1.1 M NaCl, 1.3 mM $NaN_3$, 0.44 g/l BSA).

Alternatively, luciferase activity was measured as relative light units (RLU) in a Hidex Chameleon plate reader. PpLuc activity was measured at 2 seconds measuring time using 20 µl of lysate and 100 µl of luciferin buffer (Beetle-Juice, PJK GmbH). RrLuc activity was measured at 2 seconds measuring time using 20 µl of lysate and 100 µl of coelenterazin buffer (Renilla-Juice, PJK GmbH).

5. Results 5.1 Albumin 3'-UTR Extends Protein Expression from mRNA Markedly More than the Well-known α-globin 3'-UTR To investigate the effect of 3' untranslated regions on protein expression from mRNA, mRNAs with different 3'-UTRs were synthesized according to Examples 1-2: mRNA contained either the center, α-complex-binding portion of the 3'-UTR of human α-globin (PpLuc(GC)-ag-A64 according to SEQ ID No. 13), since the α-globin 3'-UTR has been reported to stabilize mRNA independent of coding region sequence (Rodgers, N. D., Wang, Z. & Kiledjian, M., 2002. Regulated alpha-globin mRNA decay is a cytoplasmic event proceeding through 3'-to-5' exosome-dependent decapping. *RNA*, 8(12), S.1526-1537.). Alternatively, mRNA contained the 3'-UTR of human albumin (PpLuc (GC)-albumin-A64 according to SEQ ID No. 6). Human albumin mRNA has been reported to be stable (Johnson, T. R. et al., 1991. Newly synthesized RNA: simultaneous measurement in intact cells of transcription rates and RNA stability of insulin-like growth factor I, actin, and albumin in growth hormone-stimulated hepatocytes. Proceedings of the National Academy of Sciences, 88(12), S.5287-5291). Finally, mRNA containing the 3'-UTR of human β-glucuronidase (PpLuc(GC)-gusb-A64 according to SEQ ID No. 14) was used. This human β-glucuronidase mRNA has also been reported to be stable (Watson, G. & Paigen, K., 1987.

Figure 1:
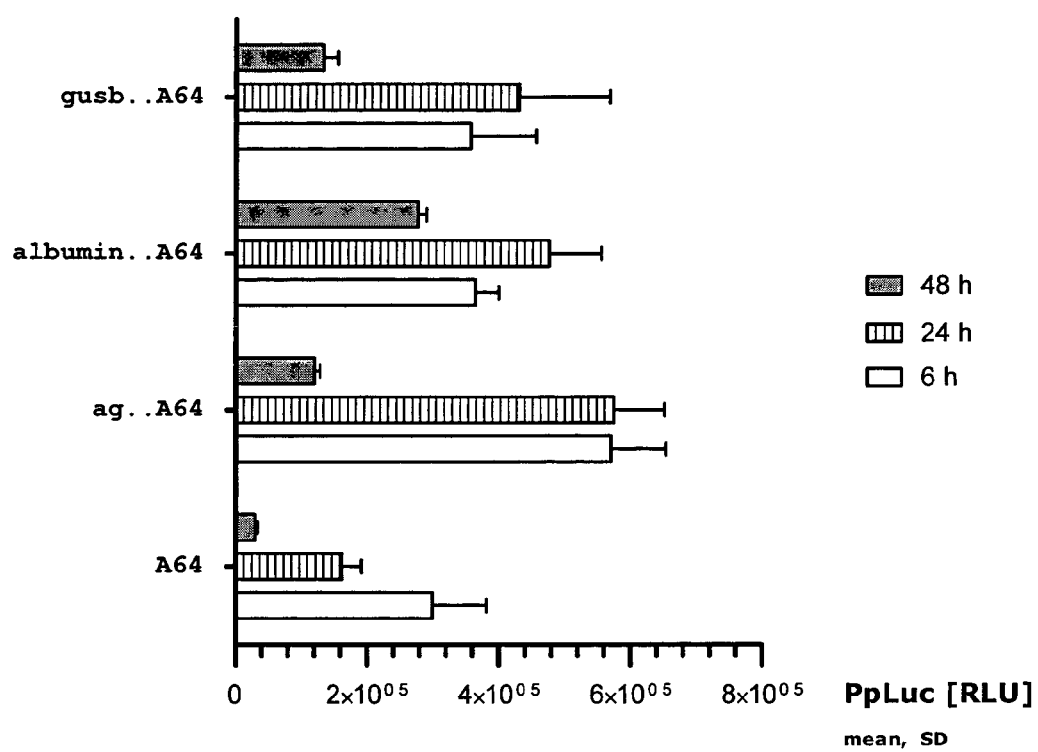

Genetic variations in kinetic constants that describe beta-glucuronidase mRNA induction in androgen-treated mice. Molecular and Cellular Biology, 7(3), S.1085-1090.). For comparison, mRNA lacking a 3'-UTR was also used (PpLuc (GC)-A64 according to SEQ ID No. 5). Luciferase-encoding mRNAs were electroporated into HeLa cells. Luciferase levels were measured at 6, 24, and 48 hours after transfection (see following Table 1 and FIG. 1).

TABLE 1

| mRNA | RLU at 6 hours | RLU at 24 hours | RLU at 48 hours |
| --- | --- | --- | --- |
| PpLuc(GC)-A64 | 299993 | 162445 | 29168 |
| PpLuc(GC)-ag-A64 | 571131 | 574896 | 120029 |
| PpLuc(GC)-albumin-A64 | 364580 | 476567 | 277317 |
| PpLuc(GC)-gusb-A64 | 357513 | 431134 | 134463 |

The luciferase level from mRNA lacking a 3'-UTR dropped from 6 hours to 48 hours, 10% of the 6-hours-signal remaining at 48 hours. The α-globin 3'-UTR stabilized luciferase expression from mRNA only moderately. Strikingly however, the human albumin 3'-UTR further markedly extended luciferase expression from mRNA. In contrast, the 3'-UTR of β-glucuronidase did not extend luciferase expression to the extent observed for the albumin 3'-UTR.

The ratio of the luciferase level at 48 hours and 6 hours, higher figures indicating stabilization of protein expression, was calculated. These data, indicating how much any 3'-UTR stabilized the time course of protein expression, are summarized in Table 2.

TABLE 2

| mRNA | 48 hours RLU/6 hours RLU |
| --- | --- |
| PpLuc(GC)-A64 | 0.10 |
| PpLuc(GC)-ag-A64 | 0.21 |
| PpLuc(GC)-albumin-A64 | 0.76 |
| PpLuc(GC)-gusb-A64 | 0.38 |

The albumin 3'-UTR stabilized protein expression much more than the well-known α-globin 3'-UTR and more than the 3'-UTR of stable β-glucuronidase mRNA. This result demonstrates that the albumin 3'-UTR is particularly efficient at extending protein expression from mRNA.

Figure 2:
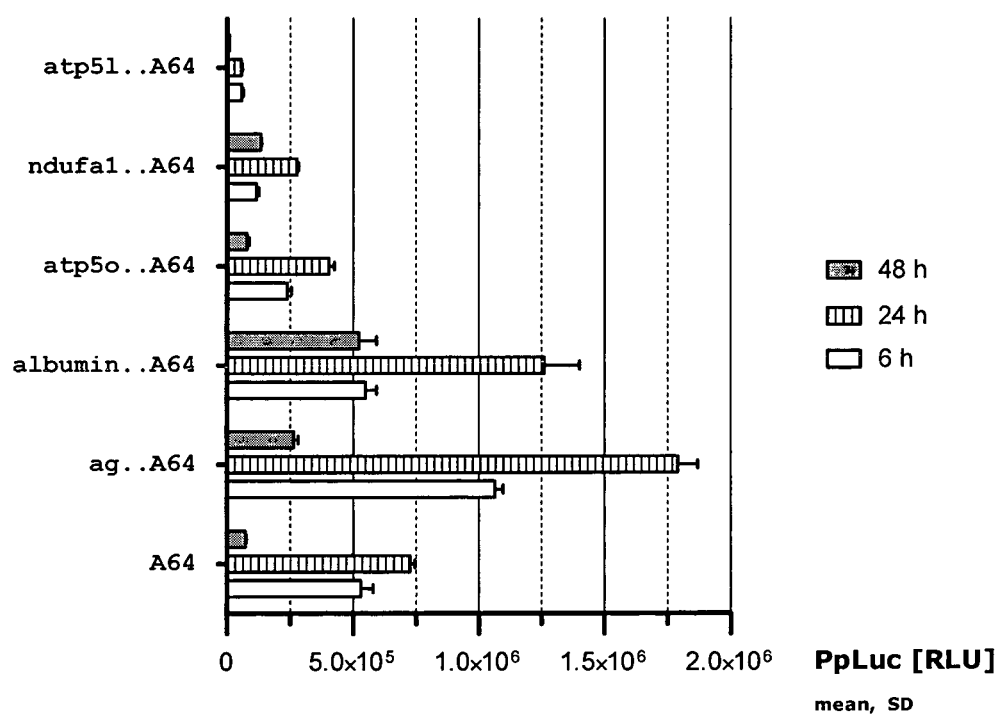

5.2 Albumin 3'-UTR is Unique at Extending Protein Expression While Maintaining Total Protein Expression Extension of protein expression by the albumin 3'-UTR might manifest a generic effect of 3'-UTRs of stable mRNAs (even though the very limited effect of the α-globin 3'-UTR observed in Example 5.1 does not attest to this argument). Thus, mRNAs were synthesized containing the 3'-UTR of the stable mRNAs (Friedel, C. C. et el., 2009. Conserved principles of mammalian transcriptional regulation revealed by RNA half-life. Nucleic Acids Research, 37(17), S.e115.) atp5o or ndufa1 or atp5l (human ATP synthase subunit O, human NADH dehydrogenase [ubiquinone]1α subcomplex subunit 1, or human ATP synthase subunit g, respectively). Luciferase-encoding mRNAs were electroporated into HeLa cells. Luciferase levels were measured at 6, 24, and 48 hours after transfection (see following Table 3 and FIG. 2).

TABLE 3

| mRNA | RLU at 6 hours | RLU at 24 hours | RLU at 48 hours |
| --- | --- | --- | --- |
| PpLuc(GC)-A64 | 529804 | 725602 | 72348 |
| PpLuc(GC)-ag-A64 | 1065036 | 1790023 | 263484 |
| PpLuc(GC)-albumin-A64 | 548821 | 1261832 | 523000 |
| PpLuc(GC)-atp5o-A64 | 239418 | 402629 | 79566 |
| PpLuc(GC)-ndufa1-A64 | 116139 | 277149 | 133723 |
| PpLuc(GC)-atp5l-A64 | 58610 | 56553 | 9728 |

The luciferase level from mRNA lacking a 3'-UTR dropped from 6 hours to 48 hours, 14% of the 6-hours-signal remaining at 48 hours. The α-globin 3'-UTR stabilized luciferase expression from mRNA moderately. Strikingly however, the human albumin 3'-UTR further markedly extended luciferase expression from mRNA. Compared to the albumin 3'-UTR did the 3'-UTRs of several different stable mRNAs affect luciferase expression from mRNA in a much less favourable manner: The atp5o and atp5l 3'-UTRs stabilized luciferase expression much less than the albumin 3'-UTR. In addition reduced the atp5o and the atp5l 3'-UTRs luciferase levels substantially compared to the albumin 3'-UTR. The 3'-UTR of the stable ndufa1 mRNA did stabilize luciferase expression markedly. However, the ndufa1 3'-UTR also reduced luciferase levels substantially.

The ratio of the luciferase level at 48 hours and 6 hours, higher figures indicating stabilization of protein expression, was calculated. These data, indicating how much any 3'-UTR stabilized the time course of protein expression, are summarized in Table 4.

TABLE 4

| mRNA | 48 hours RLU/6 hours RLU |
| --- | --- |
| PpLuc(GC)-A64 | 0.14 |
| PpLuc(GC)-ag-A64 | 0.25 |
| PpLuc(GC)-albumin-A64 | 0.95 |
| PpLuc(GC)-atp5o-A64 | 0.33 |
| PpLuc(GC)-ndufa1-A64 | 1.15 |
| PpLuc(GC)-atp5l-A64 | 0.17 |

The albumin 3'-UTR was unique at extending protein expression while maintaining total protein expression. The albumin 3'-UTR gave rise to substantially higher protein expression at the latest time point compared to the well-known α-globin 3'-UTR and 3'-UTRs of several different stable mRNAs. This result demonstrates that the albumin 3'-UTR is particularly suitable for extending protein expression from mRNA.

Figure 3:
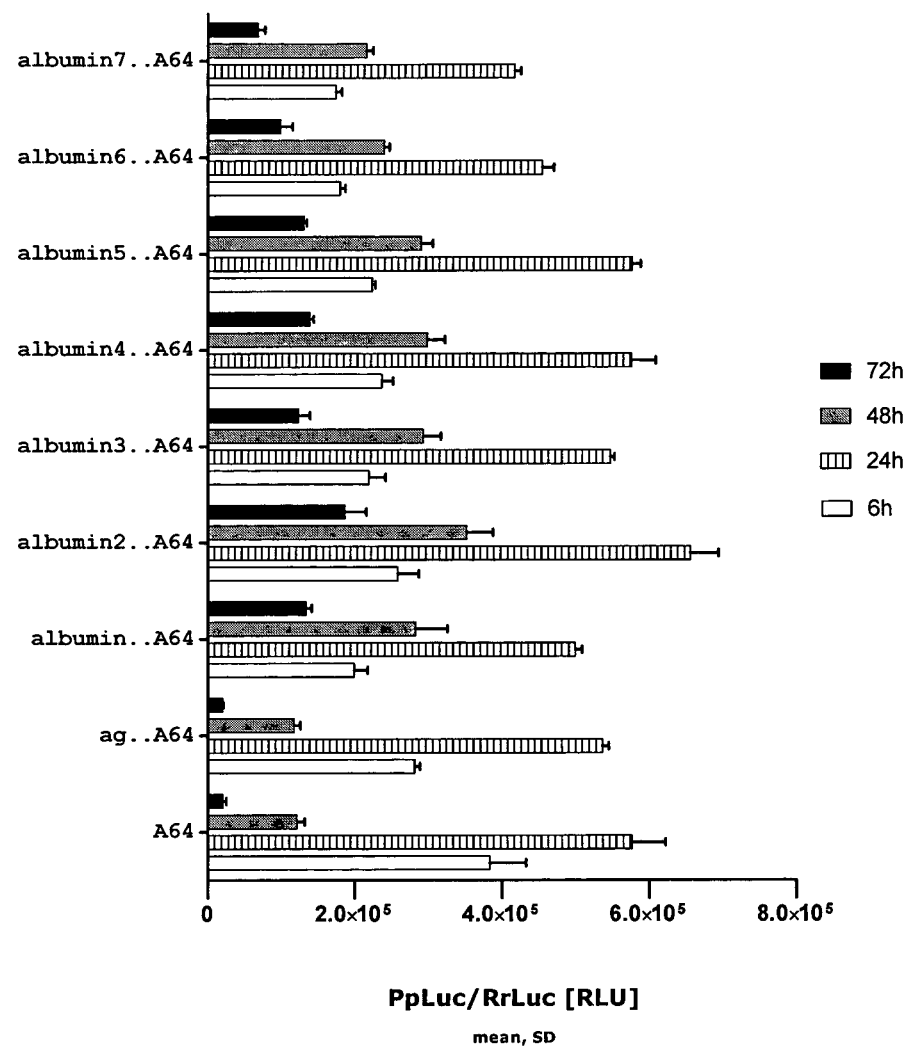

5.3 Different Variants of the Albumin 3'-UTR Extend Protein Expression from mRNA The human albumin 3'-UTR contains a HindIII restriction site, an XbaI restriction site, and a T7 termination signal. Thus, mRNA was synthesized containing variants of the human albumin 3'-UTR with the HindIII and/or the XbaI restriction site and/or the T7 termination signal removed by point mutation(s) (PpLuc(GC)-albumin2-7 according to SEQ ID Nos. 17-12). Luciferase-encoding mRNAs were electroporated into HeLa cells. Luciferase levels were measured at 6, 24, 48, and 72 hours after transfection. The PpLuc Signal was corrected for transfection efficiency by the signal of cotransfected RrLuc (see following Table 5 and FIG. 3).

TABLE 5

| mRNA | RLU at 6 hours | RLU at 24 hours | RLU at 48 hours | RLU at 72 hours |
| --- | --- | --- | --- | --- |
| PpLuc(GC)-A64 | 382909 | 576557 | 122118 | 20962 |
| PpLuc(GC)-ag-A64 | 281262 | 536346 | 118000 | 20356 |
| PpLuc(GC)-albumin-A64 | 199494 | 499804 | 282475 | 134271 |
| PpLuc(GC)-albumin2-A64 | 258516 | 655711 | 351888 | 186869 |
| PpLuc(GC)-albumin3-A64 | 219365 | 547307 | 292511 | 124330 |
| PpLuc(GC)-albumin4-A64 | 236873 | 576151 | 298229 | 139260 |
| PpLuc(GC)-albumin5-A64 | 223815 | 576899 | 289954 | 131145 |
| PpLuc(GC)-albumin6-A64 | 180412 | 455039 | 240086 | 99802 |
| PpLuc(GC)-albumin7-A64 | 174371 | 417171 | 216048 | 68887 |

The ratio of the luciferase level at 72 hours and 6 hours, higher figures indicating stabilization of protein expression, was calculated. These data, indicating how much any 3'-UTR stabilized the time course of protein expression, are summarized in Table 6.

TABLE 6

| mRNA | 72 hours RLU/6 hours RLU |
| --- | --- |
| PpLuc(GC)-A64 | 0.05 |
| PpLuc(GC)-ag-A64 | 0.07 |
| PpLuc(GC)-albumin-A64 | 0.67 |
| PpLuc(GC)-albumin2-A64 | 0.72 |
| PpLuc(GC)-albumin3-A64 | 0.57 |
| PpLuc(GC)-albumin4-A64 | 0.59 |
| PpLuc(GC)-albumin5-A64 | 0.59 |
| PpLuc(GC)-albumin6-A64 | 0.55 |
| PpLuc(GC)-albumin7-A64 | 0.40 |

The luciferase level from mRNA lacking a 3'-UTR dropped from 6 hours to 72 hours, 5% of the 6-hours-signal remaining at 72 hours. The α-globin 3'-UTR stabilized luciferase expression from mRNA only very moderately. In contrast, all variants of the albumin 3'-UTR markedly extended luciferase expression from mRNA.

5.4 Albumin 3'-UTRs of Primates Extend Protein Expression from mRNA

Extension of protein expression by the albumin 3'-UTR might be species-specific. Comparing albumin 3'-UTRs from different primates, the Olive baboon albumin 3'-UTR was least homologous to the human albumin 3'-UTR (Common chimpanzee: 99% identity, Pygmy chimpanzee: 99% identity, Sumatran orang-utan: 99% identity, Olive baboon: 96% identity). Thus, mRNA was synthesized containing the 3'-UTR of the Olive baboon albumin gene (PpLuc(GC)-albumin8-A64 according to SEQ ID No. 40). Luciferase-encoding mRNAs were electroporated into human dermal fibroblasts (HDF). Luciferase levels were measured at 6, 24, 48, and 72 hours after transfection. The PpLuc signal was corrected for transfection efficiency by the signal of cotransfected RrLuc (see following Table 7 and FIG. 18).

TABLE 7

| mRNA | RLU at 6 hours | RLU at 24 hours | RLU at 48 hours | RLU at 72 hours |
| --- | --- | --- | --- | --- |
| PpLuc(GC)-A64 | 130469 | 72629 | 26267 | 6637 |
| PpLuc(GC)-albumin-A64 | 70661 | 74152 | 38209 | 17648 |
| PpLuc(GC)-albumin8-A64 | 71463 | 123361 | 51361 | 18373 |

The ratio of the luciferase level at 72 hours and 6 hours, higher figures indicating stabilization of protein expression, was calculated. These data, indicating how much any 3'-UTR stabilized the time course of protein expression, are summarized in Table 8.

TABLE 8

| mRNA | 72 hours RLU/6 hours RLU |
| --- | --- |
| PpLuc(GC)-A64 | 0.05 |
| PpLuc(GC)-albumin-A64 | 0.25 |
| PpLuc(GC)-albumin8-A64 | 0.26 |

The luciferase level from mRNA lacking a 3'-UTR dropped from 6 hours to 72 hours, 5% of the 6-hours-signal remaining at 72 hours. The human albumin 3'-UTR markedly extended luciferase expression from mRNA. The albumin 3'-UTR from Olive baboon extended luciferase expression from mRNA to the same extent as the human sequence. This result demonstrates that albumin 3'-UTRs from primates are particularly suitable for extending protein expression from mRNA.

Extension of protein expression by both the human and the Olive baboon albumin 3'-UTR was also observed if mRNAs were lipofected rather than electroporated. Luciferase-encoding mRNAs were lipofected into HDF. Luciferase levels were measured at 6, 24, 48, and 72 hours after transfection. The PpLuc signal was corrected for transfection efficiency by the signal of cotransfected RrLuc (see following Table 9 and FIG. 19).

TABLE 9

| mRNA | RLU at 6 hours | RLU at 24 hours | RLU at 48 hours | RLU at 72 hours |
| --- | --- | --- | --- | --- |
| PpLuc(GC)-A64 | 3285 | 7946 | 2725 | 1266 |
| PpLuc(GC)-albumin-A64 | 3743 | 9525 | 5466 | 3381 |
| PpLuc(GC)-albumin8-A64 | 3259 | 7367 | 4044 | 1892 |

The ratios of the luciferase level at 48 hours and 6 hours, higher figures indicating stabilization of protein expression, was calculated. These data, indicating how much any 3'-UTR stabilized the time course of protein expression, are summarized in Table 10.

TABLE 10

| mRNA | 48 hours RLU/6 hours RLU |
| --- | --- |
| PpLuc(GC)-A64 | 0.82 |
| PpLuc(GC)-albumin-A64 | 1.46 |
| PpLuc(GC)-albumin8-A64 | 1.24 |

Upon lipofection rather than electroporation, again both human albumin 3'-UTR and the albumin 3'-UTR from Olive baboon extended luciferase expression from mRNA markedly. This result confirms that albumin 3'-UTRs from primates are particularly suitable for extending protein expression from mRNA.

5.5 Albumin 3'-UTRs of Primates Extend Protein Expression from mRNA in Mouse Cells Extension of protein expression by the albumin 3'-UTR might be species-specific. Thus, it was tested whether the human albumin 3'-UTR and the albumin 3'-UTR from Olive baboon extend luciferase expression from mRNA in mouse cells. Luciferase-encoding mRNAs were lipofected into L-929 cells, a murine fibroblast cell line. Luciferase levels were measured at 6, 24, 48, and 72 hours after transfection. The PpLuc signal was corrected for transfection efficiency by the signal of cotransfected RrLuc (see following Table 11 and FIG. 20).

TABLE 11

| mRNA | RLU at 6 hours | RLU at 24 hours | RLU at 48 hours | RLU at 72 hours |
|---|---|---|---|---|
| PpLuc(GC)-A64 | 177805 | 128658 | 40414 | 12593 |
| PpLuc(GC)-albumin-A64 | 160478 | 244279 | 101177 | 22605 |
| PpLuc(GC)-albumin8-A64 | 151076 | 178839 | 68786 | 16969 |

The ratio of the luciferase level at 48 hours and 6 hours, higher figures indicating stabilization of protein expression, was calculated. These data, indicating how much any 3'-UTR stabilized the time course of protein expression, are summarized in Table 12.

TABLE 12

| mRNA | 48 hours RLU/6 hours RLU |
|---|---|
| PpLuc(GC)-A64 | 0.23 |
| PpLuc(GC)-albumin-A64 | 0.63 |
| PpLuc(GC)-albumin8-A64 | 0.46 |

The luciferase level from mRNA lacking a 3'-UTR dropped from 6 hours to 48 hours, 23% of the 6-hours-signal remaining at 48 hours. The human albumin 3'-UTR markedly extended luciferase expression from mRNA in the mouse cell line. The albumin 3'-UTR from Olive baboon also extended luciferase expression from mRNA in the mouse cell line. This result demonstrates that albumin 3'-UTRs from primates are particularly suitable for extending protein expression from mRNA in mammalian cell types.

5.6 Albumin 3'-UTRs of Mammals Extend Protein Expression from mRNA

Extension of protein expression by the albumin 3'-UTR might be species-specific. Comparing albumin 3'-UTRs from different mammals, the mouse albumin 3'-UTR was least homologous to the human albumin 3'-UTR (Horse: 86% identity, Domestic dog: 84% identity, Cattle: 74% identity, Rat: 73% identity, Mouse: 72% identity). Thus, mRNA was synthesized containing the 3'-UTR of the mouse albumin gene (PpLuc(GC)-albumin9-A64 according to SEQ ID No. 41). Luciferase-encoding mRNAs were lipofected into HeLa cells. Luciferase levels were measured at 6, 24, 48, and 72 hours after transfection. The PpLuc signal was corrected for transfection efficiency by the signal of cotransfected RrLuc (see following Table 13 and FIG. 21).

TABLE 13

| mRNA | RLU at 6 hours | RLU at 24 hours | RLU at 48 hours | RLU at 72 hours |
|---|---|---|---|---|
| PpLuc(GC)-A64 | 46533 | 200168 | 22702 | 3001 |
| PpLuc(GC)-albumin-A64 | 42931 | 224315 | 109190 | 25314 |
| PpLuc(GC)-albumin8-A64 | 39783 | 205950 | 82918 | 17447 |
| PpLuc(GC)-albumin9-A64 | 42500 | 210365 | 60893 | 8380 |

The ratio of the luciferase level at 48 hours and 6 hours, higher figures indicating stabilization of protein expression, was calculated. These data, indicating how much any 3'-UTR stabilized the time course of protein expression, are summarized in Table 14.

TABLE 14

| mRNA | 48 hours RLU/6 hours RLU |
|---|---|
| PpLuc(GC)-A64 | 0.49 |
| PpLuc(GC)-albumin-A64 | 2.54 |
| PpLuc(GC)-albumin8-A64 | 2.08 |
| PpLuc(GC)-albumin9-A64 | 1.43 |

The luciferase level from mRNA lacking a 3'-UTR dropped from 6 hours to 48 hours, 49% of the 6-hours-signal remaining at 48 hours. The human albumin 3'-UTR and the albumin 3'-UTR from Olive baboon markedly extended luciferase expression from mRNA. Importantly, the albumin 3'-UTR from mouse similarly extended luciferase expression from mRNA in the human HeLa cell line. This result demonstrates that albumin 3'-UTRs from mammals are particularly suitable for extending protein expression from mRNA.

```
Sequences:
SEQ ID No. 1:
CATCACATTT AAAAGCATCT CAGCCTACCA TGAGAATAAG AGAAAGAAAA TGAAGATCAA

AAGCTTATTC ATCTGTTTTT CTTTTTCGTT GGTGTAAAGC CAACACCCTG TCTAAAAAAC

ATAAATTTCT TTAATCATTT TGCCTCTTTT CTCTGTGCTT CAATTAATAA AAAATGGAAA

GAATCT

SEQ ID No. 2:
CAUCACAUUU AAAAGCAUCU CAGCCUACCA UGAGAAUAAG AGAAAGAAAA UGAAGAUCAA

AAGCUUAUUC AUCUGUUUUU CUUUUUCGUU GGUGUAAAGC CAACACCCUG UCUAAAAAAC

AUAAAUUUCU UUAAUCAUUU UGCCUCUUUU CUCUGUGCUU CAAUUAAUAA AAAAUGGAAA

GAAUCU

SEQ ID No. 3:
CATCACATTT AAAAGCATCT CAGCCTACCA TGAGAATAAG AGAAAGAAAA TGAAGATCAA

AAGCTTATTC ATCTGTTTTT CTTTTTCGTT GGTGTAAAGC CAACACCCTG TCTAAAAAAC

ATAAATTTCT TTAATCATTT TGCCTCTTTT CTCTGTGCTT CAATTAATAA AAAATGGAAA
```

```
GAATCTAGAT CTAAAAAAAA AAAAAAAAAA AAAAAAAAAA AAAAAAAAAA AAAAAAAAAA

AAAAAAAAAA AAAAA

SEQ ID No. 4:
CAUCACAUUU AAAAGCAUCU CAGCCUACCA UGAGAAUAAG AGAAAGAAAA UGAAGAUCAA

AAGCUUAUUC AUCUGUUUUU CUUUUUCGUU GGUGUAAAGC CAACACCCUG UCUAAAAAAC

AUAAAUUUCU UUAAUCAUUU UGCCUCUUUU CUCUGUGCUU CAAUUAAUAA AAAAUGGAAA

GAAUCUAGAU CUAAAAAAAA AAAAAAAAAA AAAAAAAAAA AAAAAAAAAA AAAAAAAAAA

AAAAAAAAAA AAAAA

SEQ ID No. 5:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTAGAT

CTAAAAAAAAAAAAAAAAAAAAAAAAAAAAAAAAAAAAAAAAAAAAAAAAAAAAAA

AAAAAA

SEQ ID No. 6:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT
```

-continued

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTGCAT

CACATTTAAAAGCATCTCAGCCTACCATGAGAATAAGAGAAAGAAAATGAAGATCAAAAG

CTTATTCATCTGTTTTTCTTTTTCGTTGGTGTAAAGCCAACACCCTGTCTAAAAAACATA

AATTTCTTTAATCATTTTGCCTCTTTTCTCTGTGCTTCAATTAATAAAAAATGGAAAGAA

TCTAGATCTAAAAAAAAAAAAAAAAAAAAAAAAAAAAAAAAAAAAAAAAAAAAAAAAAAA

AAAAAAAAAAAA

SEQ ID No. 7:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

-continued
CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTGCAT

CACATTTAAAAGCATCTCAGCCTACCATGAGAATAAGAGAAAGAAAATGAAGATCAAAAG

CTTATTCGTCTGTTTTTCTTTTTCGTTGGTGTAAAGCCAACACCCTGTCTAAAAAACATA

AATTTCTTTAATCATTTTGCCTCTTTTCTCTGTGCTTCAATTAATAAAAAATGGAAAGAA

TCTAGATCTAAAAAAAAAAAAAAAAAAAAAAAAAAAAAAAAAAAAAAAAAAAAAAAAAAA

AAAAAAAAAAAA

SEQ ID No. 8:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

-continued

```
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
GAGCATCCTGCTCCAGCACCCCAACATCTTCGACGCCGGCGTGGCCGGGCTGCCGGACGA
CGACGCCGGCGAGCTGCCGGCCGCGGTGGTGGTGCTGGAGCACGGCAAGACCATGACGGA
GAAGGAGATCGTCGACTACGTGGCCAGCCAGGTGACCACCGCCAAGAAGCTGCGGGGCGG
CGTGGTGTTCGTGGACGAGGTCCCGAAGGGCCTGACCGGGAAGCTCGACGCCCGGAAGAT
CCGCGAGATCCTGATCAAGGCCAAGAAGGGCGGCAAGATCGCCGTGTAAGACTAGTGCAT
CACATTTAAAAGCATCTCAGCCTACCATGAGAATAAGAGAAAGAAAATGAAGATCAAAAG
CTTATTCATCAGTTTTTCTTTTTCGTTGGTGTAAAGCCAACACCCTGTCTAAAAAACATA
AATTTCTTTAATCATTTTGCCTCTTTTCTCTGTGCTTCAATTAATAAAAAATGGAAAGAA
TCTAGATCTAAAAAAAAAAAAAAAAAAAAAAAAAAAAAAAAAAAAAAAAAAAAAAAAAAA
AAAAAAAAAAAA
SEQ ID No. 9:
GGGAGAAAGCTTGAGGATGGAGGACGCCAAGAACATCAAGAAGGGCCCGGCGCCCTTCTA
CCCGCTGGAGGACGGGACCGCCGGCGAGCAGCTCCACAAGGCCATGAAGCGGTACGCCCT
GGTGCCGGGCACGATCGCCTTCACCGACGCCCACATCGAGGTCGACATCACCTACGCGGA
GTACTTCGAGATGAGCGTGCGCCTGGCCGAGGCCATGAAGCGGTACGGCCTGAACACCAA
CCACCGGATCGTGGTGTGCTCGGAGAACAGCCTGCAGTTCTTCATGCCGGTGCTGGGCGC
CCTCTTCATCGGCGTGGCCGTCGCCCCGGCGAACGACATCTACAACGAGCGGGAGCTGCT
GAACAGCATGGGGATCAGCCAGCCGACCGTGGTGTTCGTGAGCAAGAAGGGCCTGCAGAA
GATCCTGAACGTGCAGAAGAAGCTGCCCATCATCCAGAAGATCATCATCATGGACAGCAA
GACCGACTACCAGGGCTTCCAGTCGATGTACACGTTCGTGACCAGCCACCTCCCGCCGGG
CTTCAACGAGTACGACTTCGTCCCGGAGAGCTTCGACCGGGACAAGACCATCGCCCTGAT
CATGAACAGCAGCGGCAGCACCGGCCTGCCGAAGGGGGTGGCCCTGCCGCACCGGACCGC
CTGCGTGCGCTTCTCGCACGCCCGGGACCCCATCTTCGGCAACCAGATCATCCCGGACAC
CGCCATCCTGAGCGTGGTGCCGTTCCACCACGGCTTCGGCATGTTCACGACCCTGGGCTA
CCTCATCTGCGGCTTCCGGGTGGTCCTGATGTACCGGTTCGAGGAGGAGCTGTTCCTGCG
GAGCCTGCAGGACTACAAGATCCAGAGCGCGCTGCTCGTGCCGACCCTGTTCAGCTTCTT
CGCCAAGAGCACCCTGATCGACAAGTACGACCTGTCGAACCTGCACGAGATCGCCAGCGG
GGGCGCCCCGCTGAGCAAGGAGGTGGGCGAGGCCGTGGCCAAGCGGTTCCACCTCCCGGG
CATCCGCCAGGGCTACGGCCTGACCGAGACCACGAGCGCGATCCTGATCACCCCCGAGGG
GGACGACAAGCCGGGCGCCGTGGGCAAGGTGGTCCCGTTCTTCGAGGCCAAGGTGGTGGA
CCTGGACACCGGCAAGACCCTGGGCGTGAACCAGCGGGGCGAGCTGTGCGTGCGGGGGCC
GATGATCATGAGCGGCTACGTGAACAACCCGGAGGCCACCAACGCCCTCATCGACAAGGA
CGGCTGGCTGCACAGCGGCGACATCGCCTACTGGGACGAGGACGAGCACTTCTTCATCGT
CGACCGGCTGAAGTCGCTGATCAAGTACAAGGGCTACCAGGTGGCGCCGGCCGAGCTGGA
```

-continued

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTGCAT

CACATTTAAAAGCATCTCAGCCTACCATGAGAATAAGAGAAAGAAAATGAAGATCAAAAG

CTTATTCATCTCTTTTTCTTTTTCGTTGGTGTAAAGCCAACACCCTGTCTAAAAAACATA

AATTTCTTTAATCATTTTGCCTCTTTTCTCTGTGCTTCAATTAATAAAAAATGGAAAGAA

TCTAGATCTAAAAAAAAAAAAAAAAAAAAAAAAAAAAAAAAAAAAAAAAAAAAAAAAAAA

AAAAAAAAAAAA

SEQ ID No. 10:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTGCAT

CACATTTAAAAGCATCTCAGCCTACCATGAGAATAAGAGAAAGAAAATGAAGATCAAAAG

CTTATTCATCTGTTGGTCTTTTTCGTTGGTGTAAAGCCAACACCCTGTCTAAAAAACATA

AATTTCTTTAATCATTTTGCCTCTTTTCTCTGTGCTTCAATTAATAAAAAATGGAAAGAA

TCTAGATCTAAAAAAAAAAAAAAAAAAAAAAAAAAAAAAAAAAAAAAAAAAAAAAAAAAA

AAAAAAAAAAAA

SEQ ID No. 11:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTGCAT

CACATTTAAAAGCATCTCAGCCTACCATGAGAATAAGAGAAAGAAAATGAAGATCAATAG

CTTATTCATCTGTTTTTCTTTTCGTTGGTGTAAAGCCAACACCCTGTCTAAAAAACATA

AATTTCTTTAATCATTTTGCCTCTTTTCTCTGTGCTTCAATTAATAAAAAATGGAAAGAA

CCTAGATCTAAAAAAAAAAAAAAAAAAAAAAAAAAAAAAAAAAAAAAAAAAAAAAAAAAA

AAAAAAAAAAAA

SEQ ID No. 12:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

-continued

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTGCAT

CACATTTAAAAGCATCTCAGCCTACCATGAGAATAAGAGAAAGAAAATGAAGATCAATAG

CTTATTCATCTCTTTTTCTTTTTCGTTGGTGTAAAGCCAACACCCTGTCTAAAAAACATA

AATTTCTTTAATCATTTTGCCTCTTTTCTCTGTGCTTCAATTAATAAAAAATGGAAAGAA

CCTAGATCTAAAAAAAAAAAAAAAAAAAAAAAAAAAAAAAAAAAAAAAAAAAAAAAAAAA

AAAAAAAAAAAA

SEQ ID No. 13:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

-continued

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTTATA

AGACTGACTAGCCCGATGGGCCTCCCAACGGGCCCTCCTCCCCTCCTTGCACCGAGATTA

ATAGATCTAAAAAAAAAAAAAAAAAAAAAAAAAAAAAAAAAAAAAAAAAAAAAAAAAAAA

AAAAAAAAAAAA

SEQ ID No. 14:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTGCAA

GACTGATACCACCTGCGTGTCCCTTCCTCCCCGAGTCAGGGCGACTTCCACAGCAGCAGA

ACAAGTGCCTCCTGGACTGTTCACGGCAGACCAGAACGTTTCTGGCCTGGGTTTTGTGGT

CATCTATTCTAGCAGGGAACACTAAAGGTGGAAATAAAAGATTTTCTATTATGGAAATAA

AGAGTTGGCATGAAAGTGGCTACTGAGATCTAAAAAAAAAAAAAAAAAAAAAAAAAAAAA

AAAAAAAAAAAAAAAAAAAAAAAAAAAAAAAA

SEQ ID No. 15:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

```
CCGCGAGATCCTGATCAAGGCCAAGAAGGGCGGCAAGATCGCCGTGTAAGACTAGTAAGT

GTTGGTTTTCTGCCATCAGTGAAAATTCTTAAACTTGGAGCAACAATAAAAAGCTTCCAG

AACAGATCAGATCTAAAAAAAAAAAAAAAAAAAAAAAAAAAAAAAAAAAAAAAAAAAAAA

AAAAAAAAAAAAAAAAA

SEQ ID No. 16:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA

GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTGGAA

GCATTTTCCTGATTGATGAAAAAAATAACTCAGTTATGGCCATCTACCCCTGCTAGAAGG

TTACAGTGTATTATGTAGCATGCAATGTGTTATGTAGTGCTTAATAAAAATAAATGAAA

AAAATGCAGATCTAAAAAAAAAAAAAAAAAAAAAAAAAAAAAAAAAAAAAAAAAAAAAA

AAAAAAAAAAAAAAAA

SEQ ID No. 17:
GGGAGAAAGCTTGAGGATGGAGGACGCCAAGAACATCAAGAAGGGCCCGGCGCCCTTCTA

CCCGCTGGAGGACGGGACCGCCGGCGAGCAGCTCCACAAGGCCATGAAGCGGTACGCCCT

GGTGCCGGGCACGATCGCCTTCACCGACGCCCACATCGAGGTCGACATCACCTACGCGGA
```

-continued

```
GTACTTCGAGATGAGCGTGCGCCTGGCCGAGGCCATGAAGCGGTACGGCCTGAACACCAA

CCACCGGATCGTGGTGTGCTCGGAGAACAGCCTGCAGTTCTTCATGCCGGTGCTGGGCGC

CCTCTTCATCGGCGTGGCCGTCGCCCCGGCGAACGACATCTACAACGAGCGGGAGCTGCT

GAACAGCATGGGGATCAGCCAGCCGACCGTGGTGTTCGTGAGCAAGAAGGGCCTGCAGAA

GATCCTGAACGTGCAGAAGAAGCTGCCCATCATCCAGAAGATCATCATCATGGACAGCAA

GACCGACTACCAGGGCTTCCAGTCGATGTACACGTTCGTGACCAGCCACCTCCCGCCGGG

CTTCAACGAGTACGACTTCGTCCCGGAGAGCTTCGACCGGGACAAGACCATCGCCCTGAT

CATGAACAGCAGCGGCAGCACCGGCCTGCCGAAGGGGGTGGCCCTGCCGCACCGGACCGC

CTGCGTGCGCTTCTCGCACGCCCGGGACCCCATCTTCGGCAACCAGATCATCCCGGACAC

CGCCATCCTGAGCGTGGTGCCGTTCCACCACGGCTTCGGCATGTTCACGACCCTGGGCTA

CCTCATCTGCGGCTTCCGGGTGGTCCTGATGTACCGGTTCGAGGAGGAGCTGTTCCTGCG

GAGCCTGCAGGACTACAAGATCCAGAGCGCGCTGCTCGTGCCGACCCTGTTCAGCTTCTT

CGCCAAGAGCACCCTGATCGACAAGTACGACCTGTCGAACCTGCACGAGATCGCCAGCGG

GGGCGCCCCGCTGAGCAAGGAGGTGGGCGAGGCCGTGGCCAAGCGGTTCCACCTCCCGGG

CATCCGCCAGGGCTACGGCCTGACCGAGACCACGAGCGCGATCCTGATCACCCCCGAGGG

GGACGACAAGCCGGGCGCCGTGGGCAAGGTGGTCCCGTTCTTCGAGGCCAAGGTGGTGGA

CCTGGACACCGGCAAGACCCTGGGCGTGAACCAGCGGGGCGAGCTGTGCGTGCGGGGGCC

GATGATCATGAGCGGCTACGTGAACAACCCGGAGGCCACCAACGCCCTCATCGACAAGGA

CGGCTGGCTGCACAGCGGCGACATCGCCTACTGGGACGAGGACGAGCACTTCTTCATCGT

CGACCGGCTGAAGTCGCTGATCAAGTACAAGGGCTACCAGGTGGCGCCGGCCGAGCTGGA

GAGCATCCTGCTCCAGCACCCCAACATCTTCGACGCCGGCGTGGCCGGGCTGCCGGACGA

CGACGCCGGCGAGCTGCCGGCCGCGGTGGTGGTGCTGGAGCACGGCAAGACCATGACGGA

GAAGGAGATCGTCGACTACGTGGCCAGCCAGGTGACCACCGCCAAGAAGCTGCGGGGCGG

CGTGGTGTTCGTGGACGAGGTCCCGAAGGGCCTGACCGGGAAGCTCGACGCCCGGAAGAT

CCGCGAGATCCTGATCAAGGCCAAGAAGGGCGGCAAGATCGCCGTGTAAGACTAGTAGAC

CAATCTTTAACATCTGATTATATTTGATTTATTATTTGAGTGTTGTTGGACCATGTGTGA

TCAGACTGCTATCTGAATAAAATAAGATTTGTCAAAACTCAGTGTTTTCTCCATCAGACA

CTCCATGAAAGGTCACAATTTCTCTTGATATTAAGCTGGGTTGTCTTTAAACAACCCTAA

ATACACGTCTGTTTAGCCCGCAATTGGAAAGGATATATGTGGCAATATTAACCTGGTACA

TGAATATATGGGGATAACATTTTAATTTGAAGGTTTGGAATATATATATTTAAGCTTTAT

TTCCAGAACAGTGAGGGTTAGGTCTTGGGAAAACTATAACTTGCCAAAGTAGAAGAAATA

GTAGTACCATATGCCAAAGTGATAGAGATGAATCATGTCAGTAGTTAGAATAACATTTCA

ACTGTTTTCTTTGCTAAAATCACAGAAAGACCCTATTGACAACATCTATGTCTGTAAAAA

TGTTAGAGTACTTGTCATCTTGAATATAGCCTCCCCAAGAGAGAACAGGGTGGTATTCTA

AGTATGTTTCTTTGTAACATCTTTAGCAGTAGGACAGAGCCATACATGTGAAATCTGATT

TTTATGTGTGTTATTCGTTTGTCTGGTTTTACTACCTTTGCAAAAACAAAATACCCCAAA

GATATTTAAACAAGGTTATAATTTAGCATCTTCCCTGGATCTAAATAGTATATTATATCC

TGAAATAAATGAAATGATTGCTATAGATCTAAAAAAAAAAAAAAAAAAAAAAAAAAAAAA

AAAAAAAAAAAAAAAAAAAAAAAAAAAAAAAA
```

SEQ ID No. 18:
AAAAGCATCT CAGCCTACCA TGAGAATAAG AGAAAGAAAA TGAAGATCAA AAGCTTATTC

ATCTGTTTTT CTTTTTCGTT GGTGTAAAGC CAACACCCTG TCTAAAAAAC ATAAATTTCT

TTAATCATTT TGCCTCTTTT CTCTGTGCTT CAATT

SEQ ID No. 19:
CATCACATTT AAAAGCATCT CAGCCTACCA TGAGAATAAG AGAAAGAAAA TGAAGATCAA

AAGCTTATTC ATCTGTTTTT CTTTTTCGTT GGTGTAAAGC CAACACCCTG

SEQ ID No. 20:
AAAAGCATCT CAGCCTACCA TGAGAATAAG AGAAAGAAAA TGAAGATCAA AAGCTTATTC

ATCTGTTTTT CTTTTTCGTT GGTGTAAAGC CAACACCCTG TCTAAAAAAC

SEQ ID No. 21:
CAGCCTACCA TGAGAATAAG AGAAAGAAAA TGAAGATCAA AAGCTTATTC ATCTGTTTTT

CTTTTTCGTT GGTGTAAAGC CAACACCCTG TCTAAAAAAC ATAAATTTCT

SEQ ID No. 22:
TGAGAATAAG AGAAAGAAAA TGAAGATCAA AAGCTTATTC ATCTGTTTTT CTTTTTCGTT

GGTGTAAAGC CAACACCCTG TCTAAAAAAC ATAAATTTCT TTAATCATTT

SEQ ID No. 23:
AGAAAGAAAA TGAAGATCAA AAGCTTATTC ATCTGTTTTT CTTTTTCGTT GGTGTAAAGC

CAACACCCTG TCTAAAAAAC ATAAATTTCT TTAATCATTT TGCCTCTTTT

SEQ ID No. 24:
TGAAGATCAA AAGCTTATTC ATCTGTTTTT CTTTTTCGTT GGTGTAAAGC CAACACCCTG

TCTAAAAAAC ATAAATTTCT TTAATCATTT TGCCTCTTTT CTCTGTGCTT

SEQ ID No. 25:
AAGCTTATTC ATCTGTTTTT CTTTTTCGTT GGTGTAAAGC CAACACCCTG TCTAAAAAAC

ATAAATTTCT TTAATCATTT TGCCTCTTTT CTCTGTGCTT CAATTAATAA

SEQ ID No. 26:
ATCTGTTTTT CTTTTTCGTT GGTGTAAAGC CAACACCCTG TCTAAAAAAC ATAAATTTCT

TTAATCATTT TGCCTCTTTT CTCTGTGCTT CAATTAATAA AAAATGGAAA

SEQ ID No. 27:
CAGCCTACCA TGAGAATAAG AGAAAGAAAA TGAAGATCAA AAGCTTATTC ATCTGTTTTT

CTTTTTCGTT GGTGTAAAGC CAACACCCTG TCTAAAAAAC ATAAATTTCT TTAATCATTT

TGCCTCTTTT CTCTGTGCTT CAATTAATAA A

SEQ ID No. 28:
TGAAGATCAA AAGCTTATTC ATCTGTTTTT CTTTTTCGTT GGTGTAAAGC CAACACCCTG

TCTAAAAAAC ATAAATTTCT TTAATCATTT TGCCTCTTTT CTCTGTGCTT CAATTAATAA

A

SEQ ID No. 29:
CTTTTTCGTT GGTGTAAAGC CAACACCCTG TCTAAAAAAC ATAAATTTCT TTAATCATTT

TGCCTCTTTT CTCTGTGCTT CAATTAATAA A

SEQ ID No. 30:
AAGCTTATTC ATCTGTTTTT CTTTTTCGTT GGTGTAAAGC CAACACCCTG TCTAAAAAAC

SEQ ID No. 31:
CAAAGGCTCTTTTCAGAGCCACCA

SEQ ID No. 32:
AAACATCACA ATTAAGAACA TCTCAGCCTA CCATGAGAAC AAGAGAAATA AAATGAAGAT

CAAAAGCTTA TTCATCTGTT TTTCTTTTTC ATTGGTATAA AGCCAACACC CTGTCTAAAA

```
-continued
AACTATAAAT TTCTTTAATC ATTTTGCCTC TTTTCTCTGT GCTTCAATTA ATAAAAAATG

GAAAGAATCT AGATCTAAAA AAAAAAAAAA AAAAAAAAA AAAAAAAAAA AAAAAAAAA

AAAA

SEQ ID No. 33:
AAACAUCACA AUUAAGAACA UCUCAGCCUA CCAUGAGAAC AAGAGAAAUA AAAUGAAGAU

CAAAAGCUUA UUCAUCUGUU UUUCUUUUUC AUUGGUAUAA AGCCAACACC CUGUCUAAAA

AACUAUAAAU UUCUUUAAUC AUUUUGCCUC UUUUCUCUGU GCUUCAAUUA AUAAAAAAUG

GAAAGAAUCU AGAUCUAAAA AAAAAAAAAA AAAAAAAAAA AAAAAAAAAA AAAAAAAAA

AAAA

SEQ ID No. 34:
ACACATCACA ACCACAACCT TCTCAGGCTA CCCTGAGAAA AAAAGACATG AAGACTCAGG

ACTCATCTTT TCTGTTGGTG TAAAATCAAC ACCCTAAGGA ACACAAATTT CTTTAAACAT

TTGACTTCTT GTCTCTGTGC TGCAATTAAT AAAAAATGGA AAGAATCTAC AGATCTAAAA

AAAA

SEQ ID No. 35:
ACACAUCACA ACCACAACCU UCUCAGGCUA CCCUGAGAAA AAAAGACAUG AAGACUCAGG

ACUCAUCUUU UCUGUUGGUG UAAAAUCAAC ACCCUAAGGA ACACAAAUUU CUUUAAACAU

UUGACUUCUU GUCUCUGUGC UGCAAUUAAU AAAAAAUGGA AAGAAUCUAC AGAUCUAAAA

AAAA

SEQ ID No. 36:
AAACATCACA ATTAAGAACA TCTCAGCCTA CCATGAGAAC AAGAGAAATA

AAATGAAGAT CAAAAGCTTA TTCATCTGTT TTTCTTTTTC ATTGGTATAA AGCCAACACC

CTGTCTAAAA AACTATAAAT TTCTTTAATC ATTTTGCCTC TTTTCTCTGT GCTTCAATTA

ATAAAAAATG GAAAGAATCT AGATCTAAAA AAAAAAAAAA AAAAAAAAAA AAAAAAAAA

AAAAAAAAAA AAAAAAAAAA AAAAAAAAA

SEQ ID No. 37:
AAACAUCACA AUUAAGAACA UCUCAGCCUA CCAUGAGAAC AAGAGAAAUA AAAUGAAGAU

CAAAAGCUUA UUCAUCUGUU UUUCUUUUUC AUUGGUAUAA AGCCAACACC CUGUCUAAAA

AACUAUAAAU UUCUUTAAUC AUUUUGCCUC TTTTCTCTGT GCTTCAATTA ATAAAAAATG

GAAAGAATCT AGATCTAAAA AAAAAAAAAA AAAAAAAAAA AAAAAAAAA AAAAAAAAA

AAAAAAAAAA AAAAAAAAA

SEQ ID No. 38:
ACACATCACA ACCACAACCT TCTCAGGCTA CCCTGAGAAA AAAAGACATG AAGACTCAGG

ACTCATCTTT TCTGTTGGTG TAAAATCAAC ACCCTAAGGA ACACAAATTT CTTTAAACAT

TTGACTTCTT GTCTCTGTGC TGCAATTAAT AAAAAATGGA AAGAATCTAC AGATCTAAAA

AAAAAAAAAA AAAAAAAAAA AAAAAAAAA AAAAAAAAAA AAAAAAAAAA AAAAAAAAA

SEQ ID No. 39:
ACACAUCACA ACCACAACCU UCUCAGGCUA CCCUGAGAAA AAAAGACAUG AAGACUCAGG

ACUCAUCUUU UCUGUUGGUG UAAAAUCAAC ACCCUAAGGA ACACAAAUUU CUUUAAACAU

UUGACUUCUU GUCUCUGUGC UGCAAUUAAU AAAAAAUGGA AAGAAUCUAC AGAUCUAAAA

AAAAAAAAAA AAAAAAAAAA AAAAAAAAA AAAAAAAAAA AAAAAAAAAA AAAAAAAAA

SEQ ID No. 40:
GGGAGAAAGC TTGAGGATGG AGGACGCCAA GAACATCAAG AAGGGCCCGG CGCCCTTCTA

CCCGCTGGAG GACGGGACCG CCGGCGAGCA GCTCCACAAG GCCATGAAGC GGTACGCCCT

GGTGCCGGGC ACGATCGCCT TCACCGACGC CCACATCGAG GTCGACATCA CCTACGCGGA
```

```
GTACTTCGAG ATGAGCGTGC GCCTGGCCGA GGCCATGAAG CGGTACGGCC TGAACACCAA

CCACCGGATC GTGGTGTGCT CGGAGAACAG CCTGCAGTTC TTCATGCCGG TGCTGGGCGC

CCTCTTCATC GGCGTGGCCG TCGCCCCGGC GAACGACATC TACAACGAGC GGGAGCTGCT

GAACAGCATG GGGATCAGCC AGCCGACCGT GGTGTTCGTG AGCAAGAAGG GCCTGCAGAA

GATCCTGAAC GTGCAGAAGA AGCTGCCCAT CATCCAGAAG ATCATCATCA TGGACAGCAA

GACCGACTAC CAGGGCTTCC AGTCGATGTA CACGTTCGTG ACCAGCCACC TCCCGCCGGG

CTTCAACGAG TACGACTTCG TCCCGGAGAG CTTCGACCGG GACAAGACCA TCGCCCTGAT

CATGAACAGC AGCGGCAGCA CCGGCCTGCC GAAGGGGGTG GCCCTGCCGC ACCGGACCGC

CTGCGTGCGC TTCTCGCACG CCCGGGACCC CATCTTCGGC AACCAGATCA TCCCGGACAC

CGCCATCCTG AGCGTGGTGC CGTTCCACCA CGGCTTCGGC ATGTTCACGA CCCTGGGCTA

CCTCATCTGC GGCTTCCGGG TGGTCCTGAT GTACCGGTTC GAGGAGGAGC TGTTCCTGCG

GAGCCTGCAG GACTACAAGA TCCAGAGCGC GCTGCTCGTG CCGACCCTGT TCAGCTTCTT

CGCCAAGAGC ACCCTGATCG ACAAGTACGA CCTGTCGAAC CTGCACGAGA TCGCCAGCGG

GGGCGCCCCG CTGAGCAAGG AGGTGGGCGA GGCCGTGGCC AAGCGGTTCC ACCTCCCGGG

CATCCGCCAG GGCTACGGCC TGACCGAGAC CACGAGCGCG ATCCTGATCA CCCCCGAGGG

GGACGACAAG CCGGGCGCCG TGGGCAAGGT GGTCCCGTTC TTCGAGGCCA AGGTGGTGGA

CCTGGACACC GGCAAGACCC TGGGCGTGAA CCAGCGGGGC GAGCTGTGCG TGCGGGGCCC

GATGATCATG AGCGGCTACG TGAACAACCC GGAGGCCACC AACGCCCTCA TCGACAAGGA

CGGCTGGCTG CACAGCGGCG ACATCGCCTA CTGGGACGAG GACGAGCACT TCTTCATCGT

CGACCGGCTG AAGTCGCTGA TCAAGTACAA GGGCTACCAG GTGGCGCCGG CCGAGCTGGA

GAGCATCCTG CTCCAGCACC CCAACATCTT CGACGCCGGC GTGGCCGGGC TGCCGGACGA

CGACGCCGGC GAGCTGCCGG CCGCGGTGGT GGTGCTGGAG CACGGCAAGA CCATGACGGA

GAAGGAGATC GTCGACTACG TGGCCAGCCA GGTGACCACC GCCAAGAAGC TGCGGGGCGG

CGTGGTGTTC GTGGACGAGG TCCCGAAGGG CCTGACCGGG AAGCTCGACG CCCGGAAGAT

CCGCGAGATC CTGATCAAGG CCAAGAAGGG CGGCAAGATC GCCGTGTAAG ACTAGTAAAC

ATCACAATTA AGAACATCTC AGCCTACCAT GAGAACAAGA GAAATAAAAT GAAGATCAAA

AGCTTATTCA TCTGTTTTTC TTTTTCATTG GTATAAAGCC AACACCCTGT CTAAAAAACT

ATAAATTTCT TTAATCATTT TGCCTCTTTT CTCTGTGCTT CAATTAATAA AAAATGGAAA

GAATCTAGAT CTAAAAAAAA AAAAAAAAAA AAAAAAAAAA AAAAAAAAAA AAAAAAAAAA

AAAAAAAAAA AAAAAA
SEQ ID No. 41:
GGGAGAAAGC TTGAGGATGG AGGACGCCAA GAACATCAAG AAGGGCCCGG CGCCCTTCTA

CCCGCTGGAG GACGGGACCG CCGGCGAGCA GCTCCACAAG GCCATGAAGC GGTACGCCCT

GGTGCCGGGC ACGATCGCCT TCACCGACGC CCACATCGAG GTCGACATCA CCTACGCGGA

GTACTTCGAG ATGAGCGTGC GCCTGGCCGA GGCCATGAAG CGGTACGGCC TGAACACCAA

CCACCGGATC GTGGTGTGCT CGGAGAACAG CCTGCAGTTC TTCATGCCGG TGCTGGGCGC

CCTCTTCATC GGCGTGGCCG TCGCCCCGGC GAACGACATC TACAACGAGC GGGAGCTGCT

GAACAGCATG GGGATCAGCC AGCCGACCGT GGTGTTCGTG AGCAAGAAGG GCCTGCAGAA

GATCCTGAAC GTGCAGAAGA AGCTGCCCAT CATCCAGAAG ATCATCATCA TGGACAGCAA

GACCGACTAC CAGGGCTTCC AGTCGATGTA CACGTTCGTG ACCAGCCACC TCCCGCCGGG

CTTCAACGAG TACGACTTCG TCCCGGAGAG CTTCGACCGG GACAAGACCA TCGCCCTGAT
```

```
CATGAACAGC AGCGGCAGCA CCGGCCTGCC GAAGGGGGTG GCCCTGCCGC ACCGGACCGC

CTGCGTGCGC TTCTCGCACG CCCGGGACCC CATCTTCGGC AACCAGATCA TCCCGGACAC

CGCCATCCTG AGCGTGGTGC CGTTCCACCA CGGCTTCGGC ATGTTCACGA CCCTGGGCTA

CCTCATCTGC GGCTTCCGGG TGGTCCTGAT GTACCGGTTC GAGGAGGAGC TGTTCCTGCG

GAGCCTGCAG GACTACAAGA TCCAGAGCGC GCTGCTCGTG CCGACCCTGT TCAGCTTCTT

CGCCAAGAGC ACCCTGATCG ACAAGTACGA CCTGTCGAAC CTGCACGAGA TCGCCAGCGG

GGGCGCCCCG CTGAGCAAGG AGGTGGGCGA GGCCGTGGCC AAGCGGTTCC ACCTCCCGGG

CATCCGCCAG GGCTACGGCC TGACCGAGAC CACGAGCGCG ATCCTGATCA CCCCCGAGGG

GGACGACAAG CCGGGCGCCG TGGGCAAGGT GGTCCCGTTC TTCGAGGCCA AGGTGGTGGA

CCTGGACACC GGCAAGACCC TGGGCGTGAA CCAGCGGGGC GAGCTGTGCG TGCGGGGGCC

GATGATCATG AGCGGCTACG TGAACAACCC GGAGGCCACC AACGCCCTCA TCGACAAGGA

CGGCTGGCTG CACAGCGGCG ACATCGCCTA CTGGGACGAG GACGAGCACT TCTTCATCGT

CGACCGGCTG AAGTCGCTGA TCAAGTACAA GGGCTACCAG GTGGCGCCGG CCGAGCTGGA

GAGCATCCTG CTCCAGCACC CCAACATCTT CGACGCCGGC GTGGCCGGGC TGCCGGACGA

CGACGCCGGC GAGCTGCCGG CCGCGGTGGT GGTGCTGGAG CACGGCAAGA CCATGACGGA

GAAGGAGATC GTCGACTACG TGGCCAGCCA GGTGACCACC GCCAAGAAGC TGCGGGGCGG

CGTGGTGTTC GTGGACGAGG TCCCGAAGGG CCTGACCGGG AAGCTCGACG CCCGGAAGAT

CCGCGAGATC CTGATCAAGG CCAAGAAGGG CGGCAAGATC GCCGTGTAAG ACTAGTACAC

ATCACAACCA CAACCTTCTC AGGCTACCCT GAGAAAAAAA GACATGAAGA CTCAGGACTC

ATCTTTTCTG TTGGTGTAAA ATCAACACCC TAAGGAACAC AAATTTCTTT AAACATTTGA

CTTCTTGTCT CTGTGCTGCA ATTAATAAAA AATGGAAAGA ATCTACAGAT CTAAAAAAAA

AAAAAAAAAA AAAAAAAAAA AAAAAAAAAA AAAAAAAAAA AAAAAAAAAA AAAAA
```

---

The invention claimed is:

1. An isolated RNA molecule comprising:
   a) at least one open reading frame (ORF);
   b) a heterologous 3'-untranslated region element (3'UTR element) comprising a nucleic acid sequence having:
      i) at least 90% identity to a mammalian albumin mRNA 3'UTR; or
      ii) at least 50 consecutive nucleotides of a mammalian albumin mRNA 3'UTR; and
   c) a histone stem-loop.

2. The RNA molecule of claim 1, wherein:
   (i) the ORF does not code for beta-globin, if the 3'UTR element is from the rat albumin 3'UTR; and
   (ii) the ORF does not code for human factor IX, if the 3'UTR element is from the human albumin 3'UTR.

3. The RNA molecule of claim 1, wherein the 3'UTR element comprises a nucleic acid sequence having at least 50, 75 or 100 consecutive nucleotides of a mammalian albumin mRNA 3'UTR.

4. The RNA molecule of claim 1, wherein the 3'UTR element comprises a nucleic acid sequence having at least 90% or 95% identity to a mammalian albumin mRNA 3'UTR.

5. The RNA molecule of claim 1, wherein the 3'UTR element comprises a nucleic acid sequence having at least 90% or 95% identity to a sequence according to SEQ ID NO: 1, SEQ ID NO: 2, SEQ ID NO: 32, SEQ ID NO: 33, SEQ ID NO: 34, or SEQ ID NO: 35.

6. The RNA molecule of claim 1, wherein the 3'UTR element comprises a human albumin mRNA 3'UTR.

7. The RNA molecule of claim 1, wherein the RNA further comprises a 5'-cap, a Poly(C) sequence, an IRES motif and/or a poly(A) sequence.

8. The RNA molecule of claim 1, wherein the ORF has an increased amount of guanine and/or cytosine residues as compared to a corresponding wild type ORF.

9. The RNA molecule of claim 7, wherein the RNA further comprises a poly(A) sequence of 20 to 300 nucleotides.

10. The RNA molecule of claim 1, wherein the at least one ORF encodes a therapeutic polypeptide or an antigen.

11. The RNA molecule of claim 10, wherein the at least one ORF encodes an antigen selected from the group consisting of an infectious disease antigen, and allergic antigen or a tumour antigen.

12. The RNA molecule of claim 1, wherein at least one guanosine, uridine, adenosine, or cytidine position of the RNA molecule is substituted with an analogue of these nucleotides selected from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, and xanthosine-5'-triphosphate.

13. A pharmaceutical composition comprising a RNA molecule of claim 1 and a pharmaceutically acceptable carrier.

14. The pharmaceutical composition of claim 13, further comprising an adjuvant.

15. The pharmaceutical composition of claim 13, wherein the composition further comprises a cationic or polycationic compound in complex with the nucleic acid molecule.

16. The isolated RNA molecule of claim 1, comprising, from 5' to 3':
   a) the at least one open reading frame (ORF);
   b) the heterologous 3'-untranslated region element (3'UTR element) comprising a nucleic acid sequence having:
      i) at least 90% identity to a mammalian albumin mRNA 3'UTR; or
      ii) at least 50 consecutive nucleotides of a mammalian albumin mRNA 3'UTR; and
   c) the histone stem-loop.

\* \* \* \* \*

SEQUENCE LISTING

<160> NUMBER OF SEQ ID NOS: 41

<210> SEQ ID NO 1
<211> LENGTH: 186
<212> TYPE: DNA
<213> ORGANISM: Artificial Sequence
<220> FEATURE:
<223> OTHER INFORMATION: fragment of 3'UTR of an albumin gene

<400> SEQUENCE: 1

```
catcacattt aaaagcatct cagcctacca tgagaataag agaaagaaaa tgaagatcaa     60
aagcttattc atctgttttt cttttcgtt ggtgtaaagc caacaccctg tctaaaaaac    120
ataaatttct ttaatcattt tgcctctttt ctctgtgctt caattaataa aaatggaaa    180 gaatct                                                              186
```

<210> SEQ ID NO 2
<211> LENGTH: 186
<212> TYPE: RNA
<213> ORGANISM: Artificial Sequence
<220> FEATURE:
<223> OTHER INFORMATION: fragment of 3'UTR of an albumin gene

<400> SEQUENCE: 2

```
caucacauuu aaaagcaucu cagccuacca ugagaauaag agaaagaaaa ugaagaucaa     60
```
aagcuuauuc aucuguuuuu cuuuuucguu gguguaaagc caacacccug ucuaaaaaac    120
auaaauuucu uuaaucauuu ugccucuuuu cucugugcuu caauuaauaa aaauggaaa    180 gaaucu                                                              186

<210> SEQ ID NO 3
<211> LENGTH: 256
<212> TYPE: DNA
<213> ORGANISM: Artificial Sequence
<220> FEATURE:
<223> OTHER INFORMATION: fragment of 3'UTR of albumin plus poly(A)

<400> SEQUENCE: 3
catcacattt aaaagcatct cagcctacca tgagaataag agaaagaaaa tgaagatcaa     60
aagcttattc atctgttttt cttttcgtt ggtgtaaagc caacaccctg tctaaaaaac    120
ataaatttct ttaatcattt tgcctctttt ctctgtgctt caattaataa aaatggaaa    180 gaatctagat ctaaaaaaaa aaaaaaaaa aaaaaaaaa aaaaaaaaa aaaaaaaaa      240 aaaaaaaaaa aaaaaa                                                   256

<210> SEQ ID NO 4
<211> LENGTH: 256
<212> TYPE: RNA
<213> ORGANISM: Artificial Sequence
<220> FEATURE:
<223> OTHER INFORMATION: fragment of 3'UTR of albumin plus poly(A)

<400> SEQUENCE: 4
caucacauuu aaaagcaucu cagccuacca ugagaauaag agaaagaaaa ugaagaucaa     60
aagcuuauuc aucuguuuuu cuuuuucguu gguguaaagc caacacccug ucuaaaaaac    120
auaaauuucu uuaaucauuu ugccucuuuu cucugugcuu caauuaauaa aaauggaaa    180 gaaucuagau cuaaaaaaaa aaaaaaaaa aaaaaaaaa aaaaaaaaa aaaaaaaaa      240 aaaaaaaaaa aaaaaa                                                   256

<210> SEQ ID NO 5
<211> LENGTH: 1746
<212> TYPE: DNA
<213> ORGANISM: Artificial Sequence
<220> FEATURE:
<223> OTHER INFORMATION: PpLuc(GC) A64

<400> SEQUENCE: 5
gggagaaagc ttgaggatgg aggacgccaa gaacatcaag aagggcccgg cgcccttcta     60
cccgctggag acgggaccg ccggcgagca gctccacaag gccatgaagc ggtacgccct    120
ggtgccgggc acgatcgcct tcaccgacgc ccacatcgag gtcgacatca cctacgcgga    180
gtacttcgag atgagcgtgc gcctggccga ggccatgaag cggtacggcc tgaacaccaa    240
ccaccggatc gtggtgtgct cggagaacag cctgcagttc ttcatgccgg tgctgggcgc    300
cctcttcatc ggcgtggccg tcgccccggc gaacgacatc tacaacgagc gggagctgct    360
gaacagcatg gggatcagcc agccgaccgt ggtgttcgtg agcaagaagg gcctgcagaa    420
gatcctgaac gtgcagaaga gctgcccat catccgaaga atcatcatca tggacagcaa    480
gaccgactac cagggcttcc agtcgatgta cacgttcgtg accagccacc tcccgccggg    540
cttcaacgag tacgacttcg tcccggagag cttcgaccgg acaagaccca tcgccctgat    600
catgaacagc agcggcagca ccggcctgcc gaaggggtg gccctgccgc accggaccgc    660

```
ctgcgtgcgc ttctcgcacg cccgggaccc catcttcggc aaccagatca tcccggacac    720
cgccatcctg agcgtggtgc cgttccacca cggcttcggc atgttcacga ccctgggcta    780
cctcatctgc ggcttccggg tggtcctgat gtaccggttc gaggaggagc tgttcctgcg    840
gagcctgcag gactacaaga tccagagcgc gctgctcgtg ccgaccctgt tcagcttctt    900
cgccaagagc accctgatcg acaagtacga cctgtcgaac ctgcacgaga tcgccagcgg    960
gggcgccccg ctgagcaagg aggtgggcga ggccgtggcc aagcggttcc acctcccggg   1020
catccgccag ggctacggcc tgaccgagac cacgagcgcg atcctgatca cccccgaggg   1080
ggacgacaag ccgggcgccg tgggcaaggt ggtcccgttc ttcgaggcca aggtggtgga   1140
cctggacacc ggcaagaccc tgggcgtgaa ccagcggggc gagctgtgcg tgcgggggcc   1200
gatgatcatg agcggctacg tgaacaaccc ggaggccacc aacgcccca tcgacaagga    1260 cggctggctg cacagcggcg acatcgccta ctgggacgag gacgagcact tcttcatcgt   1320
cgaccggctg aagtcgctga tcaagtacaa gggctaccag gtggcgccgg ccgagctgga   1380
gagcatcctg ctccagcacc ccaacatctt cgacgccggc gtggccgggc tgccggacga   1440
cgacgccggc gagctgccgg ccgcggtggt ggtgctggag cacggcaaga ccatgacgga   1500
gaaggagatc gtcgactacg tggccagcca ggtgaccacc gccaagaagc tgcggggcgg   1560
cgtggtgttc gtggacgagg tcccgaaggg cctgaccggg aagctcgacg cccggaagat   1620
ccgcgagatc ctgatcaagg ccaagaaggg cggcaagatc gccgtgtaag actagtagat   1680
ctaaaaaaaa aaaaaaaaaa aaaaaaaaaa aaaaaaaaaa aaaaaaaaaa aaaaaaaaaa   1740
aaaaaa                                                              1746

<210> SEQ ID NO 6
<211> LENGTH: 1933
<212> TYPE: DNA
<213> ORGANISM: Artificial Sequence
<220> FEATURE:
<223> OTHER INFORMATION: PpLuc(GC) albumin A64

<400> SEQUENCE: 6
gggagaaagc ttgaggatgg aggacgccaa gaacatcaag aagggcccgg cgcccttcta     60
cccgctggag gacgggaccg ccggcgagca gctccacaag gccatgaagc ggtacgccct    120
ggtgccgggc acgatcgcct tcaccgacgc ccacatcgag gtcgacatca cctacgcgga    180
gtacttcgag atgagcgtgc gcctggccga ggccatgaag cggtacggcc tgaacaccaa    240
ccaccggatc gtggtgtgct cggagaacag cctgcagttc ttcatgccgg tgctgggcgc    300
cctcttcatc ggcgtggccg tcgccccggc gaacgacatc tacaacgagc gggagctgct    360
gaacagcatg gggatcagcc agccgaccgt ggtgttcgtg agcaagaagg gcctgcagaa    420
gatcctgaac gtgcagaaga agctgcccat catccagaag atcatcatca tggacagcaa    480
gaccgactac cagggcttcc agtcgatgta cacgttcgtg accagccacc tcccgccggg    540
cttcaacgag tacgacttcg tcccggagag cttcgaccgg acaagacca tcgccctgat     600 catgaacagc agcggcagca ccggcctgcc gaaggggtg ccctgccgc accggaccgc     660 ctgcgtgcgc ttctcgcacg cccgggaccc catcttcggc aaccagatca tcccggacac    720
cgccatcctg agcgtggtgc cgttccacca cggcttcggc atgttcacga ccctgggcta    780
cctcatctgc ggcttccggg tggtcctgat gtaccggttc gaggaggagc tgttcctgcg    840
gagcctgcag gactacaaga tccagagcgc gctgctcgtg ccgaccctgt tcagcttctt    900
cgccaagagc accctgatcg acaagtacga cctgtcgaac ctgcacgaga tcgccagcgg    960
```

```
gggcgccccg ctgagcaagg aggtgggcga ggccgtggcc aagcggttcc acctcccggg   1020
catccgccag ggctacggcc tgaccgagac cacgagcgcg atcctgatca cccccgaggg   1080
ggacgacaag ccgggcgccg tgggcaaggt ggtcccgttc ttcgaggcca aggtggtgga   1140
cctggacacc ggcaagaccc tgggcgtgaa ccagcggggc gagctgtgcg tgcggggggcc   1200 gatgatcatg agcggctacg tgaacaaccc ggaggccacc aacgccctca tcgacaagga   1260
cggctggctg cacagcggcg acatcgccta ctgggacgag gacgagcact tcttcatcgt   1320
cgaccggctg aagtcgctga tcaagtacaa gggctaccag gtggcgccgg ccgagctgga   1380
gagcatcctg ctccagcacc ccaacatctt cgacgccggc gtggccgggc tgccggacga   1440
cgacgccggc gagctgccgg ccgcggtggt ggtgctggag cacggcaaga ccatgacgga   1500
gaaggagatc gtcgactacg tggccagcca ggtgaccacc gccaagaagc tgcggggcgg   1560
cgtggtgttc gtggacgagg tcccgaaggg cctgaccggg aagctcgacg cccggaagat   1620
ccgcgagatc ctgatcaagg ccaagaaggg cggcaagatc gccgtgtaag actagtgcat   1680
cacatttaaa agcatctcag cctaccatga gaataagaga agaaaatga agatcaaaag   1740 cttattcatc tgttttctt tttcgttggt gtaaagccaa caccctgtct aaaaaacata   1800
aatttcttta atcattttgc ctcttttctc tgtgcttcaa ttaataaaaa atggaaagaa   1860
tctagatcta aaaaaaaaa aaaaaaaaaa aaaaaaaaa aaaaaaaaa aaaaaaaaaa   1920 aaaaaaaaa aaa                                                    1933

<210> SEQ ID NO 7
<211> LENGTH: 1933
<212> TYPE: DNA
<213> ORGANISM: Artificial Sequence
<220> FEATURE:
<223> OTHER INFORMATION: PpLuc(GC) albumin2 A64

<400> SEQUENCE: 7
gggagaaagc ttgaggatgg aggacgccaa gaacatcaag aagggcccgg cgcccttcta   60
cccgctggag gacgggaccg ccggcgagca gctccacaag gccatgaagc ggtacgccct   120
ggtgccgggc acgatcgcct tcaccgacgc ccacatcgag gtcgacatca cctacgcgga   180
gtacttcgag atgagcgtgc gcctggccga ggccatgaag cggtacggcc tgaacaccaa   240
ccaccggatc gtggtgtgct cggagaacag cctgcagttc ttcatgccgg tgctgggcgc   300
cctcttcatc ggcgtggccg tcgccccggc gaacgacatc tacaacgagc gggagctgct   360
gaacagcatg gggatcagcc agccgaccgt ggtgttcgtg agcaagaagg gcctgcagaa   420
gatcctgaac gtgcagaaga agctgcccat catccagaag atcatcatca tggacagcaa   480
gaccgactac cagggcttcc agtcgatgta cacgttcgtg accagccacc tcccgccggg   540
cttcaacgag tacgacttcg tcccggagag cttcgaccgg gacaagacca tcgccctgat   600
catgaacagc agcggcagca ccggcctgcc gaaggggtg gccctgccgc accgaccgc   660 ctgcgtgcgc ttctcgcacg cccgggaccc catcttcggc aaccagatca tcccggacac   720
cgccatcctg agcgtggtgc cgttccacca cggcttcggc atgttcacga ccctgggcta   780
cctcatctgc ggcttccggg tggtcctgat gtaccggttc gaggaggagc tgttcctgcg   840
gagcctgcag gactacaaga tccagagcgc gctgctcgtg ccgaccctgt tcagcttctt   900
cgccaagagc accctgatcg acaagtacga cctgtcgaac ctgcacgaga tcgccagcgg   960
gggcgccccg ctgagcaagg aggtgggcga ggccgtggcc aagcggttcc acctcccggg   1020
```

| | |
|---|---:|
| catccgccag ggctacggcc tgaccgagac cacgagcgcg atcctgatca ccccgaggg | 1080 |
| ggacgacaag ccgggcgccg tgggcaaggt ggtcccgttc ttcgaggcca aggtggtgga | 1140 |
| cctggacacc ggcaagaccc tgggcgtgaa ccagcggggc gagctgtgcg tgcgggggcc | 1200 |
| gatgatcatg agcggctacg tgaacaaccc ggaggccacc aacgccctca tcgacaagga | 1260 |
| cggctggctg cacagcggcg acatcgccta ctgggacgag gacgagcact tcttcatcgt | 1320 |
| cgaccggctg aagtcgctga tcaagtacaa gggctaccag gtggcgccgg ccagctgga | 1380 |
| gagcatcctg ctccagcacc ccaacatctt cgacgccggc gtggccgggc tgccggacga | 1440 |
| cgacgccggc gagctgccgg ccgcggtggt ggtgctggag cacggcaaga ccatgacgga | 1500 |
| gaaggagatc gtcgactacg tggccagcca ggtgaccacc gccaagaagc tgcggggcgg | 1560 |
| cgtggtgttc gtggacgagg tcccgaaggg cctgaccggg aagctcgacg cccggaagat | 1620 |
| ccgcgagatc ctgatcaagg ccaagaaggg cggcaagatc gccgtgtaag actagtgcat | 1680 |
| cacatttaaa agcatctcag cctaccatga gaataagaga agaaaatga agatcaaaag | 1740 |
| cttattcgtc tgttttctt tttcgttggt gtaaagccaa caccctgtct aaaaaacata | 1800 |
| aatttcttta atcattttgc ctctttctc tgtgcttcaa ttaataaaaa atggaaagaa | 1860 |
| tctagatcta aaaaaaaaaa aaaaaaaaaa aaaaaaaaaa aaaaaaaaaa aaaaaaaaaa | 1920 |
| aaaaaaaaaa aaa | 1933 |

<210> SEQ ID NO 8
<211> LENGTH: 1933
<212> TYPE: DNA
<213> ORGANISM: Artificial Sequence
<220> FEATURE:
<223> OTHER INFORMATION: PpLuc(GC) albumin3 A64

<400> SEQUENCE: 8

| | |
|---|---:|
| gggagaaagc ttgaggatgg aggacgccaa gaacatcaag aagggcccgg cgcccttcta | 60 |
| cccgctggag gacgggaccg ccggcgagca gctccacaag gccatgaagc ggtacgccct | 120 |
| ggtgccgggc acgatcgcct tcaccgacgc ccacatcgag gtcgacatca cctacgcgga | 180 |
| gtacttcgag atgagcgtgc gcctggccga ggccatgaag cggtacgcc tgaacaccaa | 240 |
| ccaccggatc gtggtgtgct cggagaacag cctgcagttc ttcatgccgg tgctgggcgc | 300 |
| cctcttcatc ggcgtggccg tcgccccggc gaacgacatc tacaacgagc gggagctgct | 360 |
| gaacagcatg gggatcagcc agccgaccgt ggtgttcgtg agcaagaagg gcctgcagaa | 420 |
| gatcctgaac gtgcagaaga gctgcccat catccgaaag atcatcatca tggacagcaa | 480 |
| gaccgactac cagggcttcc agtcgatgta cacgttcgtg accagccacc tcccgccggg | 540 |
| cttcaacgag tacgacttcg tcccggagag cttcgaccgg acaagacca tcgccctgat | 600 |
| catgaacagc agcggcagca ccggcctgcc gaaggggtg gccctgccgc accggaccgc | 660 |
| ctgcgtgcgc ttctcgcacg ccgggacc catcttcggc aaccagatca tcccggacac | 720 |
| cgccatcctg agcgtggtgc cgttccacca cggcttcggc atgttcacga ccctgggcta | 780 |
| cctcatctgc ggcttccggg tggtcctgat gtaccggttc gaggaggagc tgttcctgcg | 840 |
| gagcctgcag gactacaaga tccagagcgc gctgctcgtg ccgaccctgt tcagcttctt | 900 |
| cgccaagagc accctgatcg acaagtacga cctgtcgaac ctgcacgaga tcgccagcgg | 960 |
| gggcgccccg ctgagcaagg aggtgggcga ggccgtggcc aagcggttcc acctcccggg | 1020 |
| catccgccag ggctacggcc tgaccgagac cacgagcgcg atcctgatca ccccgaggg | 1080 |
| ggacgacaag ccgggcgccg tgggcaaggt ggtcccgttc ttcgaggcca aggtggtgga | 1140 |

```
cctggacacc ggcaagaccc tgggcgtgaa ccagcggggc gagctgtgcg tgcgggggcc    1200
gatgatcatg agcggctacg tgaacaaccc ggaggccacc aacgccctca tcgacaagga    1260
cggctggctg cacagcggcg acatcgccta ctgggacgag gacgagcact tcttcatcgt    1320
cgaccggctg aagtcgctga tcaagtacaa gggctaccag gtggcgccgg ccgagctgga    1380
gagcatcctg ctccagcacc ccaacatctt cgacgccggc gtggccgggc tgccggacga    1440
cgacgccggc gagctgccgg ccgcggtggt ggtgctggag cacggcaaga ccatgacgga    1500
gaaggagatc gtcgactacg tggccagcca ggtgaccacc gccaagaagc tgcggggcgg    1560
cgtggtgttc gtggacgagg tcccgaaggg cctgaccggg aagctcgacg cccggaagat    1620
ccgcgagatc ctgatcaagg ccaagaaggg cggcaagatc gccgtgtaag actagtgcat    1680
cacatttaaa agcatctcag cctaccatga gaataagaga agaaaatga agatcaaaag    1740 cttattcatc agttttttctt tttcgttggt gtaaagccaa caccctgtct aaaaaacata    1800
aatttcttta atcattttgc ctcttttctc tgtgcttcaa ttaataaaaa atggaaagaa    1860
tctagatcta aaaaaaaaa aaaaaaaaa aaaaaaaaa aaaaaaaaa aaaaaaaaa    1920 aaaaaaaaaa aaa    1933
```

<210> SEQ ID NO 9
<211> LENGTH: 1933
<212> TYPE: DNA
<213> ORGANISM: Artificial Sequence
<220> FEATURE:
<223> OTHER INFORMATION: PpLuc(GC) albumin4 A64

<400> SEQUENCE: 9

```
gggagaaagc ttgaggatgg aggacgccaa gaacatcaag aagggcccgg cgcccttcta     60
cccgctggag gacgggaccg ccggcgagca gctccacaag gccatgaagc ggtacgccct    120
ggtgccgggc acgatcgcct tcaccgacgc ccacatcgag gtcgacatca cctacgcgga    180
gtacttcgag atgagcgtgc gcctggccga ggccatgaag cggtacggcc tgaacaccaa    240
ccaccggatc gtggtgtgct cggagaacag cctgcagttc ttcatgccgg tgctgggcgc    300
cctcttcatc ggcgtggccg tcgccccggc gaacgacatc tacaacgagc gggagctgct    360
gaacagcatg gggatcagcc agccgaccgt ggtgttcgtg agcaagaagg gcctgcagaa    420
gatcctgaac gtgcagaaga agctgccgat catccagaag atcatcatca tggacagcaa    480
gaccgactac cagggcttcc agtcgatgta cacgttcgtg accagccacc tcccgccggg    540
cttcaacgag tacgacttcg tcccggagag cttcgaccgg acaagacca tcgccctgat    600 catgaacagc agcggcagca ccggcctgcc gaaggggtg ccctgccgc accggaccgc    660 ctgcgtgcgc ttctcgcacg cccgggaccc catcttcggc aaccagatca tcccggacac    720
cgccatcctg agcgtggtgc cgttccacca cggcttcggc atgttcacga ccctgggcta    780
cctcatctgc ggcttccggg tggtcctgat gtaccggttc gaggaggagc tgttcctgcg    840
gagcctgcag gactacaaga tccagagcgc gctgctcgtg ccgaccctgt tcagcttctt    900
cgccaagagc acccctgatcg acaagtacga cctgtcgaac ctgcacgaga tcgccagcgg    960
gggcgccccg ctgagcaagg aggtgggcga ggccgtggcc aagcggttcc acctcccggg    1020
catccgccag ggctacggcc tgaccgagac cacgagcgcg atcctgatca ccccccgaggg    1080 ggacgacaag ccgggcgccg tgggcaaggt ggtcccgttc ttcgaggcca aggtggtgga    1140
cctggacacc ggcaagaccc tgggcgtgaa ccagcggggc gagctgtgcg tgcgggggcc    1200
```

```
gatgatcatg agcggctacg tgaacaaccc ggaggccacc aacgccctca tcgacaagga    1260
cggctggctg cacagcggcg acatcgccta ctgggacgag gacgagcact tcttcatcgt    1320
cgaccggctg aagtcgctga tcaagtacaa gggctaccag gtggcgccgg ccgagctgga    1380
gagcatcctg ctccagcacc ccaacatctt cgacgccggc gtggccgggc tgccggacga    1440
cgacgccggc gagctgccgg ccgcggtggt ggtgctggag cacggcaaga ccatgacgga    1500
gaaggagatc gtcgactacg tggccagcca ggtgaccacc gccaagaagc tgcggggcgg    1560
cgtggtgttc gtggacgagg tcccgaaggg cctgaccggg aagctcgacg cccggaagat    1620
ccgcgagatc ctgatcaagg ccaagaaggg cggcaagatc gccgtgtaag actagtgcat    1680
cacatttaaa agcatctcag cctaccatga gaataagaga aagaaaatga agatcaaaag    1740
cttattcatc tctttttctt tttcgttggt gtaaagccaa caccctgtct aaaaaacata    1800
aatttcttta atcattttgc ctcttttctc tgtgcttcaa ttaataaaaa atggaaagaa    1860
tctagatcta aaaaaaaaaa aaaaaaaaaa aaaaaaaaaa aaaaaaaaaa aaaaaaaaaa    1920
aaaaaaaaaa aaa                                                       1933

<210> SEQ ID NO 10
<211> LENGTH: 1933
<212> TYPE: DNA
<213> ORGANISM: Artificial Sequence
<220> FEATURE:
<223> OTHER INFORMATION: PpLuc(GC) albumin5 A64

<400> SEQUENCE: 10
gggagaaagc ttgaggatgg aggacgccaa gaacatcaag aagggcccgg cgcccttcta     60
cccgctggag gacgggaccg ccggcgagca gctccacaag gccatgaagc ggtacgccct    120
ggtgccgggc acgatcgcct tcaccgacgc ccacatcgag gtcgacatca cctacgcgga    180
gtacttcgag atgagcgtgc gcctggccga ggccatgaag cggtacggcc tgaacaccaa    240
ccaccggatc gtggtgtgct cggagaacag cctgcagttc ttcatgccgg tgctgggcgc    300
cctcttcatc ggcgtggccg tcgccccggc gaacgacatc tacaacgagc gggagctgct    360
gaacagcatg gggatcagcc agccgaccgt ggtgttcgtg agcaagaagg gcctgcagaa    420
gatcctgaac gtgcagaaga agctgcccat catccagaag atcatcatca tggacagcaa    480
gaccgactac cagggcttcc agtcgatgta cacgttcgtg accagccacc tcccgccggg    540
cttcaacgag tacgacttcg tcccggagag cttcgaccgg acaagacca tcgccctgat    600 catgaacagc agcggcagca ccggcctgcc gaaggggtg gccctgccgc accgaccgc     660 ctgcgtgcgc ttctcgcacg cccgggaccc catcttcggc aaccagatca tcccggacac    720
cgccatcctg agcgtggtgc cgttccacca cggcttcggc atgttcacga ccctgggcta    780
cctcatctgc ggcttccggg tggtcctgat gtaccggttc gaggaggagc tgttcctgcg    840
gagcctgcag gactacaaga tccagagcgc gctgctcgtg ccgacccgt tcagcttctt     900 cgccaagagc accctgatcg acaagtacga cctgtcgaac ctgcacgaga tcgccagcgg    960 gggcgcccc ctgagcaagg aggtgggcga ggccgtggcc aagcggttcc acctccgggg   1020
catccgccag ggctacggcc tgaccgagac cacgagcgcg atcctgatca cccccgaggg   1080
ggacgacaag ccgggcgccg tgggcaaggt ggtcccgttc ttcgaggcca aggtggtgga   1140
cctggacacc ggcaagaccc tgggcgtgaa ccagcggggc gagctgtgcg tgcgggggcc   1200
gatgatcatg agcggctacg tgaacaaccc ggaggccacc aacgccctca tcgacaagga   1260
cggctggctg cacagcggcg acatcgccta ctgggacgag gacgagcact tcttcatcgt   1320
```

```
cgaccggctg aagtcgctga tcaagtacaa gggctaccag gtggcgccgg ccgagctgga    1380
gagcatcctg ctccagcacc ccaacatctt cgacgccggc gtggccgggc tgccggacga    1440
cgacgccggc gagctgccgg ccgcggtggt ggtgctggag cacggcaaga ccatgacgga    1500
gaaggagatc gtcgactacg tggccagcca ggtgaccacc gccaagaagc tgcggggcgg    1560
cgtggtgttc gtggacgagg tcccgaaggg cctgaccggg aagctcgacg cccggaagat    1620
ccgcgagatc ctgatcaagg ccaagaaggg cggcaagatc gccgtgtaag actagtgcat    1680
cacatttaaa agcatctcag cctaccatga gaataagaga agaaaatgaa gatcaaaag    1740 cttattcatc tgttggtctt tttcgttggt gtaaagccaa caccctgtct aaaaaacata    1800
aatttcttta atcattttgc ctctttctc tgtgcttcaa ttaataaaaa atggaaagaa    1860
tctagatcta aaaaaaaaaa aaaaaaaaaa aaaaaaaaaa aaaaaaaaaa aaaaaaaaaa    1920
aaaaaaaaaa aaa                                                      1933
```

<210> SEQ ID NO 11
<211> LENGTH: 1933
<212> TYPE: DNA
<213> ORGANISM: Artificial Sequence
<220> FEATURE:
<223> OTHER INFORMATION: PpLuc(GC) albumin6 A64

<400> SEQUENCE: 11

```
gggagaaagc ttgaggatgg aggacgccaa gaacatcaag aagggcccgg cgcccttcta     60
cccgctggag gacgggaccg ccggcgagca gctccacaag gccatgaagc ggtacgccct    120
ggtgccgggc acgatcgcct tcaccgacgc ccacatcgag gtcgacatca cctacgcgga    180
gtacttcgag atgagcgtgc gcctggccga ggccatgaag cggtacgcc tgaacaccaa    240 ccaccggatc gtggtgtgct cggagaacag cctgcagttc ttcatgccgg tgctgggcgc    300
cctcttcatc ggcgtggccg tcgccccggc gaacgacatc tacaacgagc gggagctgct    360
gaacagcatg gggatcagcc agccgaccgt ggtgttcgtg agcaagaagg gcctgcagaa    420
gatcctgaac gtgcagaaga gctgcccat catccgaaag atcatcatca tggacagcaa    480
gaccgactac cagggcttcc agtcgatgta cacgttcgtg accagccacc tcccgccggg    540
cttcaacgag tacgacttcg tcccggagag cttcgaccgg gacaagacca tcgccctgat    600
catgaacagc agcggcagca ccggcctgcc gaagggggtg gccctgccgc accgaccgc    660 ctgcgtgcgc ttctcgcacg cccgggaccc catcttcggc aaccagatca tcccggacac    720
cgccatcctg agcgtggtgc cgttccacca cggcttcggc atgttcacga ccctgggcta    780
cctcatctgc ggcttccggg tggtcctgat gtaccggttc gaggaggagc tgttcctgcg    840
gagcctgcag gactacaaga tccagagcgc gctgctcgtg ccgaccctgt tcagcttctt    900
cgccaagagc accctgatcg acaagtacga cctgtcgaac ctgcacgaga tcgccagcgg    960
gggcgccccg ctgagcaagg aggtgggcga ggccgtggcc aagcggttcc acctcccggg    1020
catccgccag ggctacggcc tgaccgagac cacgagcgcg atcctgatca cccccgaggg    1080
ggacgacaag ccgggcgccg tgggcaaggt ggtcccgttc ttcgaggcca aggtggtgga    1140
cctggacacc ggcaagaccc tgggcgtgaa ccagcggggc gagctgtgcg tgcggggcc    1200 gatgatcatg agcggctacg tgaacaaccc ggaggccacc aacgccctca tcgacaagga    1260
cggctggctg cacagcggcg acatcgccta ctgggacgag gacgagcact tcttcatcgt    1320
cgaccggctg aagtcgctga tcaagtacaa gggctaccag gtggcgccgg ccgagctgga    1380
```

```
gagcatcctg ctccagcacc ccaacatctt cgacgccggc gtggccgggc tgccggacga   1440
cgacgccggc gagctgccgg ccgcggtggt ggtgctggag cacggcaaga ccatgacgga   1500
gaaggagatc gtcgactacg tggccagcca ggtgaccacc gccaagaagc tgcggggcgg   1560
cgtggtgttc gtggacgagg tcccgaaggg cctgaccggg aagctcgacg cccggaagat   1620
ccgcgagatc ctgatcaagg ccaagaaggg cggcaagatc gccgtgtaag actagtgcat   1680
cacatttaaa agcatctcag cctaccatga gaataagaga agaaaatga agatcaatag   1740 cttattcatc tgttttcttt tttcgttggt gtaaagccaa caccctgtct aaaaaacata   1800
aatttcttta atcattttgc ctcttttctc tgtgcttcaa ttaataaaaa atggaaagaa   1860
cctagatcta aaaaaaaaaa aaaaaaaaaa aaaaaaaaaa aaaaaaaaaa aaaaaaaaaa   1920
aaaaaaaaaa aaa                                                      1933

<210> SEQ ID NO 12
<211> LENGTH: 1933
<212> TYPE: DNA
<213> ORGANISM: Artificial Sequence
<220> FEATURE:
<223> OTHER INFORMATION: PpLuc(GC)  albumin7 A64

<400> SEQUENCE: 12
gggagaaagc ttgaggatgg aggacgccaa gaacatcaag aagggcccgg cgcccttcta     60
cccgctggag gacgggaccg ccggcgagca gctccacaag gccatgaagc ggtacgccct    120
ggtgccgggc acgatcgcct tcaccgacgc ccacatcgag gtcgacatca cctacgcgga    180
gtacttcgag atgagcgtgc gcctggccga ggccatgaag cggtacgccc tgaacaccaa    240
ccaccggatc gtggtgtgct cggagaacag cctgcagttc ttcatgccgg tgctgggcgc    300
cctcttcatc ggcgtggccg tcgccccggc gaacgacatc tacaacgagc gggagctgct    360
gaacagcatg gggatcagcc agccgaccgt ggtgttcgtg agcaagaagg gcctgcagaa    420
gatcctgaac gtgcagaaga agctgccgat catccgaaag atcatcatca tggacagcaa    480
gaccgactac cagggcttcc agtcgatgta cacgttcgtg accagccacc tcccgccggg    540
cttcaacgag tacgacttcg tcccggagag cttcgaccgg acaagacca tcgccctgat    600 catgaacagc agcggcagca ccggcctgcc gaaggggtg gccctgccgc accggaccgc    660
ctgcgtgcgc ttctcgcacg cccgggaccc catcttcggc aaccagatca tcccggacac    720
cgccatcctg agcgtggtgc cgttccacca cggcttcggc atgttcacga ccctgggcta    780
cctcatctgc ggcttccggg tggtcctgat gtaccggttc gaggaggagc tgttcctgcg    840
gagcctgcag gactacaaga tccagagcgc gctgctcgtg ccgaccctgt tcagcttctt    900
cgccaagagc accctgatcg acaagtacga cctgtcgaac ctgcacgaga tcgccagcgg    960
gggcgccccg ctgagcaagg aggtgggcga ggccgtggcc aagcggttcc acctcccggg   1020
catccgccag ggctacggcc tgaccgagac cacgagcgcg atcctgatca cccccgaggg   1080
ggacgacaag ccgggcgccg tgggcaaggt ggtcccgttc ttcgaggcca aggtggtgga   1140
cctggacacc ggcaagaccc tgggcgtgaa ccagcggggc gagctgtgcg tgcgggggcc   1200
gatgatcatg agcggctacg tgaacaaccc ggaggccacc aacgccctca tcgacaagga   1260
cggctggctg cacagcggcg acatcgccta ctgggacgag gacgagcact tcttcatcgt   1320
cgaccggctg aagtcgctga tcaagtacaa gggctaccag gtggcgccgg ccgagctgga   1380
gagcatcctg ctccagcacc ccaacatctt cgacgccggc gtggccgggc tgccggacga   1440
cgacgccggc gagctgccgg ccgcggtggt ggtgctggag cacggcaaga ccatgacgga   1500
```

```
gaaggagatc gtcgactacg tggccagcca ggtgaccacc gccaagaagc tgcggggcgg    1560
cgtggtgttc gtggacgagg tcccgaaggg cctgaccggg aagctcgacg cccggaagat    1620
ccgcgagatc ctgatcaagg ccaagaaggg cggcaagatc gccgtgtaag actagtgcat    1680
cacatttaaa agcatctcag cctaccatga gaataagaga agaaaatga agatcaatag    1740 cttattcatc tcttttcctt tttcgttggt gtaaagccaa cacctgtct aaaaaacata    1800 aatttctttg atcattttgc ctcttttctc tgtgcttcaa ttaataaaaa atggaaagaa    1860
cctagatcta aaaaaaaaa aaaaaaaaa aaaaaaaaa aaaaaaaaa aaaaaaaaa       1920 aaaaaaaaaa aaa                                                      1933

<210> SEQ ID NO 13
<211> LENGTH: 1812
<212> TYPE: DNA
<213> ORGANISM: Artificial Sequence
<220> FEATURE:
<223> OTHER INFORMATION: PpLuc(GC) ag A64

<400> SEQUENCE: 13
gggagaaagc ttgaggatgg aggacgccaa gaacatcaag aagggcccgg cgcccttcta     60
cccgctggag gacgggaccg ccggcgagca gctccacaag gccatgaagc ggtacgccct    120
ggtgccgggc acgatcgcct tcaccgacgc ccacatcgag gtcgacatca cctacgcgga    180
gtacttcgag atgagcgtgc gcctggccga ggccatgaag cggtacggcc tgaacaccaa    240
ccaccggatc gtggtgtgct cggagaacag cctgcagttc ttcatgccgg tgctgggcgc    300
cctcttcatc ggcgtggccg tcgccccggc gaacgacatc tacaacgagc gggagctgct    360
gaacagcatg gggatcagcc agccgaccgt ggtgttcgtg agcaagaagg gcctgcagaa    420
gatcctgaac gtgcagaaga gctgcccat catccgaaag atcatcatca tggacagcaa    480
gaccgactac cagggcttcc agtcgatgta cacgttcgtg accagccacc tcccgccggg    540
cttcaacgag tacgacttcg tcccggagag cttcgaccgg gacaagacca tcgccctgat    600
catgaacagc agcggcagca ccggcctgcc gaaggggtg ccctgccgc accggaccgc    660 ctgcgtgcgc ttctcgcacg cccgggaccc catcttcggc aaccagatca tcccggacac    720
cgccatcctg agcgtggtgc cgttccacca cggcttcggc atgttcacga ccctgggcta    780
cctcatctgc ggcttccggg tggtcctgat gtaccggttc gaggaggagc tgttcctgcg    840
gagcctgcag gactacaaga tccagagcgc gctgctcgtg ccgaccctgt tcagcttctt    900
cgccaagagc accctgatcg acaagtacga cctgtcgaac ctgcacgaga tcgccagcgg    960
gggcgccccg ctgagcaagg aggtgggcga ggccgtggcc aagcggttcc acctcccggg   1020
catccgccag ggctacggcc tgaccgagac cacgagcgcg atcctgatca ccccggaggg   1080
ggacgacaag ccgggcgccg tgggcaaggt ggtcccgttc ttcgaggcca aggtggtgga   1140
cctggacacc ggcaagaccc tgggcgtgaa ccagcggggc gagctgtgcg tgcggggcc    1200 gatgatcatg agcggctacg tgaacaaccc ggaggccacc aacgccctca tcgacaagga   1260
cggctggctg cacagcggcg acatcgccta ctgggacgag gacgagcact tcttcatcgt   1320
cgaccggctg aagtcgctga tcaagtacaa gggctaccag gtggcgccgg ccgagctgga   1380
gagcatcctg ctccagcacc ccaacatctt cgacgccggc gtggccgggc tgccggacga   1440
cgacgccggc gagctgccgg ccgcggtggt ggtgctggag cacggcaaga ccatgacgga   1500
gaaggagatc gtcgactacg tggccagcca ggtgaccacc gccaagaagc tgcggggcgg   1560
```

```
cgtggtgttc gtggacgagg tcccgaaggg cctgaccggg aagctcgacg cccggaagat      1620
ccgcgagatc ctgatcaagg ccaagaaggg cggcaagatc gccgtgtaag actagttata      1680
agactgacta gcccgatggg cctcccaacg ggccctcctc ccctccttgc accgagatta      1740
atagatctaa aaaaaaaaaa aaaaaaaaaa aaaaaaaaaa aaaaaaaaaa aaaaaaaaaa      1800
aaaaaaaaaa aa                                                          1812

<210> SEQ ID NO 14
<211> LENGTH: 1955
<212> TYPE: DNA
<213> ORGANISM: Artificial Sequence
<220> FEATURE:
<223> OTHER INFORMATION: PpLuc(GC) gusb A64

<400> SEQUENCE: 14
gggagaaagc ttgaggatgg aggacgccaa gaacatcaag aagggcccgg cgcccttcta        60
cccgctggag gacgggaccg ccggcgagca gctccacaag gccatgaagc ggtacgccct       120
ggtgccgggc acgatcgcct tcaccgacgc ccacatcgag gtcgacatca cctacgcgga       180
gtacttcgag atgagcgtgc gcctggccga ggccatgaag cggtacggcc tgaacaccaa       240
ccaccggatc gtggtgtgct cggagaacag cctgcagttc ttcatgccgg tgctgggcgc       300
cctcttcatc ggcgtggccg tcgccccggc gaacgacatc tacaacgagc gggagctgct       360
gaacagcatg gggatcagcc agccgaccgt ggtgttcgtg agcaagaagg gcctgcagaa       420
gatcctgaac gtgcagaaga agctgcccat catccagaag atcatcatca tggacagcaa       480
gaccgactac cagggcttcc agtcgatgta cacgttcgtg accagccacc tcccgccggg       540
cttcaacgag tacgacttcg tcccggagag cttcgaccgg acaagaccca tcgccctgat       600
catgaacagc agcggcagca ccggcctgcc gaaggggtg gccctgccgc accgaccgc         660 ctgcgtgcgc ttctcgcacg cccgggaccc catcttcggc aaccagatca tcccggacac       720
cgccatcctg agcgtggtgc cgttccacca cggcttcggc atgttcacga ccctgggcta       780
cctcatctgc ggcttccggg tggtcctgat gtaccggttc gaggaggagc tgttcctgcg       840
gagcctgcag gactacaaga tccagagcgc gctgctcgtg ccgaccctgt tcagcttctt       900
cgccaagagc accctgatcg acaagtacga cctgtcgaac ctgcacgaga tcgccagcgg       960
gggcgccccg ctgagcaagg aggtgggcga ggccgtggcc aagcggttcc acctcccggg      1020
catccgccag ggctacggcc tgaccgagac cacgagcgcg atcctgatca cccccgaggg      1080
ggacgacaag ccgggcgccg tgggcaaggt ggtcccgttc ttcgaggcca aggtggtgga      1140
cctggacacc ggcaagaccc tgggcgtgaa ccagcggggc gagctgtgcg tgcgggggcc      1200
gatgatcatg agcggctacg tgaacaaccc ggaggccacc aacgccctca tcgacaagga      1260
cggctggctg cacagcggcg acatcgccta ctgggacgag gacgagcact tcttcatcgt      1320
cgaccggctg aagtcgctga tcaagtacaa gggctaccag gtggcgccgg ccgagctgga      1380
gagcatcctg ctccagcacc ccaacatctt cgacgccggc gtggccgggc tgccggacga      1440
cgacgccggc gagctgccgg ccgcggtggt ggtgctggag cacggcaaga ccatgacgga      1500
gaaggagatc gtcgactacg tggccagcca ggtgaccacc gccaagaagc tgcggggcgg      1560
cgtggtgttc gtggacgagg tcccgaaggg cctgaccggg aagctcgacg cccggaagat      1620
ccgcgagatc ctgatcaagg ccaagaaggg cggcaagatc gccgtgtaag actagtgcaa      1680
gactgatacc acctgcgtgt cccttcctcc ccgagtcagg gcgacttcca cagcagcaga      1740
acaagtgcct cctggactgt tcacggcaga ccagaacgtt tctggcctgg gttttgtggt      1800
```

```
catctattct agcagggaac actaaaggtg gaaataaaag attttctatt atgggaaataa    1860
agagttggca tgaaagtggc tactgagatc taaaaaaaaa aaaaaaaaaa aaaaaaaaaa    1920
aaaaaaaaaa aaaaaaaaaa aaaaaaaaaa aaaaa                               1955
```

<210> SEQ ID NO 15
<211> LENGTH: 1818
<212> TYPE: DNA
<213> ORGANISM: Artificial Sequence
<220> FEATURE:
<223> OTHER INFORMATION: PpLuc(GC) atp5o A64

<400> SEQUENCE: 15

```
gggagaaagc ttgaggatgg aggacgccaa gaacatcaag aagggcccgg cgcccttcta      60
cccgctggag gacgggaccg ccggcgagca gctccacaag gccatgaagc ggtacgccct     120
ggtgccgggc acgatcgcct tcaccgacgc ccacatcgag gtcgacatca cctacgcgga     180
gtacttcgag atgagcgtgc gcctggccga ggccatgaag cggtacgccc tgaacaccaa     240
ccaccggatc gtggtgtgct cggagaacag cctgcagttc ttcatgccgg tgctgggcgc     300
cctcttcatc ggcgtggccg tcgccccggc gaacgacatc tacaacgagc gggagctgct     360
gaacagcatg gggatcagcc agccgaccgt ggtgttcgtg agcaagaagg gcctgcagaa     420
gatcctgaac gtgcagaaga gctgcccat catccgaaag atcatcatca tggacagcaa     480
gaccgactac cagggcttcc agtcgatgta cacgttcgtg accagccacc tcccgccggg     540
cttcaacgag tacgacttcg tcccggagag cttcgaccgg acaagaccc tcgccctgat     600
catgaacagc agcggcagca ccggcctgcc gaaggggtg gccctgccgc accggaccgc     660
ctgcgtgcgc ttctcgcacg cccgggaccc catcttcggc aaccagatca tcccggacac     720
cgccatcctg agcgtggtgc cgttccacca cggcttcggc atgttcacga ccctgggcta     780
cctcatctgc ggcttccggg tggtcctgat gtaccggttc gaggaggagc tgttcctgcg     840
gagcctgcag gactacaaga tccagagcgc gctgctcgtg ccgaccctgt tcagcttctt     900
cgccaagagc accctgatcg acaagtacga cctgtcgaac ctgcacgaga tcgccagcgg     960
gggcgccccg ctgagcaagg aggtgggcga ggccgtggcc aagcggttcc acctcccggg    1020
catccgccag ggctacgcc tgaccgagac cacgagcgcg atcctgatca ccccccgaggg    1080
ggacgacaag ccgggcgccg tgggcaaggt ggtcccgttc ttcgaggcca aggtggtgga    1140
cctggacacc ggcaagaccc tgggcgtgaa ccagcggggc gagctgtgcg tgcggggggcc    1200
gatgatcatg agcggctacg tgaacaaccc ggaggccacc aacgccctca tcgacaagga    1260
cggctggctg cacagcggcg acatcgccta ctgggacgag gacgagcact tcttcatcgt    1320
cgaccggctg aagtcgctga tcaagtacaa gggctaccag gtggcgccgg ccgagctgga    1380
gagcatcctg ctccagcacc ccaacatctt cgacgccggc gtggccgggc tgccggacga    1440
cgacgccggc gagctgccgg ccgcggtggt ggtgctggag cacggcaaga ccatgacgga    1500
gaaggagatc gtcgactacg tggccagcca ggtgaccacc gccaagaagc tgcggggcgg    1560
cgtggtgttc gtggacgagg tcccgaaggg cctgaccggg aagctcgacg cccggaagat    1620
ccgcgagatc ctgatcaagg ccaagaaggg cggcaagatc gccgtgtaag actagtaagt    1680
gttggttttc tgccatcagt gaaaattctt aaacttggag caacaataaa aagcttccag    1740
aacagatcag atctaaaaaa aaaaaaaaaa aaaaaaaaaa aaaaaaaaaa aaaaaaaaaa    1800
aaaaaaaaaa aaaaaaaa                                                 1818
```

<210> SEQ ID NO 16
<211> LENGTH: 1877
<212> TYPE: DNA
<213> ORGANISM: Artificial Sequence
<220> FEATURE:
<223> OTHER INFORMATION: PpLuc(GC) ndufa1 A64

<400> SEQUENCE: 16

```
gggagaaagc ttgaggatgg aggacgccaa gaacatcaag aagggcccgg cgcccttcta      60
cccgctggag gacgggaccg ccggcgagca gctccacaag gccatgaagc ggtacgccct     120
ggtgccgggc acgatcgcct tcaccgacgc ccacatcgag gtcgacatca cctacgcgga     180
gtacttcgag atgagcgtgc gcctggccga ggccatgaag cggtacggcc tgaacaccaa     240
ccaccggatc gtggtgtgct cggagaacag cctgcagttc ttcatgccgg tgctgggcgc     300
cctcttcatc ggcgtggccg tcgccccggc gaacgacatc tacaacgagc gggagctgct     360
gaacagcatg gggatcagcc agccgaccgt ggtgttcgtg agcaagaagg gcctgcagaa     420
gatcctgaac gtgcagaaga gctgcccat catccagaag atcatcatca tggacagcaa     480
gaccgactac cagggcttcc agtcgatgta cacgttcgtg accagccacc tcccgccggg     540
cttcaacgag tacgacttcg tcccggagag cttcgaccgg acaagacca tcgccctgat     600
catgaacagc agcggcagca ccggcctgcc gaaggggtg gccctgccgc accggaccgc     660
ctgcgtgcgc ttctcgcacg cccgggaccc catcttcggc aaccagatca tcccggacac     720
cgccatcctg agcgtggtgc cgttccacca cggcttcggc atgttcacga ccctgggcta     780
cctcatctgc ggcttccggg tggtcctgat gtaccggttc gaggaggagc tgttcctgcg     840
gagcctgcag gactacaaga tccagagcgc gctgctcgtg ccgaccctgt tcagcttctt     900
cgccaagagc accctgatcg acaagtacga cctgtcgaac ctgcacgaga tcgccagcgg     960
gggcgccccg ctgagcaagg aggtgggcga ggccgtggcc aagcggttcc acctcccggg    1020
catccgccag ggctacggcc tgaccgagac cacgagcgcg atcctgatca cccccgaggg    1080
ggacgacaag ccgggcgccg tgggcaaggt ggtcccgttc ttcgaggcca aggtggtgga    1140
cctggacacc ggcaagaccc tgggcgtgaa ccagcggggc gagctgtgcg tgcgggggcc    1200
gatgatcatg agcggctacg tgaacaaccc ggaggccacc aacgccctca tcgacaagga    1260
cggctggctg cacagcggcg acatcgccta ctgggacgag gacgagcact tcttcatcgt    1320
cgaccggctg aagtcgctga tcaagtacaa gggctaccag gtggcgccgg ccgagctgga    1380
gagcatcctg ctccagcacc ccaacatctt cgacgccggc gtggccgggc tgccggacga    1440
cgacgccggc gagctgccgg ccgcggtggt ggtgctggag cacggcaaga ccatgacgga    1500
gaaggagatc gtcgactacg tggccagcca ggtgaccacc gccaagaagc tgcggggcgg    1560
cgtggtgttc gtggacgagg tcccgaaggg cctgaccggg aagctcgacg cccggaagat    1620
ccgcgagatc ctgatcaagg ccaagaaggg cggcaagatc gccgtgtaag actagtggaa    1680
gcatttcct gattgatgaa aaaataact cagttatggc catctacccc tgctagaagg    1740
ttacagtgta ttatgtagca tgcaatgtgt tatgtagtgc ttaataaaaa taaatgaaa    1800
aaaatgcaga tctaaaaaaa aaaaaaaaaa aaaaaaaaaa aaaaaaaaaa aaaaaaaaaa    1860
aaaaaaaaaa aaaaaaa                                                   1877
```

<210> SEQ ID NO 17
<211> LENGTH: 2494
<212> TYPE: DNA
<213> ORGANISM: Artificial Sequence
<220> FEATURE:
<223> OTHER INFORMATION: PpLuc(GC) atp5l A64

<400> SEQUENCE: 17

```
gggagaaagc ttgaggatgg aggacgccaa gaacatcaag aagggcccgg cgcccttcta    60
cccgctggag gacgggaccg ccggcgagca gctccacaag gccatgaagc ggtacgccct   120
ggtgccgggc acgatcgcct tcaccgacgc ccacatcgag gtcgacatca cctacgcgga   180
gtacttcgag atgagcgtgc gcctggccga ggccatgaag cggtacgcc  tgaacaccaa   240
ccaccggatc gtggtgtgct cggagaacag cctgcagttc ttcatgccgg tgctgggcgc   300
cctcttcatc ggcgtggccg tcgccccggc gaacgacatc tacaacgagc gggagctgct   360
gaacagcatg gggatcagcc agccgaccgt ggtgttcgtg agcaagaagg cctgcagaa   420
gatcctgaac gtgcagaaga gctgcccat catccgaaag atcatcatca tggacagcaa   480
gaccgactac cagggcttcc agtcgatgta cacgttcgtg accagccacc tcccgccggg   540
cttcaacgag tacgacttcg tcccggagag cttcgaccgg gacaagacca tcgccctgat   600
catgaacagc agcggcagca ccggcctgcc gaagggggtg gccctgccgc accggaccgc   660
ctgcgtgcgc ttctcgcacg cccgggaccc catcttcggc aaccagatca tcccggacac   720
cgccatcctg agcgtggtgc cgttccacca cggcttcggc atgttcacga ccctgggcta   780
cctcatctgc ggcttccggg tggtcctgat gtaccggttc gaggaggagc tgttcctgcg   840
gagcctgcag gactacaaga tccagagcgc gctgctcgtg ccgaccctgt tcagcttctt   900
cgccaagagc accctgatcg acaagtacga cctgtcgaac ctgcacgaga tcgccagcgg   960
gggcgccccg ctgagcaagg aggtgggcga ggccgtggcc aagcggttcc acctcccggg  1020
catccgccag ggctacggcc tgaccgagac cacgagcgcg atcctgatca cccccgaggg  1080
ggacgacaag ccgggcgccg tgggcaaggt ggtcccgttc ttcgaggcca aggtggtgga  1140
cctggacacc ggcaagaccc tgggcgtgaa ccagcggggc gagctgtgcg tgcggggcc  1200
gatgatcatg agcggctacg tgaacaaccc ggaggccacc aacgccctca tcgacaagga  1260
cggctggctg cacagcggcg acatcgccta ctgggacgag gacgagcact tcttcatcgt  1320
cgaccggctg aagtcgctga tcaagtacaa gggctaccag gtggcgccgg ccgagctgga  1380
gagcatcctg ctccagcacc ccaacatctt cgacgccggc gtggccgggc tgccggacga  1440
cgacgccggc gagctgccgg ccgcggtggt ggtgctggag cacggcaaga ccatgacgga  1500
gaaggagatc gtcgactacg tggccagcca ggtgaccacc gccaagaagc tgcggggcgg  1560
cgtggtgttc gtggacgagg tcccgaaggg cctgaccggg aagctcgacg cccggaagat  1620
ccgcgagatc ctgatcaagg ccaagaaggg cggcaagatc gccgtgtaag actagtagac  1680
caatctttaa catctgatta tatttgattt attatttgag tgttgttgga ccatgtgtga  1740
tcagactgct atctgaataa aataagattt gtcaaaactc agtgttttct ccatcagaca  1800
ctccatgaaa ggtcacaatt tctcttgata ttaagctggg ttgtctttaa caaccctaa  1860
atacacgtct gtttagcccg caattggaaa ggatatatgt ggcaatatta acctggtaca  1920
tgaatatatg gggataacat tttaatttga aggtttggaa tatatatatt taagctttat  1980
ttccagaaca gtgagggtta ggtcttggga aaactataac ttgccaaagt agaagaaata  2040
gtagtaccat atgccaaagt gatagagatg aatcatgtca gtagttagaa taacatttca  2100
actgttttct ttgctaaaat cacagaaaga ccctattgac aacatctatg tctgtaaaaa  2160
tgttagagta cttgtcatct tgaatatagc ctccccaaga gagaacaggg tggtattcta  2220
```

```
agtatgtttc tttgtaacat ctttagcagt aggacagagc catacatgtg aaatctgatt      2280
tttatgtgtg ttattcgttt gtctggtttt actacctttg caaaaacaaa atacccaaa       2340 gatatttaaa caaggttata atttagcatc ttccctggat ctaaatagta tattatatcc      2400
tgaaataaat gaaatgattg ctatagatct aaaaaaaaaa aaaaaaaaaa aaaaaaaaaa      2460
aaaaaaaaaa aaaaaaaaa aaaaaaaaaa aaaa                                  2494

<210> SEQ ID NO 18
<211> LENGTH: 155
<212> TYPE: DNA
<213> ORGANISM: Artificial Sequence
<220> FEATURE:
<223> OTHER INFORMATION: fragment of SEQ ID No. 1

<400> SEQUENCE: 18
aaaagcatct cagcctacca tgagaataag agaaagaaaa tgaagatcaa aagcttattc       60
atctgttttt cttttcgtt ggtgtaaagc caacaccctg tctaaaaaac ataaatttct       120
ttaatcattt tgcctctttt ctctgtgctt caatt                                 155

<210> SEQ ID NO 19
<211> LENGTH: 110
<212> TYPE: DNA
<213> ORGANISM: Artificial Sequence
<220> FEATURE:
<223> OTHER INFORMATION: fragment of SEQ ID No. 1

<400> SEQUENCE: 19
catcacattt aaaagcatct cagcctacca tgagaataag agaaagaaaa tgaagatcaa       60
aagcttattc atctgttttt cttttcgtt ggtgtaaagc caacaccctg                  110

<210> SEQ ID NO 20
<211> LENGTH: 110
<212> TYPE: DNA
<213> ORGANISM: Artificial Sequence
<220> FEATURE:
<223> OTHER INFORMATION: fragment of SEQ ID No. 1

<400> SEQUENCE: 20
aaaagcatct cagcctacca tgagaataag agaaagaaaa tgaagatcaa aagcttattc       60
atctgttttt cttttcgtt ggtgtaaagc caacaccctg tctaaaaaac                  110

<210> SEQ ID NO 21
<211> LENGTH: 110
<212> TYPE: DNA
<213> ORGANISM: Artificial Sequence
<220> FEATURE:
<223> OTHER INFORMATION: fragment of SEQ ID No. 1

<400> SEQUENCE: 21
cagcctacca tgagaataag agaaagaaaa tgaagatcaa aagcttattc atctgttttt      60 cttttcgtt ggtgtaaagc caacaccctg tctaaaaaac ataaatttct                 110

<210> SEQ ID NO 22
<211> LENGTH: 110
<212> TYPE: DNA
<213> ORGANISM: Artificial Sequence
<220> FEATURE:
<223> OTHER INFORMATION: fragment of SEQ ID No. 1

<400> SEQUENCE: 22
tgagaataag agaaagaaaa tgaagatcaa aagcttattc atctgttttt cttttcgtt      60
```

```
ggtgtaaagc caacaccctg tctaaaaaac ataaatttct ttaatcattt          110
```

<210> SEQ ID NO 23
<211> LENGTH: 110
<212> TYPE: DNA
<213> ORGANISM: Artificial Sequence
<220> FEATURE:
<223> OTHER INFORMATION: fragment of SEQ ID No. 1

<400> SEQUENCE: 23

```
agaaagaaaa tgaagatcaa aagcttattc atctgttttt cttttcgtt ggtgtaaagc    60 caacaccctg tctaaaaaac ataaatttct ttaatcattt tgcctctttt             110
```

<210> SEQ ID NO 24
<211> LENGTH: 110
<212> TYPE: DNA
<213> ORGANISM: Artificial Sequence
<220> FEATURE:
<223> OTHER INFORMATION: fragment of SEQ ID No. 1

<400> SEQUENCE: 24

```
tgaagatcaa aagcttattc atctgttttt cttttcgtt ggtgtaaagc caacaccctg   60
tctaaaaaac ataaatttct ttaatcattt tgcctctttt ctctgtgctt            110
```

<210> SEQ ID NO 25
<211> LENGTH: 110
<212> TYPE: DNA
<213> ORGANISM: Artificial Sequence
<220> FEATURE:
<223> OTHER INFORMATION: fragment of SEQ ID No. 1

<400> SEQUENCE: 25

```
aagcttattc atctgttttt cttttcgtt ggtgtaaagc caacaccctg tctaaaaaac    60
ataaatttct ttaatcattt tgcctctttt ctctgtgctt caattaataa            110
```

<210> SEQ ID NO 26
<211> LENGTH: 110
<212> TYPE: DNA
<213> ORGANISM: Artificial Sequence
<220> FEATURE:
<223> OTHER INFORMATION: fragment of SEQ ID No. 1

<400> SEQUENCE: 26

```
atctgttttt cttttcgtt ggtgtaaagc caacaccctg tctaaaaaac ataaatttct    60
ttaatcattt tgcctctttt ctctgtgctt caattaataa aaaatggaaa            110
```

<210> SEQ ID NO 27
<211> LENGTH: 151
<212> TYPE: DNA
<213> ORGANISM: Artificial Sequence
<220> FEATURE:
<223> OTHER INFORMATION: fragment of SEQ ID No. 1

<400> SEQUENCE: 27

```
cagcctacca tgagaataag agaaagaaaa tgaagatcaa aagcttattc atctgttttt   60 cttttcgtt ggtgtaaagc caacaccctg tctaaaaaac ataaatttct ttaatcattt  120
tgcctctttt ctctgtgctt caattaataa a                                151
```

<210> SEQ ID NO 28
<211> LENGTH: 121
<212> TYPE: DNA

```
<213> ORGANISM: Artificial Sequence
<220> FEATURE:
<223> OTHER INFORMATION: fragment of SEQ ID No. 1

<400> SEQUENCE: 28
tgaagatcaa aagcttattc atctgttttt cttttcgtt ggtgtaaagc caacaccctg      60
tctaaaaaac ataaatttct ttaatcattt tgcctctttt ctctgtgctt caattaataa     120
a                                                                     121

<210> SEQ ID NO 29
<211> LENGTH: 91
<212> TYPE: DNA
<213> ORGANISM: Artificial Sequence
<220> FEATURE:
<223> OTHER INFORMATION: fragment of SEQ ID No. 1

<400> SEQUENCE: 29 cttttcgtt ggtgtaaagc caacaccctg tctaaaaaac ataaatttct ttaatcattt      60
tgcctctttt ctctgtgctt caattaataa a                                    91

<210> SEQ ID NO 30
<211> LENGTH: 60
<212> TYPE: DNA
<213> ORGANISM: Artificial Sequence
<220> FEATURE:
<223> OTHER INFORMATION: fragment of SEQ ID No. 1

<400> SEQUENCE: 30
aagcttattc atctgttttt cttttcgtt ggtgtaaagc caacaccctg tctaaaaaac      60

<210> SEQ ID NO 31
<211> LENGTH: 24
<212> TYPE: DNA
<213> ORGANISM: Artificial Sequence
<220> FEATURE:
<223> OTHER INFORMATION: example for a histone stem-loop sequence

<400> SEQUENCE: 31
caaaggctct tttcagagcc acca                                            24

<210> SEQ ID NO 32
<211> LENGTH: 244
<212> TYPE: DNA
<213> ORGANISM: Artificial Sequence
<220> FEATURE:
<223> OTHER INFORMATION: fragment of 3'UTR of an albumin gene

<400> SEQUENCE: 32
aaacatcaca attaagaaca tctcagccta ccatgagaac aagagaaata aaatgaagat      60
caaaagctta ttcatctgtt tttcttttc attggtataa agccaacacc ctgtctaaaa     120
aactataaat ttctttaatc attttgcctc ttttctctgt gcttcaatta ataaaaaatg     180
gaaagaatct agatctaaaa aaaaaaaaaa aaaaaaaaa aaaaaaaaa aaaaaaaaa       240 aaaa                                                                  244

<210> SEQ ID NO 33
<211> LENGTH: 244
<212> TYPE: RNA
<213> ORGANISM: Artificial Sequence
<220> FEATURE:
<223> OTHER INFORMATION: fragment of 3'UTR of an albumin gene

<400> SEQUENCE: 33
```

```
aaacaucaca auuaagaaca ucucagccua ccaugagaac aagagaaaua aaaugaagau    60
caaaagcuua uucaucuguu uuucuuuuuc auugguauaa agccaacacc cugucuaaaa    120
aacuauaaau uucuuuaauc auuuugccuc uuuucucugu gcuucaauua auaaaaaaug    180
gaaagaaucu agaucuaaaa aaaaaaaaaa aaaaaaaaaa aaaaaaaaaa aaaaaaaaaa    240
aaaa                                                                 244
```

<210> SEQ ID NO 34
<211> LENGTH: 184
<212> TYPE: DNA
<213> ORGANISM: Artificial Sequence
<220> FEATURE:
<223> OTHER INFORMATION: fragment of 3'UTR of an albumin gene

<400> SEQUENCE: 34

```
acacatcaca accacaacct tctcaggcta ccctgagaaa aaaagacatg aagactcagg    60
actcatcttt tctgttggtg taaaatcaac accctaagga acacaaattt ctttaaacat    120
ttgacttctt gtctctgtgc tgcaattaat aaaaaatgga agaatctac agatctaaaa    180 aaaa                                                                 184
```

<210> SEQ ID NO 35
<211> LENGTH: 184
<212> TYPE: RNA
<213> ORGANISM: Artificial Sequence
<220> FEATURE:
<223> OTHER INFORMATION: fragment of 3'UTR of an albumin gene

<400> SEQUENCE: 35

```
acacaucaca accacaaccu ucucaggcua cccugagaaa aaaagacaug aagacucagg    60
acucaucuuu ucuguuggug uaaaaucaac acccuaagga acacaaauuu cuuuaaacau    120
uugacuucuu gucucugugc ugcaauuaau aaaaaaugga agaaucuac agaucuaaaa    180 aaaa                                                                 184
```

<210> SEQ ID NO 36
<211> LENGTH: 260
<212> TYPE: DNA
<213> ORGANISM: Artificial Sequence
<220> FEATURE:
<223> OTHER INFORMATION: fragment of 3'UTR of albumin plus poly(A)

<400> SEQUENCE: 36

```
aaacatcaca attaagaaca tctcagccta ccatgagaac aagagaaata aatgaagat    60 caaaagctta ttcatctgtt tttcttttc attggtataa agccaacacc ctgtctaaaa    120
aactataaat ttctttaatc attttgcctc ttttctctgt gcttcaatta ataaaaaatg    180
gaaagaatct agatctaaaa aaaaaaaaaa aaaaaaaaaa aaaaaaaaaa aaaaaaaaaa    240
aaaaaaaaaa aaaaaaaaaa                                                260
```

<210> SEQ ID NO 37
<211> LENGTH: 260
<212> TYPE: DNA
<213> ORGANISM: Artificial Sequence
<220> FEATURE:
<223> OTHER INFORMATION: fragment of 3'utr of albumin plus poly(a)

<400> SEQUENCE: 37

```
aaacaucaca auuaagaaca ucucagccua ccaugagaac aagagaaaua aaaugaagau    60
```

| caaaagcuua uucaucuguu uuucuuuuuc auugguauaa agccaacacc cugucuaaaa | 120 |
| aacuauaaau uucuuaauc auuuugccuc uuuucucugu gcuucaauua auaaaaaug | 180 |
| gaaagaaucu agaucuaaaa aaaaaaaaaa aaaaaaaaaa aaaaaaaaaa aaaaaaaaaa | 240 |
| aaaaaaaaaa aaaaaaaaaa | 260 |

<210> SEQ ID NO 38
<211> LENGTH: 240
<212> TYPE: DNA
<213> ORGANISM: Artificial Sequence
<220> FEATURE:
<223> OTHER INFORMATION: fragment of 3'UTR of albumin plus poly(A)

<400> SEQUENCE: 38

| acacatcaca accacaacct tctcaggcta ccctgagaaa aaaagacatg aagactcagg | 60 |
| actcatcttt tctgttggtg taaaatcaac accctaagga acacaaattt ctttaaacat | 120 |
| ttgacttctt gtctctgtgc tgcaattaat aaaaaatgga agaatctac agatctaaaa | 180 |
| aaaaaaaaaa aaaaaaaaaa aaaaaaaaaa aaaaaaaaaa aaaaaaaaaa aaaaaaaaaa | 240 |

<210> SEQ ID NO 39
<211> LENGTH: 240
<212> TYPE: RNA
<213> ORGANISM: Artificial Sequence
<220> FEATURE:
<223> OTHER INFORMATION: fragment of 3'UTR of albumin plus poly(A)

<400> SEQUENCE: 39

| acacaucaca accacaaccu ucucaggcua cccugagaaa aaaagacaug aagacucagg | 60 |
| acucaucuuu ucuguuggug uaaaaucaac acccuaagga acacaaauuu cuuuaaacau | 120 |
| uugacuucuu gucucugugc ugcaauuaau aaaaaaugga agaaucuac agaucuaaaa | 180 |
| aaaaaaaaaa aaaaaaaaaa aaaaaaaaaa aaaaaaaaaa aaaaaaaaaa aaaaaaaaaa | 240 |

<210> SEQ ID NO 40
<211> LENGTH: 1936
<212> TYPE: DNA
<213> ORGANISM: Artificial Sequence
<220> FEATURE:
<223> OTHER INFORMATION: PpLuc(GC) - albumin8 - A64

<400> SEQUENCE: 40

| gggagaaagc ttgaggatgg aggacgccaa gaacatcaag aagggcccgg cgcccttcta | 60 |
| cccgctggag gacgggaccg ccggcgagca gctccacaag gccatgaagc ggtacgccct | 120 |
| ggtgccgggc acgatcgcct tcaccgacgc ccacatcgag gtcgacatca cctacgcgga | 180 |
| gtacttcgag atgagcgtgc gcctggccga ggccatgaag cggtacgcc tgaacaccaa | 240 |
| ccaccggatc gtggtgtgct cggagaacag cctgcagttc ttcatgccgg tgctgggcgc | 300 |
| cctcttcatc ggcgtggccg tcgccccggc gaacgacatc tacaacgagc gggagctgct | 360 |
| gaacagcatg gggatcagcc agccgaccgt ggtgttcgtg agcaagaagg gcctgcagaa | 420 |
| gatcctgaac gtgcagaaga agctgcccat catccagaag atcatcatca tggacagcaa | 480 |
| gaccgactac cagggcttcc agtcgatgta cacgttcgtg accagccacc tcccgccggg | 540 |
| cttcaacgag tacgacttcg tcccggagag cttcgaccgg acaagacca tcgccctgat | 600 |
| catgaacagc agcggcagca ccggcctgcc gaaggggtg ccctgccgc accggaccgc | 660 |
| ctgcgtgcgc ttctcgcacg cccgggaccc catcttcggc aaccagatca tcccggacac | 720 |
| cgccatcctg agcgtggtgc cgttccacca cggcttcggc atgttcacga ccctgggcta | 780 |

```
cctcatctgc ggcttccggg tggtcctgat gtaccggttc gaggaggagc tgttcctgcg    840
gagcctgcag gactacaaga tccagagcgc gctgctcgtg ccgaccctgt tcagcttctt    900
cgccaagagc accctgatcg acaagtacga cctgtcgaac ctgcacgaga tcgccagcgg    960
gggcgccccg ctgagcaagg aggtgggcga ggccgtggcc aagcggttcc acctcccggg   1020
catccgccag ggctacggcc tgaccgagac cacgagcgcg atcctgatca ccccgaggg    1080 ggacgacaag ccgggcgccg tgggcaaggt ggtcccgttc ttcgaggcca aggtggtgga   1140
cctggacacc ggcaagaccc tgggcgtgaa ccagcggggc gagctgtgcg tgcgggggcc   1200
gatgatcatg agcggctacg tgaacaaccc ggaggccacc aacgccctca tcgacaagga   1260
cggctggctg cacagcggcg acatcgccta ctgggacgag gacgagcact tcttcatcgt   1320
cgaccggctg aagtcgctga tcaagtacaa gggctaccag gtggcgccgg ccgagctgga   1380
gagcatcctg ctccagcacc ccaacatctt cgacgccggc gtggccgggc tgccggacga   1440
cgacgccggc gagctgccgg ccgcggtggt ggtgctggag cacggcaaga ccatgacgga   1500
gaaggagatc gtcgactacg tggccagcca ggtgaccacc gccaagaagc tgcggggcgg   1560
cgtggtgttc gtggacgagg tcccgaaggg cctgaccggg aagctcgacg cccggaagat   1620
ccgcgagatc ctgatcaagg ccaagaaggg cggcaagatc gccgtgtaag actagtaaac   1680
atcacaatta gaacatctca gcctaccat gagaacaaga gaaataaat gaagatcaaa      1740 agcttattca tctgtttttc ttttcattg gtataaagcc aacaccctgt ctaaaaaact    1800 ataaattct ttaatcattt tgcctctttt ctctgtgctt caattaataa aaaatgaaaa    1860
gaatctagat ctaaaaaaaa aaaaaaaaaa aaaaaaaaaa aaaaaaaaaa aaaaaaaaaa   1920
aaaaaaaaaa aaaaa                                                   1936

<210> SEQ ID NO 41
<211> LENGTH: 1916
<212> TYPE: DNA
<213> ORGANISM: Artificial Sequence
<220> FEATURE:
<223> OTHER INFORMATION: PpLuc(GC) - albumin9 - A64

<400> SEQUENCE: 41
gggagaaagc ttgaggatgg aggacgccaa gaacatcaag aagggcccgg cgcccttcta     60
cccgctggag gacgggaccg ccggcgagca gctccacaag gccatgaagc ggtacgccct    120
ggtgccgggc acgatcgcct tcaccgacgc ccacatcgag gtcgacatca cctacgcgga    180
gtacttcgag atgagcgtgc gcctggccga ggccatgaag cggtacgccc tgaacaccaa    240
ccaccggatc gtggtgtgct cggagaacag cctgcagttc ttcatgccgg tgctgggcgc    300
cctcttcatc ggcgtggccg tcgccccggc gaacgacatc tacaacgagc gggagctgct    360
gaacagcatg gggatcagcc agccgaccgt ggtgttcgtg agcaagaagg gcctgcagaa    420
gatcctgaac gtgcagaaga gctgcccat catccgaag atcatcatca tggacagcaa    480
gaccgactac cagggcttcc agtcgatgta cacgttcgtg accagccacc tcccgccggg    540
cttcaacgag tacgacttcg tcccggagag cttcgaccgg acaagacca tcgccctgat    600 catgaacagc agcggcagca ccggcctgcc gaaggggtg gccctgccgc accgaccgc    660 ctgcgtgcgc ttctcgcacg cccgggaccc catcttcggc aaccagatca tcccggacac    720
cgccatcctg agcgtggtgc cgttccacca cggcttcggc atgttcacga ccctgggcta    780
cctcatctgc ggcttccggg tggtcctgat gtaccggttc gaggaggagc tgttcctgcg    840
```

```
                                                        -continued gagcctgcag gactacaaga tccagagcgc gctgctcgtg ccgaccctgt tcagcttctt      900
cgccaagagc accctgatcg acaagtacga cctgtcgaac ctgcacgaga tcgccagcgg      960
gggcgccccg ctgagcaagg aggtgggcga ggccgtggcc aagcggttcc acctcccggg     1020
catccgccag ggctacggcc tgaccgagac cacgagcgcg atcctgatca cccccgaggg     1080
ggacgacaag ccgggcgccg tgggcaaggt ggtcccgttc ttcgaggcca aggtggtgga     1140
cctggacacc ggcaagaccc tgggcgtgaa ccagcggggc gagctgtgcg tgcggggcc      1200 gatgatcatg agcggctacg tgaacaaccc ggaggccacc aacgccctca tcgacaagga     1260
cggctggctg cacagcggcg acatcgccta ctgggacgag gacgagcact tcttcatcgt     1320
cgaccggctg aagtcgctga tcaagtacaa gggctaccag gtggcgccgg ccgagctgga     1380
gagcatcctg ctccagcacc ccaacatctt cgacgccggc gtggccgggc tgccggacga     1440
cgacgccggc gagctgccgg ccgcggtggt ggtgctggag cacggcaaga ccatgacgga     1500
gaaggagatc gtcgactacg tggccagcca ggtgaccacc gccaagaagc tgcggggcgg     1560
cgtggtgttc gtggacgagg tcccgaaggg cctgaccggg aagctcgacg cccggaagat     1620
ccgcgagatc ctgatcaagg ccaagaaggg cggcaagatc gccgtgtaag actagtacac     1680
atcacaacca caaccttctc aggctaccct gagaaaaaaa gacatgaaga ctcaggactc     1740
atcttttctg ttggtgtaaa atcaacaccc taaggaacac aaatttcttt aaacatttga     1800
cttcttgtct ctgtgctgca attaataaaa aatggaaaga atctacagat ctaaaaaaaa     1860
aaaaaaaaaa aaaaaaaaaa aaaaaaaaaa aaaaaaaaaa aaaaaaaaaa aaaaaa         1916
```